US005648465A

United States Patent [19]
Margolis et al.

[11] Patent Number: 5,648,465
[45] Date of Patent: Jul. 15, 1997

[54] CLONING AND EXPRESSION OF NEUROCAN, A CHONDROITIN SULFATE PROTEOGLYCAN

[75] Inventors: Richard U. Margolis; Uwe Rauch; Renee K. Margolis, all of New York, N.Y.

[73] Assignees: New York University, New York; The Research Foundation of State University of New York, Albany, both of N.Y.; a part interest

[21] Appl. No.: 340,428

[22] Filed: Nov. 14, 1994

Related U.S. Application Data

[63] Continuation of Ser. No. 922,911, Aug. 3, 1992, abandoned.
[51] Int. Cl.$^6$ .......................... C07K 14/47; C12N 15/12
[52] U.S. Cl. ..................... 530/350; 530/395; 435/69.1
[58] Field of Search .................................... 530/350, 395; 514/8; 435/69.1

[56] References Cited

U.S. PATENT DOCUMENTS 5,180,808  1/1993  Ruoslahti et al. ..................... 530/350

FOREIGN PATENT DOCUMENTS 9000606  1/1990  WIPO.
9218629  10/1992  WIPO.

OTHER PUBLICATIONS

Doege et al., "Complete Coding Sequence and Deduced Primary Structure of the Human Cartilage Large Aggregating Proteoglycan, Aggrecan," *The Journal of Biological Chemistry*, vol. 266, No. 2, pp. 894–902, 1991.

Grumet et al, "Functional Characterization of Chondroitin Sulfate Proteoglycans of Brain: Interactions with Neurons and Neural Cell Adhesion Molecules," *The Journal of Cell Biology*, vol. 120, No. 3, pp. 815–824, 1993.

Neame et al, "An Amino Acid Sequence Common to Both Cartilage Proteoglycan and Link Protein," *The Journal of Biological Chemistry*, vol. 260, No. 23, pp. 12402–12404, 1985.

Gowda et al, "Prescence of the HNK–1 Epitope on Poly(N–acetyllactosaminyl) Oliogsaccharides and Identification of Multiple Core Proteins in the Chondroitin Sulfate Proteoglycans of Brain," *Biochemisty*, vol. 28, pp. 4468–4474, 1989.

Rauch et al, "Cloning and Primary Structure of Neurocan, a Developmentally Regulated, Aggregating Chondroitin Sulfate Proteoglycan of Brain," *The Journal of Biological Chemistry*, vol. 267, No. 27, pp. 19536–19547, 1992.

Snow, D.M. et al., Sulfated Proteoglycans in Astroglial Barriers Inhibit Neurite Outgrowth *in Vitro*, Experimental Neurology, 109:111–130 (1990).

Lo, S.K. et al., Endothelial–Leukocyte Adhesion Molecule 1 Stimulates the Adhesive Activity of Leukocyte Integrin CR3 (CD11b/CD18, Mac–1, $\alpha_m\beta_2$) on Human Neutrophils, J. Exp. Med., 173:1493–1500 (1991).

Kuijpers, T.W. et al., Role of Endothelial Leukocyte Adhesion Molecule–1 and Platelet–Activating Factor in Neutrophil Adherence to II–1–Prestimulated Endothelial Cells, The Journal of Immunology, 147:1369–1376 (1991).

McKeon, R.J. et al., Reduction of Neurite Outgrowth in a Model of Glial Scarring Following CNS Injury is Correlated with the Expression of Inhibitory Molecules on Reactive Astrocytes, The Journal of Neurosciences 11(11):3398–3411 (1991).

Picker, L.J. et al., Elam–1 is an Adhesion Molecule for Skin–homing T Cells, Nature, 349:796–799 (1991).

Spertini, O. et al., Regulation of Leukocyte Migration by Activation of the Leukocyte Adhesion Molecule–1 (LAM–1) Selectin, Nature, 349:691–694 (1991).

Larsen, E. et al., Padgem–dependent Adhesion of Platelets to Monocytes and Neutrophils is Mediated by a Lineage–Specific Carbohydrage LNF III (DC15), Cell, 63:467–474 (1990).

Margolis, R.K. et al., Effects of β–xylosides on Proteoiglycan Biosynthesis and Morphology of PC12 Pheo–Chromocytoma Cells and Primary Cultures of Rat Cerebellum, Journal of Cell Science, 99:237–246 (1991).

Hoffman, S. et al., Molecular Forms, Binding Functions, and Developmental Expression Patterns of Cytotactin and Cytotactin–binding Proteologlycan, An Interactive Pair of Extracellular Matrix Molecules, The Journal of Biology, 106:519–532 (1988).

Moore, K.L. et al., GMP–140 Binds to a Glycoprotein Receptor on Human Neutrophils: Evidence for a Lectin–like Interaction, The Journal of Cell Biology, 112:491–499 (1991).

Berg, E.L. et al. The Human Peripheral Lymph Node Vascular Addressin Is a Ligand for LECAM–1, the Peripheral Lymph Node Homing Receptor, The Journal of Cell Biology, 114:343–349 (1991).

Brandley, B.K. et al., Carbohydrate Ligands of the LEC Cell Adhesion Molecules, Cell, 63:861–863 (1989).

Johnston, G.I. et al., Cloning of GMP–140, a Granule Membrane Protein of Platelets and Endothelium: Sequence Similarity to Proteins Involved in Cell Adhesion and Inflammation, Cell, 56:1033–1044 (1989).

Brittis, P.A. et al., Chondroitin Sulfate as a Regulator of Neuronal Patterning in the Retina, Science, 255: 733–736 (1992).

Phillips, M.L. et al., Elam–1 Mediates Cell Adhesion by Recognition of a Carbohydrate Ligand, Sialy–Le, Science 250:1130–1132 (1990).

Walz, G. et al., Recognition by ELAM–1 of the Sialy–Le$^x$ Determination on Myeloid and Tumor Cells, Science, 243:1132–1135 (1990).

(List continued on next page.)

*Primary Examiner*—David L. Fitzgerald
*Attorney, Agent, or Firm*—Browdy and Neimark

[57] ABSTRACT

Novel eukaryotic neurocan polypeptides, derivatives and analogs thereof and nucleic acid encoding therefor, which are useful for providing soluble, biologically active heterologous proteins in hosts, as well as hosts transformed with this nucleic acid and methods for producing soluble heterologous proteins in hosts using such molecules, and therapeutic uses thereof.

4 Claims, 14 Drawing Sheets

OTHER PUBLICATIONS

Bevilacqua, M.P. et al., Endothelial Leukocyte Adhesion Molecule 1: An Inducible Receptor for Neutrophils Related to Complement Regulatory Proteins and Lectins, Science, 243:1160–1165 (1989).

Oakley, R.A. et al., Peanut Agglutinin and Chondroitin–6–sulfate are Molecular Markers for Tissues That Act as Barriers to Axon Advance in the Avian Embryo, Development Biology, 147:187–206 (1991).

Crossin, K.L. et al., Cytotactin and Its Proteoglycan Ligand Mark Structural and Functional Boundaries in Somatosensory Cortex of the Early Postnatal Mouse, Developmental Biology, 136:381–392 (1989).

Snow, D.M. et al., A Chondroitin Sulfate Proteoglycan May Influence the Direction of Retinal Ganglion Cell Outgrowth, Development, 113:1473–1485 (1991).

Snow, D. M. et. al., Molecular and Cellular Characterization of the Glial Roof Plate of the Spinal Cord and Optic Tectum: A Possible Role for a Proteoglycan in the Development of an Axon Barrier, Developmental Biology, 138:359–376 (1990).

Perris, R. et al., Spatial and Temporal Changes in the Distribution of Proteologlycans and During Avian Neural Crest Development, Development, 111:583–599 (1991).

Tyrrell, D. et al., Structural Requirements for the Carbohydrate Ligand of E–Selectin, Proc. Natl. Acad. Sci. USA, 88:10372–10376 (1991).

Perris, R., Inhibition of Neural Crest Cell Migration by Aggregatin Chondroitin Sulfate Proteoglycans is Mediated by Their Hyaluronan–Binding Region, Developmental Biology, 137:1–12 (1990).

Polley et al., CD62 and Endothelial Cell–Leukocyte Adhesion Molecule 1 (ELAM–1) Recognize the Same Carbohydrate Ligand, Sialyl–Lewis X, Proc. Natl. Acad. Sci. USA., 88:6224–6228 (1991).

Zimmerman et al. (1989) EMBO J. 8(10) 2975–2981.

Ranch et al (1991) J. Biol. Chem 266, 14785–14801.

Gowda, D.C., et al. (1989) *Biochemistry* 28: 4468–4474.

Margolis, R. V., et al. (1994) *Meth. Engyrol.* 245: 105–126.

FIG. 1A

| | | |
|---|---|---|
| 150 kDa core glycoprotein: | LRAPKL - LL P- - - LVPNV | (SEQ. ID No. 2) |
| 45 kDa core glycoprotein: | FWEEVA- -GQEDPTDPPENNN- - - H | (SEQ. ID No. 3) |
| 35/47 kDa endo Lys-C peptides: | VVAE - PGLEGF- EEVA- - | (SEQ. ID No. 4) |
| | DLKVVAE - PGLEGFWEEVA-GQEDPTDP -ENNP-LHGG | (SEQ. ID No. 5) |
| 35 kDa endo Asp-N peptide: | Y - - - - DQGYAGEN - EI DIDDD LLLPPENG - | (SEQ. ID No. 6) |
| 24 kDa CNBr peptide 3: | VAHENG - - - NDVP - NYNLPYV- KKGTVL- GPPPAVVHA | (SEQ. ID No. 7) |
| 21 kDa CNBr peptide 4: | VAHENGRw NDVP c NYNLPYV- KKGTVL- GPPPAV- NAKLVGV-K--YN | (SEQ. ID No. 8) |
| 13 kDa CNBr peptide 5: | | |

FIG. 1B

Sense primer (from Asp-N peptide):

```
                     C   A    C        A   A
                     A        A            A
5'  GGACTGCAGGATCC IGGI TIGA GGITT TGGGA GA G  3'   (SEQ. ID No. 9)
                     T    G    T        G
                                        G
```

Antisense primer (from CNBr peptide 5):

```
                         A  A       A        A
                         A  A       A
5'  TACGTCGACAAGCTT TA TT CAIGGIAC TC TTCC  3'   (SEQ.iD No. 10)
                         G  G       G
                                    G
```

FIG. 2A

| | | |
|---|---|---|
| 245 kDa core glycoprotein: | DQDTQDTTTTEK | (SEQ. ID No. 11) |
| 70 kDa CNBr peptide 1: | LKSGSGPIQAALAELVALP - FFTLQPRQ | (SEQ. ID No. 12) |
| 65 kDa endo Lys-C peptide: | SGSGPIQAALAELVALP - FFTLQPRQSPLGDIPRIKWTK | (SEQ. ID No. 13) |

Tryptic peptides of 65 kDa endo Lys-C peptide:

| | |
|---|---|
| VSLPAYPR | (SEQ. ID No. 14) |
| GIEDEQDLVTLEVTGVVFHYR | (SEQ. ID No. 15) |
| ELGGEVFYVGPAR | (SEQ. ID No. 16) |
| QGAALASVGQLHLAWHEGLDQCDPGWLAD | (SEQ. ID No. 17) |

FIG. 2B

Antisense primer used for reverse transcription (based on 5' sequence of 150 kDa 1D1 coding region):

5'  CTGCAGGATCCACAGTTTGGGGGCTCGAAG  3'  (SEQ. ID No. 18)

Primers used for PCR amplification of reverse transcription product

Sense primer based on 70 kDa CNBr peptide1:

```
              A       AT
              A   T   AT
5'  CCGCGGATCCIATICA GCIGCI TIGCIGA TIGTIGC  3'
              G       C   GC
```
(SEQ. ID No. 19)

Antisense primer based on consensus sequence of tandem repeat:

```
        G       G       G   G
5'  CTTAAGCTTG TCIGCIA CCAICCIGC TC CA  3'
        A       A       A   A
```
(SEQ. ID No. 20)

PCR primers based on amplified sequence of reverse transcription product:

Sense:       5'  CTGCTTCTTACCCTTCAACCAC    3'   (SEQ. ID No. 21)
Antisense:   5'  AGTTGTCAAAGCCATCTTCGAAC   3'   (SEQ. ID No. 22)

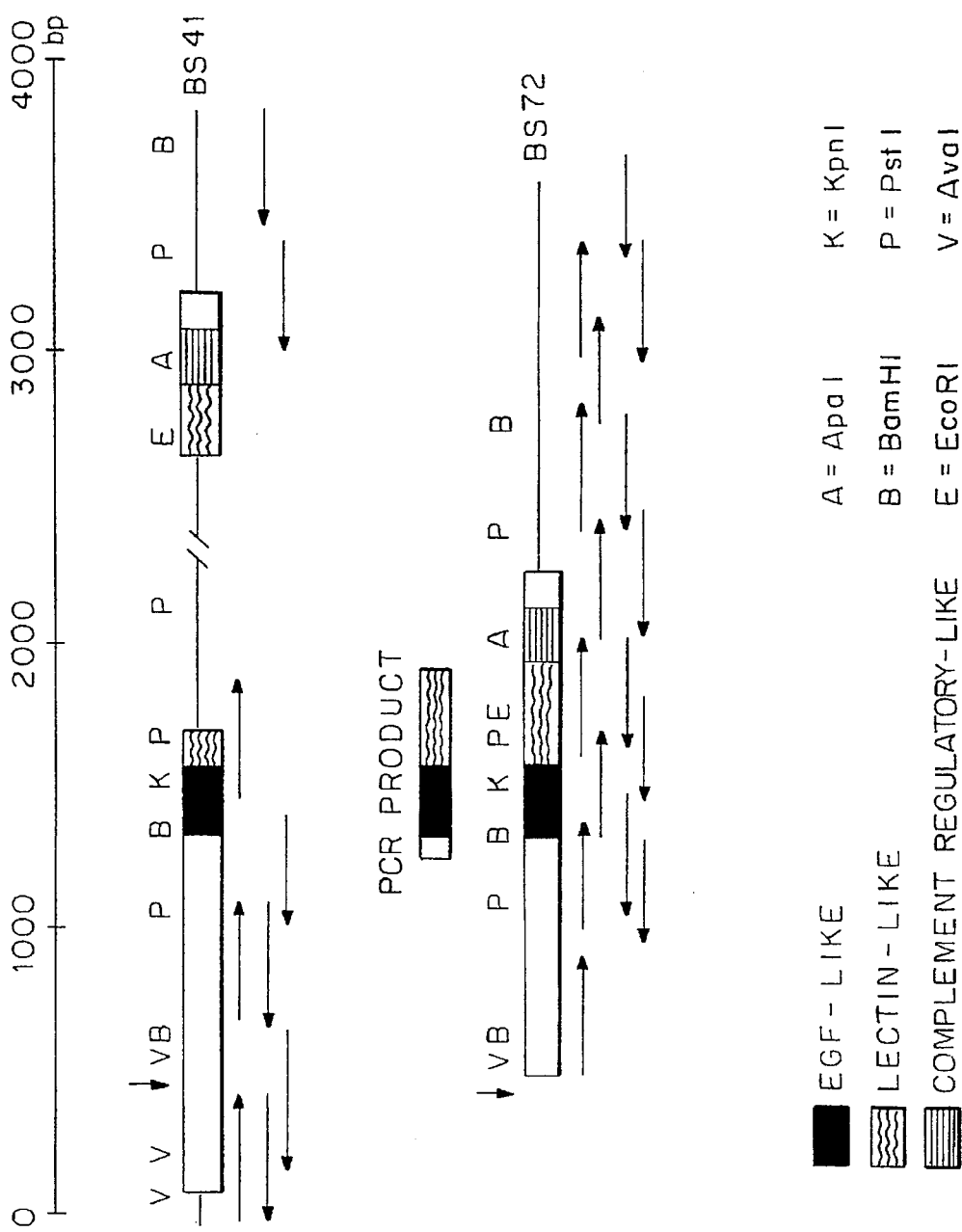

FIG. 4A (SEQ ID NO. 1)

```
ATG GCG GAA GCC GAA  A ACA CCG GAG CCA GGC GTC TCC TTT GTG TGG CCC GGA ACC GTG GGG ATG TGT CCG CGC TAA GGA GCC TCC AGT       76
 M   G   A   E         T   P   E   P   G   V   S   F   V   W   P   G   T   V   G   M   C   P   R   *   G   A   S   S      166
                                                                                                                              30

ACC ACG GAA AAG GCG CTT CAC ATG CTG AAG TCG GGG TCA GGA CCC ATC CAG GCT GCT TTG GCA GAG TTA GTG GCC TTA GTG CCC TTC TTT      256
 T   T   E   K   A   L   H   M   L   K   S   G   S   G   P   I   Q   A   A   L   A   E   L   V   A   L   V   P   F   F       60

ACC CTT CAA CCA CCG CAA AGC CCC AAA GAC ATT CCT CCG ATC AAG TGG ACG AAA GTT CAG ACT GCA TCA GCC CAG CGA CAG CAG GAT TTG      346
 T   L   Q   P   P   Q   S   P   K   D   I   P   P   I   K   W   T   K   V   Q   T   A   S   A   Q   R   Q   Q   D   L       90

CCA ATC TTG GTG GCC AAA GAC AAT GTG CGT GTG GCC CGT GTG GGC CAG CGG TCA CGG TTG CCT GCC CGG CAC CAG CAG CAC AGA GCC      436
 P   I   L   V   A   K   D   N   V   R   V   A   R   V   G   Q   R   S   R   L   P   A   R   H   Q   Q   H   R   A       120

AAT GCT ACA CTT CTG GGG ACG GGC GAA GAC TTC TGC CAA GTG GTG AAG GGT ATC GAG GCC GAT GAG CAG CAG GAC      526
 N   A   T   L   L   G   T   G   E   D   F   C   Q   V   V   K   G   I   E   A   D   E   Q   Q   D       150

CTG GTA ACC CTG GAA GTG ACG GGC GTC GTG TAT TAT CGG CGC GCC TAT GCG TTG ACC GCG AAC TGC GAT GCC CAG CAG CCT      616
 L   V   T   L   E   V   T   G   V   V   Y   Y   R   R   A   Y   A   L   T   A   N   C   D   A   Q   Q   *       180

TGT CAC CTG AGC TCC GCT ACC ATT GCG CAG CAC CTG CAG GCT CAG TTT GAC GGC TTT GAC AAC TGC GAT GGC TGG CTC      706
 C   H   L   S   S   A   T   I   A   Q   H   L   Q   A   Q   F   D   G   F   D   N   C   D   G   W   L       210

TCA GAC CGC ACG GTC CGG TAC CGG ATC ACT CAG CGT TCG CGT TTT CCC GGT GAT CGC AGC CTG GTC CCA GGT GTC TAC GGG      796
 S   D   R   T   V   R   Y   R   I   T   Q   R   S   R   F   P   G   D   R   S   L   V   P   G   V   Y   G       240

AGA CAC GAC CCG CAG CCG GCG GCA GCG CGG GAA GAT GTC TAC TGC TTT GCC TGC CTA GGG GGT GCA GCG GTT TAC TTT CGA      886
 R   H   D   P   Q   P   A   A   A   R   E   D   V   Y   C   F   A   C   L   G   G   A   A   V   Y   F   R       270

ACC CTG GCG GGG GCG CGG GGC GCA GCG CTG GCC TCC GTG GGA CAG TTG CAC CTG GCC TGG CAC GAG GGC CTG      976
 T   L   A   G   A   R   G   A   A   L   A   S   V   G   Q   L   H   L   A   W   H   E   G   L       300

GAC CAG TGC GAC CCG GGC ATG CTG GCA ACT CCA CAG ATC CCA GAC GTG TAC CCG CGG CGT TGC GGG TCC GCT CCA GGT     1066
 D   Q   C   D   P   G   M   L   A   T   P   Q   I   P   D   V   Y   P   R   R   C   G   S   A   P   G      330

GTG CGC ACG TGC GAC CCG TAC TTC GCC TTC CGC ACT AAC CGC GCC TAT CGC GCC TTT CCT GCG CCA GGA GCG TCA GCC AAT CAC CAT     1156
 V   R   T   C   D   P   Y   F   A   F   R   T   N   R   A   Y   R   A   F   P   A   P   G   A   S   A   N   H   H      360

ACA CCA CAA CGT CGG GAC TCC GAG ATC CCC TCA GCA GAC TCC GAG GGG GAG ATT GTG TCA GCG GAG CCA CCA GAA CTA AAG     1246
 T   P   Q   R   R   D   S   E   I   P   S   A   D   S   E   G   E   I   V   S   A   E   P   P   E   L   K      390
```

FIG. 4B

```
(SEQ ID NO. 1)
CCC AGA TTG GGG GAG CAG GAG GTG ATA ACA CCT GAC TTC CAG GGT GAG GAT GAA CCT CTC GTA TCC AGT GGA GAA GAT GAA CCC CTA GAT TTG ACA AGG   1336
 P   R   L   G   E   Q   E   V   I   T   P   D   F   Q   G   E   D   E   P   L   V   S   S   G   E   D   E   P   L   D   L   T   R     420

ACA CAA GCA TCT CAG GAG ACG CTC GCC TCT ACC ATG GGT GGT CCA ACA GAA ACA CCC GTC CTT ACA GAT TCC ACG GGT   1426
 T   Q   A   S   Q   E   T   L   A   S   T   M   G   G   P   T   E   T   P   V   L   T   D   S   T   G    450

GTC CCC AGC CCC AGC AGC GTA GGA GTA GAC ATG GAC TCA GGC ACA GCC CCC ACC ACC ATG AGG AGG GGC   1516
 V   P   S   P   S   S   V   G   V   D   M   D   S   G   T   A   P   T   T   M   R   R   G    480

CGC TTT AAA GGG TTG CGA AAT GGT CGA CAC TTC CAG TTT CAG CCT TCT CCA GAA GCA GCC AGT GCC CAG CCT ATT CCC   1606
 R   F   K   G   L   R   N   G   R   H   F   Q   F   Q   P   S   P   E   A   A   S   A   Q   P   I   P    510

ACC CTG GAA GTT ACT GCT GAT GCT GCC ATG CAC CAG CCT CTG GAG AGT CAG CAG AGC CAC TGG CCT GCC ATT ATT CCC   1696
 T   L   E   V   T   A   D   A   A   M   H   Q   P   L   E   S   Q   Q   S   H   W   P   A   I   I   P    540

ACC AAT GAA GTG GAT GTG CCA CCA GCA CAC GGG CCA GCA GAT CAC AGC AAG TGG GTG AAG TCC CGG AGT CAC CCC   1786
 T   N   E   V   D   V   P   P   A   H   G   P   A   D   H   S   K   W   V   K   S   R   S   H   P    570

AGT ACT GTC CCG AGC ACT GAC ACT GAC AGT GGG CAT GGC GAT GAG TCA GCC CCT GGT GTG TCC AAG TCC ATT ATT CCA   1876
 S   T   V   P   S   T   D   T   D   S   G   H   G   D   E   S   A   P   G   V   S   K   S   I   I   P    600

AGT ACT GTC CCG AGC AGT GCT GAG GAG GCC CAG CAG GCA CAT TCC TCC CTA CAG GCC CTA TCA CCC CAC CAC CCT CCT   1966
 S   T   V   P   S   S   A   E   E   A   Q   Q   A   H   S   S   L   Q   A   L   S   P   H   H   P   P    630

TGG TTG CCC TCA GAA CCC GCT GTC CCC CAA AAA CTG TGG CTT CTG CCA AGC CCG AAT GTG GAT GGT GAT GGC   2056
 W   L   P   S   E   P   A   V   P   Q   K   L   W   L   L   P   S   P   N   V   D   G   D   G    660

CCA GAC TTC CCC ATT GTA GCC ATG CTT CGA GCC CGG GCT GTC GTC CCA GAA CAG GAA GAT GCA CCC CCA GAG ACC CCA   2146
 P   D   F   P   I   V   A   M   L   R   A   R   A   V   V   P   E   Q   E   D   A   P   P   E   T   P    690

CTC TCC CCA GCT TCT CCA CTC CCC CCC CTG GGC GCT GTC AGA CCT GAA CAG GCA GAG ATC GAG GGG ATC AGC ATG CAG   2236
 L   S   P   A   S   P   L   P   P   L   G   A   V   R   P   E   Q   A   E   I   E   G   I   S   M   Q    720

TTT CAG GCT GCT ATG ATG AGC AGC AGC GGA GAA CAG CAC TCC GGA GAC CAC GAA GCC AAT GTG ACA GAC GTG ATC GGC ATG   2326
 F   Q   A   A   M   M   S   S   S   G   E   Q   H   S   G   D   H   E   A   N   V   T   D   V   I   G   M   750

GCT GAC ACC AAG ATC CCC CAC TCT GGC TCT TTG GAC TGG CTC GAT TTG GAC CCT TCT GAT GCT ACC AGC TCC ATG   2416
 A   D   T   K   I   P   H   S   G   S   L   D   W   L   D   L   D   P   S   D   A   T   S   S   M    780

GGG ACT GAG TCT GGG GTC TTG GTC CAC TTG GAC CCT TTA CCA AGT CCA ACA TCA CAC CAG CAG CCC ACC TCG CTA CCA   2416
 G   T   E   S   G   V   L   D   M   V   L   A   T   N   L   P   G   Q   I   L   P
```

FIG. 4C (SEQ ID NO. 1)

```
CTG CCT GGC CAG GGA CTG GAC ACT GGC TCC CAG CAT GGA GTA ACC ATG AGT GTG GAA CCT ACA GTG GCT TTG      2506
 L   P   G   Q   G   L   D   T   G   S   Q   H   G   V   T   M   S   V   E   P   T   V   A   L       810

GAA GGA GGT GCC ACC AAA GAC CCA ATG GAG GCC CCC ATG GAT GTC ACT GTT CAT GCC CCC TCG GTG TCT GAA CCC AAA AGT      2596
 E   G   G   A   T   K   D   P   M   E   A   P   M   D   V   T   V   D   A   P   S   V   S   E   P   K   S       840

TCC ATT TCT AGC ACC CAT GTG GTT GCT GTG ACT GTG ACC CCT ACA ACA AGC TCT GAA GGT GCC CAG GTG GTG TCC      2686
 S   I   S   S   T   H   V   V   A   V   T   V   T   P   T   T   S   S   E   G   A   Q   V   V   S       870

GCC CAG TCA CTG GGA ACC CTC GTT CCT CAT CCC AGT ATG GAC GAA GTG GCC TCG GTT GTG GCT      2776
 A   Q   S   L   G   T   L   V   P   H   P   S   M   D   E   V   A   S   V   V   A       900

TCA GGA GAA CCC ACA AGG TTG TGG GAC ATC CCC ATA CCT CTG TCC TTG GAT GAA TCA CTG AAG GTT CTG CAC      2866
 S   G   E   P   T   R   L   W   D   I   P   I   P   L   S   L   D   E   S   L   K   V   L   H       930

GAG AGC CCA GGC TTG GAG GGC TTC TGG GAA GAG GCC AGT GCC CCC ACG TGC CCC GAG AAC CCT TGT CTG CAC      2956
 E   S   P   G   L   E   G   F   W   E   E   A   S   A   P   T   C   P   E   N   P   C   L   H       960

GGG GGC ACC TGC CGC ACA AAT GGC CGC ATG TAC TGT AGT TGT GAT CAG GGG TAT GCT GGG GAG AAT TGT CAA ATT GAC      3046
 G   G   T   C   R   T   N   G   R   M   Y   C   S   C   D   Q   G   Y   A   G   E   N   C   Q   I   D       990

TGC TTG TGC AGC CCT GAG TGT GTG AAT GGG GGT ACC TGT ATT GAT GAG GTG AAT TTC TTC ATC TGC CTC TGT CCC CCC AGC ATT GGG GGC      3136
 C   L   C   S   P   E   C   V   N   G   G   T   C   I   D   E   V   N   F   F   I   C   L   C   P   P   S   I   G       1020

TGC TGA GAG AAG GAC ACA GAA ATT GAT TGC GAC TGG GGT CAC AAA TTC CAG TAC CGG CAC TGT CAT CGG AGA AAC AGT TTT GGA      3226
 C   *   E   K   D   T   E   I   D   C   D   W   G   H   K   F   Q   Y   R   H   C   H   R   R   N   S   F   G       1050

GAG GCA AGA GAC TGC CGG AGG CGA CGG CCA TCC CAA GAG GTC ACA GCC CAC CTG ACA GTA GAG GAG AAC AGT GAG AAC TGG      3316
 E   A   R   D   C   R   R   R   P   S   Q   E   V   T   A   H   L   T   V   E   E   N   S   E   N   W       1080

CAC GAG AAT TCA TGG ATT GGC CTG GAC ATG GCG TTC CAG GAC ACA CAA TAT GAG AAC TGG      3406
 H   E   N   S   W   I   G   L   D   M   A   F   Q   D   T   Q   Y   E   N   W       1110

AGA GAG AAG CAG CCG GAT AAT TTC TTC GCA GGT GTG TGT GAT GAG GAT GTC CCC      3496
 R   E   K   Q   P   D   N   F   F   A   G   V   C   D   E   D   V   P       1140
```

FIG. 4D (SEQ ID NO. 1)

```
TGT AAC TAC AAC CTC CCC TAC GTC TGC AAG AAG GGT ACA GTG CTG TGT GGG CCC CCT CCA GCA GTG GAG AAT GCC TCT CTT GTT GGT GTG    3586
 C   N   Y   N   L   P   Y   V   C   K   K   G   T   V   L   C   G   P   P   P   A   V   E   N   A   S   L   V   G   V    1170

CGC AAG GTC ATC GAG AAG TAC AAT GTC CAT GCC ACT GTG CGA TAC CAG TTC TCC CAG CAC GTG CAC CAT GCT GTG CGA TGC CGA             3676
 R   K   V   I   E   K   Y   N   V   H   A   T   V   R   Y   Q   F   S   Q   H   V   H   H   A   V   R   C   R             1200

AGC AAT GGG AAG AAG TGG GAC CGG CCT CAG ATT GTG TGC CGG ATG CGT CAT CGA GAA GGG CCA TCA CAT CAC CAC CAC CAC CAC CGG         3766
 S   N   G   K   K   W   D   R   P   Q   I   V   C   R   M   R   H   R   E   G   P   S   H   H   H   H   H   H   R         1230

CAT CAC AAG CCA CGC AAG GAG GAT CAC AGA AAA CAC TGC GCG AAA GAT GAA GGG TTC TGC TAA CGA TCC                                 3856
 H   H   K   P   R   K   E   D   H   R   K   H   C   A   K   D   E   G   F   C   *                                         1257

AGA CTA ATC AAG CAC CAC CCA GCT CCC CTG CAG AGC ATT GAC AAC CAG GTC GAC CAC AGG GGT GGG GAC                                 3946
ACC CTG GAG CCT GAG ACC CAC GTC CCT GCT CTG CAG TAC CTT ACT AGG GTC CTG GCA GGG GTG                                         4036
GCG GGA TCC CCA AGG CCA AGG CCA TGG TCT GGC ATT AGG GCC CTT TCA GGA GTC AAG TCG TAA TCC ATG ATG AGG                         4126
GGC AAA CAG TAT GTC TGT GTA CTG GTA AGT GGA AGA CAA CCA GAG ACT TTC ACT GAA TCC ATG GCA                                     4216
AAC CTT TGG CCC TCA AAG CTG TCA CTG TTG AAG GTG TGC TCC CCA ATG CCC TGG GAT CCC CTA AGG GCA GGC                             4306
TTC CAT GTC TTT CTT AAG CTC CTT TCC CTT GCC CAC CTC TCA GGA CTG CAT AGA ACA CTA GGC TGG TGC TGA ACT                         4396
GAC TAT TGT AGA AGG ATG TGC CAT CAC ATG GCC ACC ATG GCA GTC CCT CAG GTT ATT TAG TGT TCT ATA                                 4486
CCA GCG CTG GGC TCT GTC CTT CCC TAC GAG GCA CTG GGT CCT GTT GGG GAG GGC CTC ACT GTG CAG CTC                                 4576
TTG AAT TTT AGT GAT CGT AAT TTG AGA CAG AGC ATT GGG AGA CAG CTC TCT AGT TAT GCC CAG CCT                                     4666
GCT GAC TCC CCA CTA GTG CAG CCC TGA CGA GGA ATC CTT TGC GAT CAG AGC AGC AGC TGA                                             4756
CTG CTG GCC TGG AAC CTG TTA ACC TAT CTC TAT AGC CCA TGG GTT TGT GTG ACC CAT GTG TCC AGA CGT AAG ACA GAG                     4846
TCT TTT GTT TTA CTG ACC ATC ACT TGT GGT GTG TGA TCT CAC CCT CAA CGT GAG AGC AGC                                             4936
GGT GAC AGG GTA GAT GCT CTA ACG GCT CAG GGA GGA TCT CAG ACC ATG CGG CCA                                                     5026
TAG AGT AGT CAG CAG GTA AAA CCC AGC ATC CCT CAG GAT CTC CGG ATC CCG TGA GAG                                                 5116
CTA ACC CAG AGC CTG TCT TTA CTA                                                          GAA TTC                             5191
```

FIG. 7

```
161 FHYRAARDRYALTFAEAQEACHLS SATI AAPRHLQAA FEDGFDNCDAGW              209   SEQ. ID No. 23
                     |||            |          |  ||
262 F  YVGPARR    LTLAGARALCQRQGAALASVGQLHLAWHEGLDQCDPGW              307   SEQ. ID No. 24
                     A    C          a        A    G   C    GW

** ** ** ***** *
210 LSDRTVRYPITQSRPGCYGDRSSLPGVRSY           GRRDPQELYD VYCF          253   SEQ. ID No. 25
                ||||                         ||||        ||
308 LADGSVRYPIQTPRRRCGGSA           PGVRTVYRFANRT GFPAPGARFDAYCF      355   SEQ. ID No. 26
    I D       p    r      C             Vr          g           C
```

FIG. 8

```
CS-372      E I P   S S G D E              SEQ. ID No. 27
CS-410      E P L V S S G E D E            SEQ. ID No. 28
cs-630          D G S P D                  SEQ. ID No. 29
cs-754          E S G V L D                SEQ. ID No. 30
cs-834      D A   T S G S E                SEQ. ID No. 31
cs-901    D E V A S V S S G E              SEQ. ID No. 32
CS-944          E E V A S G Q E D          SEQ. ID No. 33
```

FIG. 9

```
Gelsolin    LWVGTGASEAEKTGAQEL  LRVLRAQPVQVAEGS  EPDGFWEALGGKAA YRTSP    SEQ. ID No. 34
(604-655)      ||  : :  ||         : :  ||            ||  ||   :  |:|
IDI-PG      LWDI PST LI PVSLGLDESDLKV                 VAESPGLEG FWEEVASGQEDPTDP  SEQ. ID No. 35
(907-952)
```

FIG. 10

| | | SEQ. ID NO: |
|---|---|---|
| 679 | PVSFGAEDPE TPF QTTMAAPGEASHGSPEADS IEI EG I SSMQATKH | 36 |
| 725 | PI SGPWASLDSSN VTVNP VPSDAGI LGTESG VLDLPGS | 37 |
| 763 | PTSDGQATVDMV LATWLP LPGHGLDTGSQSTPMEAHGVTMS VE | 38 |
| 806 | PTVALEGG ATKDPMEATMDV VPS TVDATSGSEPKS SI SSTHVV V T | 39 |
| 852 | AAGDQGTPT L | 40 |
| 852 | PTSSEGQV VAQESLGT LTS LPS H | 41 |
| 885 | PWSSLAS SMDEVASV SSGEPT RLWDIPST LI | 42 |
| 916 | PVSLGLD ESD LKVVAESPGLE GFWEEVASGQED | 43 |

```
        P S G a  D       T   p P s         g
```

CLONING AND EXPRESSION OF NEUROCAN, A CHONDROITIN SULFATE PROTEOGLYCAN

This invention was made with government support under grants NS-09348 and NS-13876 awarded by the National Institutes of Health, and grant MH-00129 awarded by the National Institute of Mental Health. The government has certain rights in the invention.

This application is a continuation of application Ser. No. 07/922,911, filed Aug. 3, 1992, now abandoned.

BACKGROUND OF THE INVENTION

1. Field of the Invention

The invention relates to novel eukaryotic neurocan proteins, subunits thereof and nucleic acid encoding therefor, which are useful for providing soluble, biologically active heterologous proteins in hosts. The invention is further related to hosts transformed with this nucleic acid and methods for producing soluble heterologous proteins in hosts using such molecules.

2. Description of the Background Art

A large body of data implicates a family of receptors, the selectins (lectin-EGF-complement binding-cell adhesion molecules (LEC-CAMs)), in the initial interactions between leukocytes and vascular endothelia leading to lymphocyte homing, platelet binding, and neutrophil extravasation (Hallman et al., *Biochem. Biophys. Res. Comm.* 174:236–243 (1991); Lawrence and Springer, *Cell* 65:859–873 (1991); Luscinskas et al., *J. Immunol.* 142:2257–2263 (1989); Watson et al., *Nature*, 349:164–167 (1991); Watson et al., *J. Cell Biol.*, 115:235–243 (1991). L-selectin is involved in lymphocyte homing to peripheral lymph nodes. P-selectin participates in adhesion of activated platelets. E-selectin seems to facilitate T-cell infiltration at sites of cutaneous inflammation (Picker et al., *Nature*, 349:796–799 (1991); Shimizu et al., *Nature*, 349:799–802 (1991)). All three may be involved in neutrophil extravasation at sites of tissue damage or infection (Stoolman, *Cell*, 907–910 (1989). The cell surface expression of these three receptors is differentially regulated, and binding of one receptor may have significant effects on the expression of other selectins and on integrin adhesion receptors (Kuijpers et al., *J. Immunol.*, 147:1369–1376 (1991); Lo et al., *J. Exp. Med.*, 173:1493–1500 (1991); Spertini et al., *Nature* 349:691–694 (1991)).

The three known selectins, L-Selectin (leukocyte adhesion molecule-1 [LECAM-1], LAM-1, gp90MEL), E-Selectin (LECAM-2, endothelial-leukocyte adhesion molecule-1 [ELAM-1]), and P-Selectin (LECAM-3, GMP-140), each contains a domain with homology to calcium-dependent lectins (C-lectins), and EGF-like domain, and several complement binding protein-like (CBP) domains (Bevilacqua et al., *Science*, 243: 1160–1165 (1989); Johnston et al., *Cell*, 56:1033–1044 (1989); Lasky et al., *Cell*, 65:1045–1055 (1989); Tedder et al., *J. Exp. Med.*, 170:123–133 (1989)). Identification of the C-lectin domains has led to an intense effort to define carbohydrate ligands for these glycoproteins. There is now general agreement that E-Selectin recognizes NeuNAc α2-3 Gal β1-4 (Fuc α1-3) GlcNAc (sialyl-Lewis$^x$, or sLe$^x$) and related oligosaccharides (Berg et al., *J. Biol. Chem.*, 265:14869–14872 (1991); Berg et al., *J. Cell Biol.* 114:343–349 (1991); Lowe et al., *Cell*, 63:475–484 (1990); Phillips et al., *Science*, 250:1130–1132 (1990); Tiemeyer et al., *Proc. Nat'l Acad. Sci. U.S.A.*, 88:1138–142 (1991); Tyrrell et al., *Proc. Nat'l Acad. Sci. U.S.A.*, 88:10372–10376 (1991); Walz et al., *Science*, 250:1132–1135 (1990)). P-Selectin has been reported to recognize the Lewis$^x$ structure (Gal β1-4 (Fuc α1-3) GlcNAc) (Larsen et al., *Cell*, 63:467–474 (1990)) and/or sLe$^x$ (Polley et al., *Proc. Nat'l Acad. Sci. U.S.A.*, 88:6224–6228 (1991)); although other ligands are possible (Moore et al., *J. Cell. Biol.*, 112:491–499 (1991)). See Foxall et al., *J. Cell. Biol.*, 117:895–902 (May, 1992).

The recruitment of leukocytes from the blood is one of the most dramatic cellular responses to tissue damage and inflammation, and is central to the physiologic trafficking of lymphocytes. Leukocyte extravasation is exquisitely regulated in vivo by mechanisms of selective leukocyte-endothelial cell (EC) recognition, which can display extraordinary specificity in relation to the inflammatory stimulus, the stage of the inflammatory response, and the tissue site or organ involved. Examples include the almost exclusive attachment of eosinophils to venules in allergic reactions, the specific recruitment of neutrophils early in acute inflammation, and the tissue-selective interaction of lymphocyte subsets with high endothelial venules (HEVs) in organized lymphoid tissues.

Adhesion receptors (ARs) mediate and help direct leukocyte-EC interactions (Table I; reviewed in Springer, *Nature* 346:425–433 (1990); Pober and Cotran, *Transplantation* 50:537–544 (1990); Berg et al., *Vascular Adhesion Molecules, Cellular and Molecular Mechanisms of Inflammation*, Vol. 2, pp. 111–129 (1991)). Paradoxically, however, individual receptors often participate in multiple leukocyte-EC interactions that are quite independently regulated in vivo. For example, the vascular E-selectin (ELAM-1) binds both neutrophils and skin-homing memory T-cells, yet is thought to support selective recruitment of neutrophils during acute inflammation and of cutaneous memory T-cells during chronic inflammation in the skin (Picker et al., *Nature* 349:796–799 (1991), and references cited therein). Such observations cannot be explained by simple lock-and-key models of cell-cell recognition; and seem to require a more complex control of leukocyte-EC interactions in vivo.

A general model in which leukocyte-EC recognition is viewed as an active process requiring at least three sequential events. First, interaction is initiated by binding of constitutively functional leukocyte ARs to EC counterreceptors. In the best characterized examples, such primary adhesion is mediated by lectin-carbohydrate interactions involving leukocyte or vascular "selectins" and their cognate oligosaccharide ligands (see Table I). This initial adhesion is transient and reversible, unless followed by a second event (activation of the leukocyte by specific chemoattractant or cell contact) mediated signals capable of triggering secondary ARs whose function is activation dependent. Interaction of the activation-dependent AR with its EC counterreceptor, the third step, results in strong, sustained attachments completing the process of recognition. The best characterized activation-dependent ARs are heterodimeric integrins of the β2 (CD18) or β1 (CD29) classes. See Butcher, *Cell*, 67:1033–1036 (Dec., 1991).

TABLE I

| Leukocyte | Endothelium |
|---|---|
| Step 1. Primary Adhesion Pathways | |
| Lectin-Carbohydrate | |
| L-selection (L, N, M) | Lymph node addressin |
| CLA (smTL) | E-selectin (ELAM-1) |
| sialyl Lewis χ (N, M) | E-selectin |
| sialyl Lewis χ (N, M) | P-selectin (GMP140, CD62) |
| Other | |
| ? | Mucosal addressin |

TABLE I-continued

| Leukocyte | Endothelium |
|---|---|
| Step 2. Chemoattractant/Activating Factors | |
| Intercrine Family | |
| Interleukin-8 | (N, L) |
| hMGSA/GROα | (N) |
| Platelet factor 4 | (N, M) |
| RANTES | (mIL, M) |
| HuMIP-1α | (CD8+ TL, BL) |
| HuMIP-1β | (vIL, ?M) |
| I-309 | (M) |
| Monocyte chemoattractant protein-1 | (M) |
| Others | |
| Lipids | |
| Platelet activating factor | (N) |
| Leukotriene B4 | (N, M) |
| Others | |
| Other Chemoattractants | |
| C5a | (N) |
| Formyl peptides | (N, M) |
| Interleukin-2 | (sTL) |
| Cell Contact-Mediated | |
| E-selectin binding | (N) |
| CD44 | (L) |
| Step 3. Activation-Dependent Adhesion Pathways | |
| Integrins | |
| LFA-1 (αLβ2) (L > N, M) | ICAM-1, ICAM-2 |
| Mac-1 (αMβ2) (N, M, sL) | ICAM-1, others |
| p150, 95 (αχβ2) (N, M, sL) | ? |
| VLA-4 (α4β1) (M, mL > vL) | VCAM-1 |

See Butcher et al., *Cell*, 67:1033–1036 (Dec., 1991), which is entirely incorporated herein by reference.

A number of recent studies indicate that chondroitin sulfate proteoglycans are involved in modulating cell interactions in developing nervous tissue (Hoffman et al., 1988; Crossin et al., 1989; Perris and Johansson, 1990; Margolis et al., 1991; Perris et al., 1991; Snow et al., 1991; Brittis et al., 1992) and are components of astroglial axon barriers (Snow et al., 1990a,b; McKeon et al., 1991; Oakley and Tosney, 1991). (The references cited herein by author and year are listed in the references section presented herein before the claims section.)

These findings indicate that extracellular chondroitin sulfate proteoglycans may act as repulsive molecules which modulate cell-cell and cell-matrix interactions by providing a mechanism for diminishing adhesive forces, thereby permitting cell rounding, division, differentiation, and cell movement in developing brain, and indicate the need for information on their primary structures, which will permit more detailed functional studies including work aimed at exploring the roles of specific protein domains.

Accordingly, there is a need to provide biologically active polypeptides having activities related to cell adhesion, leukocyte-endothelial cell recognition and differentiation and development of nervous tissue.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

It is an object of the present invention to overcome one or more of the deficiencies of the related art.

It is another object of the present invention to provide a neurocan polypeptide, as described herein.

It is another object of the present invention to provide non-naturally occurring synthetic, isolated and/or recombinant neurocan polypeptides which are fragments, consensus fragments and/or sequences having conservative amino acid substitutions, of at least one functional domain of a neurocan polypeptide, which polypeptides have been discovered to have several biological activities, including, but not limited to cell-adhesion, leukocyte-endothelial cell (EC) recognition, tissue-related inflammation, allergies, cellular and/or humoral hypersensitivity, trauma, neuronal development and cell transport, and/or infection.

It is yet another object of the present invention to provide synthetic or recombinant neurocan polypeptides, conservative substitution derivatives thereof, antibodies, anti-idiotype antibodies, compositions and methods that may be used as potential modulators of cell-adhesion, leukocyte-endothelial cell (EC) recognition, tissue-related inflammation, allergies, cellular and/or humoral hypersensitivity, trauma and/or infection, due to their expected biological properties, which may be used in diagnostic, therapeutic and/or research applications.

It is a further object of the present invention is to provide synthetic, isolated or recombinant neurocan polypeptides which are designed to inhibit or mimic various proteins, including but not limited to lectins, CAMs, versicans, aggrecans or gelsolins, as receptor or effector types and subtypes.

According to one aspect of the present invention, a synthetic or recombinant neurocan polypeptide is provided that comprises a neurocan amino acid sequence of, e.g., 20 to 1300 amino acids, substantially corresponding to at least one neurocan functional domain, or fragment and/or consensus peptide thereof, of a neurocan, wherein at least 30, 50, 70, 80, 100, 110, 120, 130 or 140 amino acids are preferred. In a preferred embodiment, the polypeptide is (a) chemically synthesized and/or (b) obtained from a recombinant host cell or organism which expresses a recombinant nucleic acid encoding a neurocan polypeptide, as defined herein.

In another preferred embodiment, the neurocan functional domain is selected at least one of a versican-like, an aggrecan-like, an EGF-like, a lectin-like, a sialyl Lewis$^x$ binding-like, a selectin-like, a complement binding-like, a gelsolin-like, an actin-binding, axon-stimulating-like, a neuron-stimulating-like or a neural differentiation stimulating-like domain, respectively, of a neurocan protein. Such neurocan functional domains have at least an 60% homology to the corresponding domain, such as 60, 65, 70, 75, 80, 92, 94, 96, 98 or 99% homology or identities.

In another aspect of the present invention, a neurocan composition is provided, comprising a neurocan polypeptide, or a pharmaceutically acceptable ester, ether, sulfate, carbonate; malate, glucuronide or salt thereof, the composition further comprising a pharmaceutically acceptable carrier and/or diluent.

In still another aspect of the present invention, a method is provided for treating a subject suffering from a disease state involving a qualitative or quantitative pathological abnormality of cell adhesion or leukocyte-endothelial cell recognition or a biological molecule functionally associated therewith. Such biological molecule may be a membrane cytoplasmic protein, lipid, carbohydrate, saccharide, nucleoside or nucleotide mono-, di-, or tri-phosphate, an enzyme, a co-factor, a nucleic acid, a neurotransmitter, an ion, a carrier, a cell receptor, or any combination thereof.

In a preferred embodiment, a neurocan polypeptide may have LECCAM activity and the abnormality involves a leukocyte-endothelial cell recognition pathology, wherein the method comprises administering an effective leukocyte-endothelial cell recognition modulating amount of a neurocan polypeptide of the present invention. In another preferred embodiment, the neurocan polypeptide comprises a neurocan functional domain having at least one of an EGF-like domain, a lectin-like domain and a complement binding domain. The pathology may be an inflammatory, tissue damage, infectious pathology or an allergic reaction.

In another preferred embodiment, the neurocan composition is administered as a pharmaceutical composition to provide a neurocan polypeptide in an amount ranging from about 0.01 μg to 100 mg/kg, and also preferably, about 10 μg to 10 mg/kg. In another preferred embodiment, the administering is by oral, intravenous, intramuscular, parenteral or topical administration, including mucosal administration to the nasal mucosa or the oral mucosa, by aerosol, nebulizer or drop administration as non-limiting examples.

According to one aspect of the present invention, there is provided a neurocan polypeptide, comprising an amino acid sequence of 100 to 1257 amino acids substantially corresponding to SEQ ID NO:1.

In one embodiment, the amino acid sequence substantially corresponds to amino acids 951 to 1215 of SEQ ID NO:1 and wherein the polypeptide has in vitro sialyl Lewis$^x$ oligosaccharide binding activity.

In another embodiment, the amino acid sequence substantially corresponds to amino acids 951 to 1020, 1020–1150, or 1150–1215 of SEQ ID NO:1.

In another embodiment, the neurocan polypeptide has selectin biological activity, wherein the selectin is P-selectin, E-selectin or L-selectin.

In another embodiment, the neurocan polypeptide has epidermal growth factor biological activity and/or lectin biological activity, such as for C-lectin.

In another embodiment, the polypeptide has complement binding protein biological activity.

In another embodiment, the neurocan is mammalian neurocan, such as selected from murine, bovine, ovine, human, rat, porcine, equine, dog, cat, sheep, goat, or of the Class Mammalia.

In another embodiment, the amino acid sequence corresponds to FIG. 1 (SEQ ID NOS:2–8).

In further embodiment, the composition further comprises a drug selected from an anti-inflammatory drug or a drug for treating a cellular or humoral hypersensitivity.

According to still another aspect of the present invention, there is provided a method for treating a subject suffering from a pathology related to a condition involving leukocyte-endothelial cell recognition, comprising administering to the subject a therapeutically effective amount of a neurocan composition as described herein.

In one embodiment, the condition is selected from an allergic reaction, an inflammatory condition, tissue damage, or an injection.

In another embodiment, the condition is selected from a pathology relating to an inflammatory or immunohypersensitivity.

According to a further aspect of the present invention, there is provided a method for producing a neurocan polypeptide as presented herein, wherein the polypeptide is a recombinant polypeptide obtained from a recombinant host which expresses a heterologous nucleic acid encoding a neurocan polypeptide, comprising the steps of: providing a host comprising a recombinant nucleic acid encoding a neurocan polypeptide in expressible form; culturing the host under conditions such that the polypeptide is expressed in recoverable amounts; and recovering the polypeptide produced by the host.

In another embodiment, the method further comprises purifying the polypeptide. In another embodiment, the host is a bacteria or a eukaryotic cell. The eukaryotic cell may be a mammalian cell, an insect cell or a yeast cell.

According to another aspect of the present invention, there is provided a method for producing a neurocan polypeptide, comprising chemically synthesizing a neurocan polypeptide in recoverable amounts; and recovering the polypeptide or epitope binding domain which binds such an epitope.

According to still another aspect of the present invention, there is provided a method for isolating a neurocan polypeptide or a ligand that binds a neurocan polypeptide, comprising providing a bound support, the support being bound to a neurocan polypeptide, or an antibody, anti-idiotype antibody, or a fragment thereof; contacting a sample containing the a protein comprising a neurocan polypeptide, or the ligand that binds a neurocan polypeptide, to the bound support, such that the neurocan polypeptide containing protein or ligand is reversibly bound to the bound support; and recovering the protein or ligand that is attached to the bound support by dissociating the protein or ligand under conditions that cause elution or dissociation of the protein or ligand from the bound support.

According to another aspect of the present invention, there is provided an antibody, anti-idiotype antibody or a fragment of the antibody or anti-idiotype antibody, that specifically displays an epitope of a neurocan polypeptide.

According to a further aspect of the present invention, there is provided a diagnostic kit, comprising a receptacle containing a neurocan polypeptide.

According to a further aspect of the present invention, there is provided a diagnostic kit, comprising a receptacle containing at least one selected from an anti-neurocan polypeptide antibody, anti-idiotype antibody or a fragment of the antibody or anti-idiotype antibody.

Other objects of the invention will be apparent to skilled practitioners from the following detailed description and examples relating to the present invention.

BRIEF DESCRIPTION OF THE DRAWINGS

FIG. 1A–B. 1A. N-terminal amino acid sequences of the adult (150 kDa) 1D1 proteoglycan core glycoprotein (SEQ ID NO:2) (and of a proteolyzed 45 kDa species (SEQ ID NO:3) isolated in one case from adult brain), and of five peptides obtained by endoproteinase Lys-C (SEQ ID NO:4), endoproteinase Asp-N (SEQ ID NO:5), or CNBr treatment of the 150 kDa core glycoprotein (SEQ ID NO:6–8, respectively). Lower case letters represent amino acids which, although not clearly identified in these cycles from our peptide sequencing, were chosen for purposes of oligonucleotide primer design on the basis of homologous sequences in versican. Underlined sections of the peptide sequences indicate regions used for the design of oligonucleotide primers. 1B. Sequences of synthetic oligonucleotide PCR primers (SEQ ID NOS:9–10) prepared on the basis of the peptide sequences shown above.

FIG. 2A–B. 2A. N-terminal amino acid sequences of the 245 kDa core glycoprotein (SEQ ID NO:11) and of CNBr (SEQ ID NO:12) and endoproteinase Lys-C (SEQ ID NO:13) peptides derived uniquely from the early postnatal form of the 1D1 proteoglycan, and sequences of four tryptic peptides (SEQ ID NOS:14–17) derived from the 65 kDa endo Lys-C peptide. Underlined sections of the peptide sequences indicate regions used for the design of oligonucleotide primers. 2B. Sequences of synthetic oligonucleotide primers (SEQ ID NOS:18–22) for reverse transcription and PCR, prepared on the basis of the peptide sequences shown above and of previously obtained nucleotide sequences.

FIG. 3. Schematic diagram of two isolated cDNA clones of the adult brain 1D1 proteoglycan. The coding region is boxed and vertical arrows indicate the N-terminus of the 150 kDa 1D1 core glycoprotein. Restriction sites are indicated, and horizontal arrows represent sequencing reactions in the indicated directions. Domains of the coding region with high homology are patterned. Intron present in upper clone is indicated by the broken line, and the location of the PCR-amplified region used as a probe for cDNA library screening is indicated above the lower clone.

FIG. 4A–D. Nucleotide sequence (SEQ ID NO:1) and deduced amino acid sequence (SEQ ID NO:49) from neurocan core protein cDNA. The contiguous cDNA sequence determined from the overlapping clones of FIGS. 3 and 5 is shown, together with the translation of an open reading frame of 3771 residues. Potential N-glycosylation sites are indicated with filled triangles and potential threonine O-glycosylation sites with open triangles. Serine-glycine sequences representing the most likely chondroitin sulfate attachment sites are double underlined, and an RGDS sequence is indicated by a dotted underline. Peptides from which amino acid sequence data were obtained are underlined, and amino acid sequences used for the design of oligonucleotide primers for enzymatic amplification reactions are boxed. Dots below cysteine residues indicate a spacing consistent with that previously reported for proteins containing similar Ig-like, lectin-like, EGF-like, and hyaluronic acid-binding globular domains, and two cysteine residues which do not fit this pattern are indicated by asterisks.

FIGS. 1 and 4). The first vertical arrow (bold) indicates the N-terminus of the smaller, adult brain 1D1 proteoglycan core glycoprotein, and the second vertical arrow indicates the N-terminus of the 45 kDa core protein. The lower bar shows the distribution of methionine residues (M) and the origin of three CNBr peptides used for sequencing.

FIG. 7. Alignment of neurocan tandem repeat domains according to the pattern proposed for other hyaluronic acid-binding proteins (SEQ ID NOS:23–26) (Perkins et al., 1991). The 17 residues indicated below the sequences are identical in all repeats of the four sequenced link proteins, two aggrecans, and versican, as well as in neurocan. Capital letters indicate amino acids which are also conserved in PGP-1 and CD44, and asterisks indicate residues in the neurocan sequence which are homologous to those of the proposed 8A4 monoclonal antibody epitope of link protein (Neame et al., 1985).

FIG. 8. Comparison of potential chondroitin sulfate attachment sites in neurocan, with the most likely sites for the calculated three chondroitin sulfate chains indicated by capital CS at left. Numbers refer to serine attachment sites (S) CS-372 (SEQ ID NO:27); CS-410 (SEQ ID NO:28); cs-630 (SEQ ID NO:29); cs-754 (SEQ ID NO:30); cs-834 (SEQ ID NO:31); cs-901 (SEQ ID NO:32); and CS-944 (SEQ ID NO:33). The selection of potential attachment sites is based on the presence of a serine-glycine dipeptide which is preceded by at least one acidic amino acid (Bourdon et. al., 1987; Krueger et. al., 1990). Acidic amino acids on the C-terminal side of the SG-dipeptide, which may be of importance (Zimmermann and Ruoslahti, 1989), are also indicated in bold. The third site listed (cs-630(SEQ ID NO:29)) closely resembles the chondroitin sulfate attachment site in collagen IX (McCormick et. al., 1987).

FIG. 9. Alignment of sequences of human gelsolin (SEQ ID NO:34) (Kwiatkowski et al., 1986) with the neurocan core-protein 1D1 PG (907–952) (SEQ ID NO:35). The aligned sequences have an identity of 33% (I) and 56% homology (:), based on the Dayhoff PAM-250 matrix of evolutionary distance between amino acids (Schwartz and Dayhoff, 1979), with comparison values normalized to a mean of 0 (Gribskov and Burgess, 1986). I, indicates identical amino acids; :, comparison value >0.5; ., comparison value >0.10.

FIG. 10. Alignment of amino acids 679 to 947 (SEQ ID NOS:36–43). In the bottom line, amino acids appearing in five or more repeats are indicated by capital letters, and in three or four repeats by lower case letters.

DESCRIPTION OF THE PREFERRED EMBODIMENTS

Figure 5:
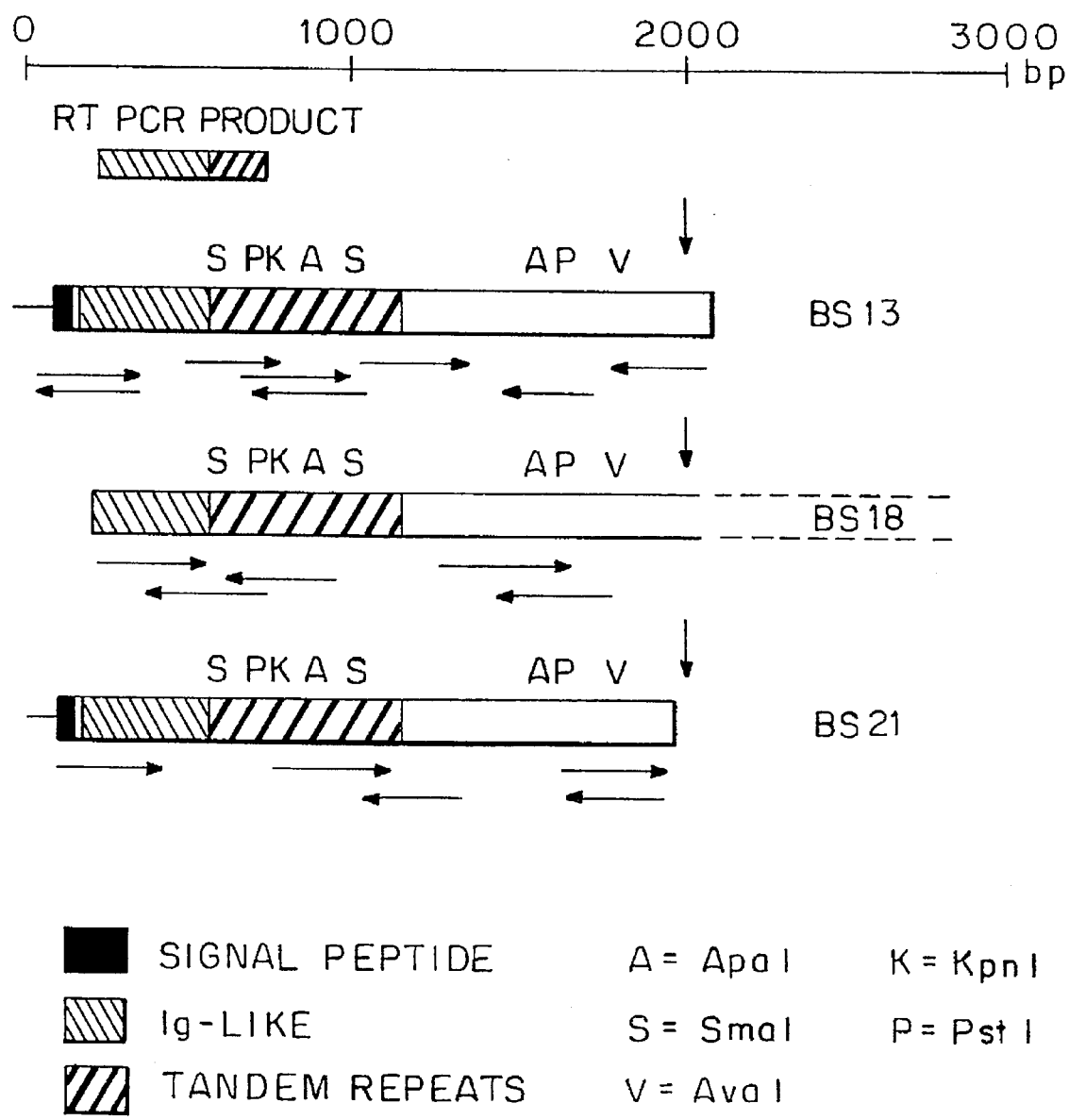
FIG. 5. Schematic diagram of three isolated cDNA clones of the early postnatal form of the 1D1 proteoglycan. The coding region is boxed, and vertical arrows indicate the N-terminus of the adult 1D1 proteoglycan core protein. Restriction sites are indicated, and horizontal arrows represent sequencing reactions in the indicated directions. Domains of the coding region with high homology are patterned. The location of the reverse transcription/PCR-amplified region used as a probe for cDNA library screening is indicated above the upper clone.

It has now been discovered that a neurocan protein or polypeptide, as an isolated naturally occurring sequence, or fragments or variants thereof, may be provided according to the present invention, as well as compositions comprising a neurocan polypeptide and methods of making and using thereof.

Non-naturally occurring synthetic, isolated and/or recombinant neurocan polypeptides of the present invention comprise fragments, consensus fragments and/or sequences having conservative amino acid substitutions, of at least one functional domain of a neurocan polypeptide, which polypeptides have been discovered, based on their cDNA sequence, to have several neurocan functional domains with known associated biological activities, including, but not limited to, ligand, effectors and/or receptors involved in cell-adhesion, leukocyte-endothelial cell (EC) recognition, tissue-related inflammation, allergies, cellular and/or humoral hypersensitivity, trauma, neuronal development and cell transport, and/or infection.

Neurocan polypeptides of the present invention can be synthesized or preferably recombinantly produced, and optionally purified, to provide commercially useful amounts of a neurocan polypeptide for use in therapeutic, diagnostic or research applications, according to known method steps. See, e.g., Ausubel et al, eds. Current Protocols in Molecular Biology, Wiley Interscience, N.Y., (1987, 1992); and Sambrook et al, Molecular Cloning, A Laboratory Manual, 2nd edition, Vols. 1–3, Cold Spring Harbor Press, (1989); Copsey and Delany, Genetically Engineered Human Therepeutic Drugs, MacMillan Publ., LTD, Stackton Press, N.Y., (1988); Schulz, G. E. et al., Principles of Protein Structure, Springer-Verlag, New York, 1978, and Creighton, T. E., Proteins: Structure and Molecular Properties, W. H. Freeman & Co., San Francisco, 1983, which references are herein entirely incorporated by reference.

Additionally, neurocan polypeptides according to the present invention can be used to generate polyclonal and/or monoclonal antibodies, anti-idiotype antibodies thereto, or fragments thereof, which may used for diagnostic and/or therapeutic applications according to known method steps. See, e.g., Harlow and Lane, Antibodies: A Laboratory Manual, Cold Spring Harbor Press (1988), which is herein entirely incorporated by reference.

Neurocan polypeptides, anti-neurocan antibodies or anti-idiotype antibodies (or fragments) thereof to neurocan polypeptides have been unexpectedly discovered to quantitatively or qualitatively modulate, as ligands, effectors, or receptor functional domains involved in cell-adhesion, leukocyte-endothelial cell (EC) recognition, tissue-related inflammation, allergies, cellular and/or humoral hypersensitivity, trauma and/or infection, neuronal development and cell transport, such that binding of neurocan polypeptides or anti-idiotype antibodies (or fragments) thereof to neurocans may be used for diagnostic research or therapeutic applications of the present invention.

Binding of such neurocan polypeptides, (including neurocan fragments, consensus peptides, substitution derivatives and antibodies) of the present invention may be used to treat symptoms of, and provide diagnosis and treatment for, pathologies related to the non-limiting examples of ligands, effectors or receptors involved in cell adhesion, leukocyte-endothelial cell recognition, cell interactions in developing nervous tissue, actin binding related to gelsolin binding of actin, hyaluronic acid binding, epidermal growth factors, sialyl Lewis$^x$ antigen binding, selectin activity, LEC-CAM activity, lectin-like activity, versican activity, aggrecan activity, cell secretion, axonal growth, and neuronal differentiation, and which may also modulate, quantitatively or qualitatively, ligand of effector or receptor binding to neurocans, aggrecans, versicans, gelsolins, lectins, LECCAMS, N-CAMs, I-CAMs, Ng-CAMs, or PECAMs.

A neurocan polypeptide of the present invention comprises at least one neurocan functional domain, which may include, but is not limited to a neurocan functional domain selected at least one of a versican-like, an aggrecan-like, an EGF-like, a lectin-like, a sialyl Lewis$^x$ binding-like, a selectin-like, a complement binding-like, a gelsolin-like, an actin-binding, axon-stimulating-like, a neuron-stimulating-like or a neural differentiation stimulating-like domain, respectively, of a neurocan protein. Such neurocan functional domains have at least an 60% homology to the corresponding domain, such as 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% homology or identity. For CAMS, see, e.g., Hardingham et al., FASEB J. 6:861–870 (1992), Rathjen et al, Semin. Neurosci. 3:271–284; Grumet et al., Curr. Opin. Neurobiol., 1:370–376; Grumet et al., Neurosci. Res.; 31:1–13 (1992); Edelman et al., Immun. Rev. 100:11–45 (1987); Edelman and Cunningham, Cold Spring Harbor Symposia on Quantitative Biology 55:303–318 (1990); Rutishauser, Semin. Neurosci., 3:265–270 (1991); Walsh and Doherty, Semin. Neurosci., 3:271–284 (1991); Burgoon et al., J. Cell Biol., 112:1017–1029; and Cunningham et al., Science, 236:799–806 (1987), which references are herein entirely incorporated by reference. Such pathologies have been found to correlate with symptoms occurring in inflammatory, allergic, infectious or tissue trauma pathologies.

As a non-limiting example, the use of synthetic or recombinant neurocan polypeptides of the present invention can be preferable to the use of known anti-inflammatory or allergy drugs that are used to treat inflammation using such drugs as steroid and non-steroid anti-inflammatory drugs, or for treating allergies, e.g., involving cellular or humoral hypersensitivity, as non-limiting examples. See, e.g., Berkow et al, eds., The Merck Manual, 15th editions Merck and Co., Rahway, N.J., 1987; Goodman et al., eds., Goodman and Gilman's The Pharmacological Basis of Therapeutics, 8th edition, Pergamon Press, Inc., Elmsford, N.Y., (1990); Avery's Drug Treatment: Principles and Practice of Clinical Pharmacology and Therapeutics, 3rd edition, ADIS Press, LTD., Williams and Wilkins, Baltimore, MD. (1987), Ebadi, Pharmacology, Little, Brown and Co., Boston, (1985), which references and references cited therein, are entirely incorporated herein by reference.

Such neurocan polypeptides of the present invention are expected to have significantly less side effects than presently used drugs used for treating such pathologies, as they occur naturally and/or modulate ligand binding involved in such physiological processes. Thus, neurocan polypeptides are expected to have reduced side effects attributable to known foreign compound drugs, with less immunogenicity, and reduced potential known side effects of known anti-inflammatory drugs or drugs known to be used for humoral or cellular hypersensitivity. Steroid anti-inflammatory agents can include corticosteroids, such as cortisone, prednisone, triamcinolone, dexamethasone, betamethasone, and related compounds, such as derivatives thereof and related compounds. Non-steroid anti-inflammatory agents may include salicylates or aspirin-like drugs, indomethacin and sulindac, propionic acid derivatives, pyrazolon derivatives, para-aminophenol derivatives, tolmetin, gold salts, and other known anti-inflammatory agents. See, e.g., Berker, supra, Goodman, supra, Avery, supra and Ebadi, supra, which are entirely incorporated herein by reference, included all references cited therein.

The present invention also includes the production, by chemical synthesis or recombinant DNA technology, of neurocan polypeptides, preferably as small as possible while still retaining sufficient functional activity of at least one particular neurocan functional domain as described herein, to modulate, such as to inhibit, or to enhance, binding to ligands, effectors or receptors of, e.g., CAMs, lectin, aggrecan, versican, gelsolin, selectin, ligands or receptors, or functional domains thereof, as non-limiting examples.

Such neurocan polypeptides of the present invention may include 10 to 1300 amino acid fragments, consensus sequences or substitution sequences thereof, which substantially correspond to SEQ ID NO:1 or to a selectin, a LECAM, CAM, a aggrecan, a versican, a lectin, a gelsolin or a functional domain thereof.

Accordingly, a "neurocan" or "neurocan polypeptide" of the present invention includes polypeptides having a "neurocan amino acid sequence" which substantially corresponds to a 10 to 1300 amino acid fragment and/or consensus sequence of SEQ ID NO:1 or a neurocan, wherein the neurocan polypeptide has homology of at least 80%, such as 81, 82, 83, 84, 85, 86, 87, 88, 89, 90, 91, 92, 93, 94, 95, 96, 97, 98, 99 or 100% homology to a portion of SEQ ID NO:1, while maintaining a neurocan functional activity, wherein a neurocan polypeptide of the present invention is not naturally occurring or is naturally occurring but is in a purified or isolated form which does not occur in nature.

Preferably, a neurocan polypeptide of the present invention substantially corresponds to at least one functional domain of a neurocan or more than one domain as a consensus sequence. Also preferred are neurocan polypeptides wherein the neurocan amino acid sequence is 10 to 1300 amino acids in length, such as 20, 30, 40, 50, 60, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 17, 180, 190, 200, 210, 220, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 262, 262, 263, 264, 265, 266, 267, 268, 269, 270, 271, 272, 273, 274, 275, 276, 278, 279, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 700, 800, 900, 1000, 1050, 1060, 1070, 1080, 1090, 110, 1110, 1120, 1130, 1140, 1150, 1160, 1170, 1180, 1190, 1200, 1210, 1211, 1212, 1213, 1214, 1215, 1216, 1217, 1218, 1219, 1220, 1225, 1230, 1235, 1240, 1241, 1242, 1243, 1244, 1245, 1246, 1247, 1248, 1249, 1250, 1251, 1252, 1253, 1254, 1255, 1256, 1257, 1258, 1259, 1260, 1265, 1270, 1280, 1290 or 1300 amino acids or any combination of 1, 2, 3, 4, 5, 6, 7, 8, 9, 10, 11, 12, 13, 14, 15, 16, 17, 18, 19 or more sequences thereof.

An amino acid or nucleic acid sequence of a neurocan polypeptide of the present invention is said to "substantially correspond" to another amino acid or nucleic acid sequence respectively, if the sequence of amino acids or nucleic acid in both molecules provides polypeptides having biological activity that is substantially similar, qualitatively or quantitatively, to the corresponding fragment of at least one neurocan functional domain.

Additionally or alternatively, such "substantially corresponding" neurocan sequences include conservative amino acid or nucleotide substitutions, or degenerate nucleotide codon substitutions wherein individual amino acid or nucleotide substitutions are well known in the art.

Alternatively or additionally, substantially corresponding refers to at least 80% homology or identity to an amino acid sequence of SEQ ID NO:1, such as 80, 81, 82, 83, 84, 85, 86, 87, 88, 89, 90, 91, 92, 93, 94, 95, 96, 97, 98, 99 or 100% homology or identity.

Accordingly, neurocan polypeptides of the present invention, or nucleic acid encoding therefor, include a finite set of substantially corresponding sequences as substitution peptides or polynucleotide which can be routinely obtained by one of ordinary skill in the art, without undue experimentation, based on the teachings and guidance presented herein. For a detailed description of protein chemistry and structure, see Schulz, G. E. et al., *Principles of Protein Structure*, Springer-Verlag, New York, 1978, and Creighton, T. E., *Proteins: Structure and Molecular Properties*, W. H. Freeman & Co., San Francisco, 1983, which are hereby incorporated by reference. For a presentation of nucleotide sequence substitutions, such as codon preferences, see Ausubel et al, supra, at §§A.1.1-A.1.24, and Sambrook et al, supra, at Appendices C and D.

Characteristics of Native Neurocan and cDNA

With regard to glycosylation and the moieties of native neurocan, the primary structure of native neurocan account for about 60% of its total molecular mass. Native neurocan also may contains 22% by weight of chondroitin sulfate and 20% of N- and O-glucosidically linked glycoprotein oligosaccharides including, in adult brain, a significant proportion of mannosyl-O-serine/threonine linked oligosaccharides (Rauch et al., 1991). The intact proteoglycan eluted from Sepharose CL-4B with buffer containing 4M guanidine HCl has a calculated molecular size of about 300 kDa, and after removal of the chondroitin sulfate chains by digestion with chondroitinase ABC, the resulting core glycoprotein has an apparent molecular size of 245 kDa as determined by SDS-PAGE under reducing conditions (Rauch et al., 1991). After allowing for the about 60 kDa contribution of glycoprotein oligosaccharides, the remaining 185 kDa is still considerably greater than would be expected for the 1235 amino acid mature core protein with a molecular mass of about 133 kDa encoded by a cloned cDNA. However, this discrepancy is consistent with the anomalously slow electrophoretic migration of glycosylated proteins due to decreased binding of SDS (Segrest and Jackson, 1972; Leach et al., 1980). Differences of this type between actual and apparent molecular sizes have been noted for the core proteins of other proteoglycans such as syndecan and versican, and for acidic proteins such as the neurofilament proteins (Kaufmann et al., 1984) and chromogranin A (Benedum et al., 1986; Iacangelo et al., 1986). For example, the core glycoprotein of chondroitinase/heparitinase digested syndecan and the nascent protein obtained by in vitro translation have apparent molecular sizes of 69 and 45 kDa, respectively, on SDS-PAGE, both of which are considerably larger than the 33 kDa calculated from the deduced amino acid sequence (Saunders et al., 1989), and the core proteins of versican isolated from fetal human fibroblasts migrate on SDS-PAGE as two bands with apparent molecular sizes of 490 and 560 kDa (Breuer et al., 1991), as compared to the calculated size of 265 kDa (Zimmermann and Ruoslahti, 1989).

Figure 11:
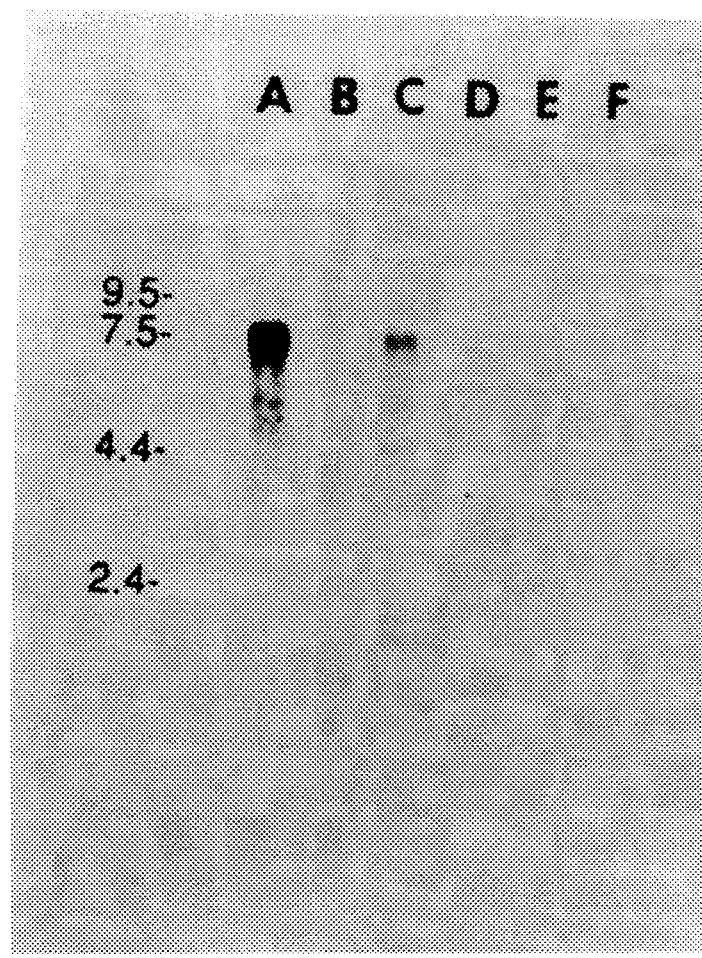
FIG. 11. Northern blot of mRNA from 4-day (A) and adult (C) rat brain, and from adult rat kidney (B), lung (D), liver (E), and muscle (F), electrophoresed on a 1% agarose gel containing 6% formaldehyde. 4 μg of RNA was used for 4-day brain, and 5 μg for all other samples. The blot was stained with alkaline phosphatase-labeled anti-digoxigenin antibodies as described under Experimental Procedures. The portion of the photographic print showing lanes B-F was exposed for a slightly longer period to reproduce the relative intensities of the bands from 4-day and adult brain seen on the original blot. Positions of RNA molecular size markers are indicated at the left.

The results of N-terminal microsequencing of the 150 kDa core protein from the adult brain proteoglycan together with our sequencing of two cDNA clones predicts a proteoglycan with a 619 amino acid core protein and a molecular mass of 67,449 Da. As in the case of the early postnatal form of the proteoglycan discussed above, the apparent molecular size of the adult 1D1 core glycoprotein is considerably greater than would be predicted from the cDNA sequence and carbohydrate composition. The 150 kDa core glycoprotein does not arise as a result of proteolysis during the isolation procedure, since there is a gradual developmental disappearance of the 245 kDa species which occurs even when the proteoglycans are isolated in the presence of protease inhibitors, and if chondroitin sulfate proteoglycans are isolated from a mixture of 7-day and adult brains which are homogenized together, approximately equal proportions of the 245 and 150 kDa core glycoproteins are found (Rauch et al., 1991). Northern blots of mRNA from 4-day and adult rat brain provided no evidence for developmentally regulated alternative splicing, insofar as only a single large transcript was detected both in early postnatal brain and at an age long after which the 245 kDa core glycoprotein has disappeared (FIG. 11). Because the N-terminal sequence of the adult brain proteoglycan has some characteristics of a signal peptide and is preceded by a methionine, it is possible that this represents a rare instance of utilization of an internal translation initiation site. The adult form of the 1D1 proteoglycan may be produced by a developmentally regulated in vivo proteolytic processing of the larger species predominant in early postnatal brain, and that the adult core protein is generated by endoproteolytic cleavage at the C-terminus of a methionine residue, similar to the cleavage of the amyloid β-protein precursor (Kang et al., 1987). It is possible that this developmentally regulated in vivo proteolytic cleavage of neurocan is related to the gradual appearance of intracellular (cytoplasmic and nuclear) chondroitin sulfate proteoglycans, hyaluronic acid, and link protein during later stages of brain development (Aquino et al., 1984a,b; Ripellino et al., 1988, 1989; Rauch et al., 1991). Elucidation of the primary structure of neurocan, as described herein, provides sufficient teaching and guidance to produce specific antibodies to neurocan polypeptide sequences of neurocan and to perform immunological in situ, in vivo and in vitro.

The presence of a hyaluronic acid-binding domain in neurocan is consistent with our previous demonstration that the 1D1 proteoglycan of early postnatal brain aggregates with hyaluronic acid (Rauch et al., 1991). However, we have recently determined that due to misidentification of an elution graph, there is no evidence for our earlier statement that the adult brain 1D1 proteoglycan also aggregates with hyaluronic acid. A 45 kDa link protein reactive with the 8A4 monoclonal antibody to rat chondrosarcoma link protein copurifies with the 1D1 proteoglycan isolated from either early postnatal or adult brain (Rauch et al., 1991). Since the adult form of the 1D1 proteoglycan does not have a conventional hyaluronic acid-binding region, the basis for the copurification of link protein with the adult proteoglycan species and its possible function remain unclear. It is apparently not due to the presence of small amounts of the early postnatal form of the proteoglycan in preparations of adult 1D1 proteoglycan, insofar as such preparations show no Coomassie Blue or antibody staining of a 245 kDa 1D1 core glycoprotein but the same degree of 8A4 immunoreactivity at 45 kDa as in equivalent amounts of early postnatal proteoglycan which have strong bands at 245 kDa.

The inventors of the present invention have previously identified in the chondroitin sulfate proteoglycans of brain both conventional O-glucosidically linked Gal(β1-3)GalNAc units and their mono- and disialyl derivatives, as well as a series of novel mannosyl-O-serine/threonine-linked oligosaccharides which can be released by mild alkaline borohydride treatment and have the sequence GlcNAc(β1-3)Manol at their proximal ends (Krusius et al., 1986, 1987). A significant proportion of free mannitol is also detected (Finne et al., 1979), reflecting the presence of individual O-glucosidically-linked mannose residues. The asparagine-linked oligosaccharides in the chondroltin sulfate proteoglycans of brain are almost exclusively of the tri- and tetraantennary types (for references, see Margolis and Margolis, 1989 which are also herein incorporated by reference).

Based on this information and the monosaccharide composition of the glycoprotein-type oligosaccharides present in native neurocan (Rauch et al., 1991), it is calculated that all of the six potential N-glycosylation sites may be occupied by tri- and tetraantennary oligosaccharides, although in adult brain the potential N-glycosylation site at Asn655 is presumably not always utilized, insofar as asparagine was detected at this position in our amino acid sequencing of the 150 kDa core glycoprotein (cf. FIGS. 1 and 4). Approximately 35 GalNAc-linked O-glucosidically linked oligosaccharides can also be accommodated in the deduced primary structure, and in adult brain, the proteoglycan may also contain two mannose-linked O-glycosidic oligosaccharides and up to six residues of free O-glucosidically linked mannose.

Figure 12:
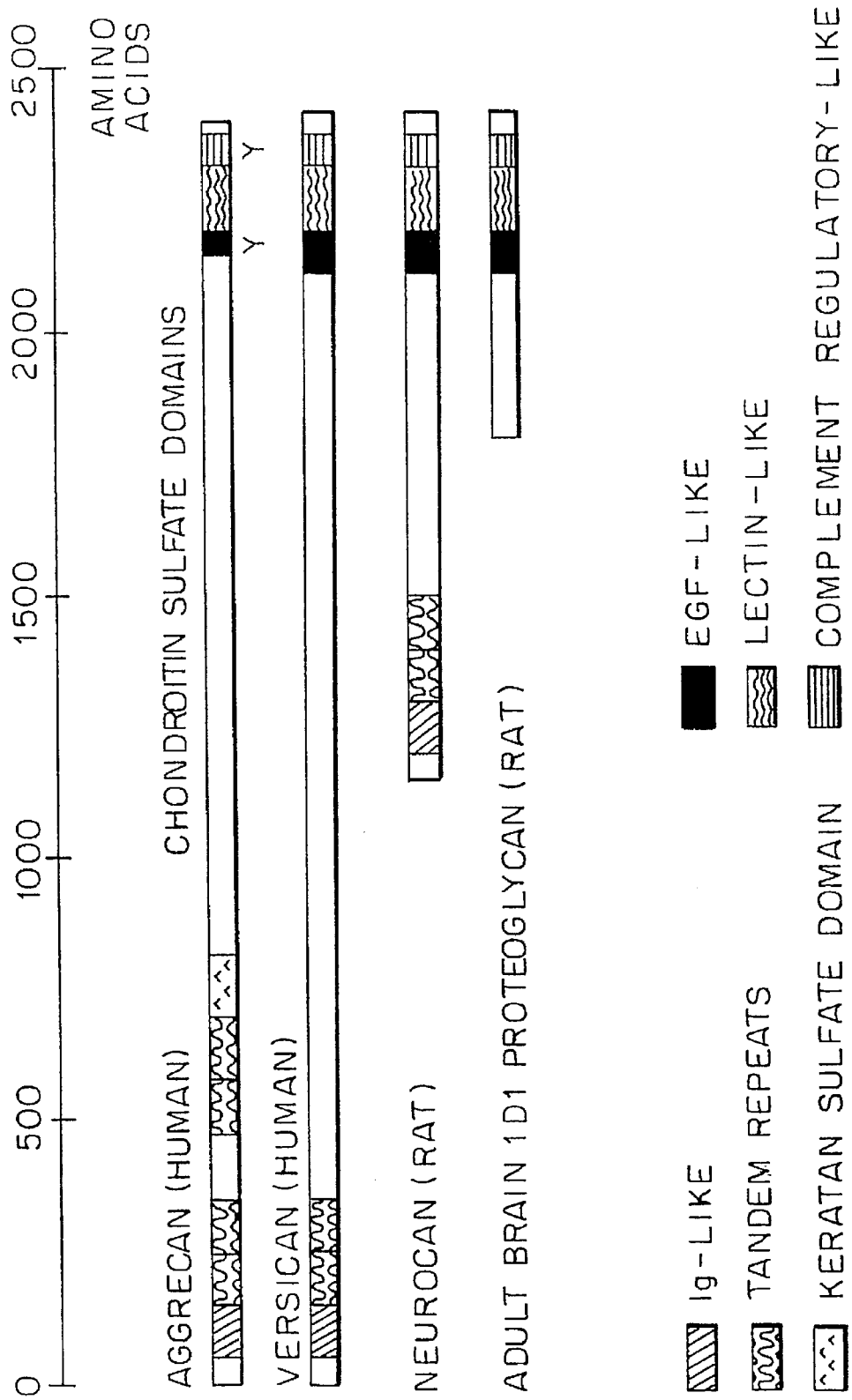
FIG. 12. Summary of the primary structures and homology domains of aggrecan, versican, and neurocan. Y indicates two aggrecan domains which may be deleted by alternative splicing (Doege et al., 1991).

In addition to sequence homologies with versican and aggrecan which are summarized in FIG. 12, all homologies found by a search of a protein data bank were within, e.g., the hyaluronic acid-binding region and EGF-like, lectin-like, or complement regulatory-like domains. Additionally, a homology to gelsolin was detected in search using only peptide sequences. The combination of a lectin-like domain followed by an EGF-like domain and a series of consensus repeats similar to those in complement regulatory proteins has also been found in three membrane proteins which are involved in leukocyte trafficking and recruitment to sites of inflammation by mediating their adhesion to endothelial cells, and in neutrophil and monocyte adhesion to activated platelets. Because of the domain arrangement in this family of cell adhesion molecules, they have been called LEC-CAMs (for a review, see Brandley et al., 1990). The carbohydrate ligand recognized by two of these proteins, endothelial cell-leukocyte adhesion molecule 1 (ELAM-1) and the leukocyte receptor CD62, which is expressed on activated platelets and endothelial cells, has been identified as Sia(a2-3)Gal(β1-4)(Fuc(a1-3))GlcNAc (sialyl-Lewis x; Polley et al., 1991).

Using an in vitro transcription and translation product it was also demonstrated that the lectin-like domain of the rat cartilage proteoglycan core protein has the ability to interact with carbohydrates. This product could be retarded on coles of immobilized fucose or galactose, whereas no interaction was observed with mannose and N-acetylglucosamine (Halberg et al., 1988). It is therefore expected that the lectin-like domains of neurocan and other proteoglycans recognize sialyl-Lewis x or related structures.

Neurocan has no structural similarities with the NG2 antigen, the only chondroitin sulfate proteoglycan of nervous tissue whose primary structure has been described (Nishiyama et al., 1991).

The RGDS sequence of neurocan (which occurs immediately after the second tandem repeat loop followed by a cysteine-free stretch of about 50 amino acids rich in acidic residues; FIG. 4) has a location similar to that of the functional RGD sequence in vitronectin, which closely follows the N-terminal cysteine-rich somatomedin B domain (Preissner, 1991). Searches for other known adhesive recognition sequences (Yamada, 1991) such as ones demonstrated in laminin, thrombospondin, collagen I, and the amyloid P component failed to reveal any of these sequences in neurocan.

It is interesting that there is some sequence similarity between a region of neurocan and gelsolin, a cytoplasmic, calcium-dependent, actin filament severing protein that is also a potent nucleator of actin assembly and blocks barbed ends of actin filaments (for a review, see Stossel et al., 1985). Gelsolin-like proteins have been isolated from neural and endocrine tissues (Sakurai et al., 1990), where they may be involved in both the regulation of calcium-dependent secretory processes by freeing secretory organelles such as synaptic vesicles from the cytoskeletal network (which prevents their movement in the resting state), as well as in axonal growth and neuronal differentiation by interaction with actin in growth cones. Another potentially interesting relationship of chondroitin sulfate proteoglycans of brain to the cytoskeleton is indicated by an earlier report that they act as endogenous inhibitors of a carboxypeptidase which catalyzes the release of C-terminal tyrosine residues from tubulin (Argarana et al., 1981). Neurocan polypeptides are expected play a role in cell regulatory processes through interactions with cytoskeletal and/or nuclear proteins.

Our immunocytochemical studies using the 1D1 monoclonal antibody have shown that neurocan is present in the subplate region of the developing mouse cerebral cortex in regions that were previously found to contain chondroitin sulfate and fibronectin (Sheppard et al., 1991). Based on correlations between the patterns of protein expression and axonal migration during development, is expected suggested that these molecules may play a role in defining a destination for migrating axons that form the cortical plate, and in delineating pathways for early axonal extension (Sheppard et al., 1991).

It has also been found that low concentrations (2–10 μg/ml) of both the intact 1D1 proteoglycans from both early postnatal (i.e., neurocan) and adult brain, as well as their core glycoproteins obtained by chondroitinase treatment, inhibit the homophilic binding of N-CAM and the neuron-glia cell adhesion molecule, Ng-CAM. Effects were observed both on the aggregation of fluorescent beads (Covaspheres) coated with the cell adhesion molecules and in studies on the attachment of neurons to Ng-CAM substrates, whereas in both types of assays much higher concentrations of rat chondrosarcoma chondroitin sulfate proteoglycan (aggrecan) or its core protein were without effect. It was additionally found that the core proteins of brain proteoglycans supported the binding of neurons. cDNA constructs used to express specific domains of neurocan and Ng-CAM are expected to show specific biological interactions of effectors, ligands and receptors relating to one or more neurocan functional domains.

Amino Acid Substitutions of Native Neurocan for a Neurocan Polypeptide. Conservative substitutions of a neurocan polypeptide of the present invention includes a variant wherein at least one amino acid residue in the polypeptide has been conservatively replaced by a different amino acid. Such substitutions preferably are made in accordance with the following list as presented in Table II, which substitutions may be determined by routine experimentation to provide modified structural and functional properties of a synthesized polypeptide molecule, while maintaining the receptor binding, inhibiting or mimicking biological activity, as determined by known neurocan receptor activity assays, as presented herein.

TABLE II

| Original Residue | Exemplary Substitution |
|---|---|
| Ala | Gly;Ser |
| Arg | Lys |
| Asn | Gln;His |
| Asp | Glu |
| Cys | Ser |
| Gln | Asn |
| Glu | Asp |
| Gly | Ala;Pro |
| His | Asn;Gln |
| Ile | Leu;Val |
| Leu | Ile;Val |
| Lys | Arg;Gln;Glu |
| Met | Leu;Tyr;Ile |
| Phe | Met;Leu;Tyr |
| Ser | Thr |
| Thr | Ser |
| Trp | Tyr |
| Tyr | Trp;Phe |
| Val | Ile;Leu |

Alternatively, another group of substitutions of neurocan polypeptides of the present invention are those in which at least one amino acid residue in the protein molecule has been removed and a different residue inserted in its place according to the following Table III. The types of substitutions which may be made in the protein or peptide molecule of the present invention may be based on analysis of the frequencies of amino acid changes between a homologous protein of different species, such as those presented in Table 1-2 of Schulz et al., supra and FIGS. 3–9 of Creighton, supra. Based on such an analysis, alternative conservative substitutions are defined herein as exchanges within one of the following five groups:

TABLE III

1. Small aliphatic, nonpolar or slightly polar residues:
   Ala, Ser, Thr (Pro, Gly);
2. Polar, negatively charged residues and their amides:
   Asp, Asn, Glu, Gln;
3. Polar, positively charged residues:
   His, Arg, Lys;
4. Large aliphatic, nonpolar residues:
   Met, Leu, Ile, Val (Cys); and
5. Large aromatic residues:
   Phe, Tyr, Trp.

The three amino acid residues in parentheses above have special roles in protein architecture. Gly is the only residue lacking any side chain and thus imparts flexibility to the chain. This however tends to promote the formation of secondary structure other than α-helical. Pro, because of its unusual geometry, tightly constrains the chain. It generally tends to promote β-turn-like structures, although in some cases Cys can be capable of participating in disulfide bond formation which is important in protein folding. Note the Schulz et al. would merge Groups 1 and 2, above. Note also that Tyr, because of its hydrogen bonding potential, has significant kinship with Ser, and Thr, etc.

Conservative amino acid substitutions according to the present invention, e.g., as presented above, are known in the art and would be expected to maintain biological and structural properties of the polypeptide after amino acid substitution. Most deletions and insertions, and substitutions according to the present invention are those which do not produce radical changes in the characteristics of the protein or peptide molecule. "Characteristics" is defined in a non-inclusive manner to define both changes in secondary structure, e.g. α-helix or β-sheet, as well as changes in physiological activity, e.g. in receptor binding assays.

However, when the exact effect of the substitution, deletion; or insertion is to be confirmed one skilled in the art will appreciate that the effect of the substitution or substitutions will be evaluated by routine screening assays, either immunoassays or bioassays to confirm biological activity, such as receptor binding or modulation of ligand binding to the corresponding neurocan. See, e.g., Maranges et al., eds., for example, a substituted polypeptide typically is made by site-specific mutagenesis of the peptide molecule-encoding nucleic acid, expression of the mutant nucleic acid in recombinant cell culture, and, optionally, purification from the cell culture, for example, by immunoaffinity chromatography using a specific antibody on a chemically derivatized column or immobilized membranes or hollow fibers (to absorb the mutant by binding to at least one epitope).

Neurocan Polypeptide having Consensus Sequence or Chemical Derivatives. A preferred use of this invention is the production, by chemical or recombinant DNA technology, of neurocan polypeptides, preferably as small as possible while still retaining at least one functional activity of a functional domain of neurocan. By production of neurocan polypeptides including smaller fragments or variants of such functional domains, one skilled in the art, using known binding and inhibition assays, can readily identify the neurocan polypeptides having at least one biological activity of a neurocan functional domain using known method steps.

Consensus peptides of neurocan polypeptides of the present invention may include peptides which are distinct from known selectin, EGF, CAM, versican, aggrecan, gelsolin, lectin, or complement binding proteins in critical structural features, but which are derived from consensus sequences and/or fragments of at least one of neurocan-functional domain of SEQ ID NO:1 or homologs thereof.

Such consensus peptides may be derived by molecular modeling, optionally combined with hydrophobicity analysis and/or fitting to model helices, as non-limiting examples. Such modeling can be accomplished according to known method steps using known modeling algorithms, such as, but not limited to, ECEPP, INSIGHT, DISCOVER, CHEM-DRAW, AMBER, FRODO and CHEM-X. Such algorithms compare neurocan functional domains as determinable and/or probable energy-miminized structures, and define alternative consensus neurocan polypeptide fragments.

Such consensus peptides or fragments of neurocans may then be synthesized or produced recombinantly, in order to provide neurocan polypeptides according to the present invention which mimic, modulate or inhibit binding of ligands, effectors or receptors of one or more neurocan functional domains. Neurocan ligands, effectors or receptors, in the context of the present invention, refer to biological molecules that interact with one or more bind neurocan functional domains, in vitro, in situ or in vivo, and may include glycoproteins, carbohydrates, polypeptides, hormones, neurotransmitters, viruses or receptor binding domains, thereof, of CAMs, lectins, selectins, aggrecans, versicans, gelsolins, nucleosides, nucleotides, coagulation cascade factors, odorants or pheromones, toxins, colony stimulating factor, platelet activating factors, neuroactive peptides, neurohumors, or any biologically active compounds, such as drugs or naturally occurring compounds.

In neurocan polypeptides of the present invention, one or more, preferably 4–10, Asp and/or Lys residues may additionally be incorporated at the carboxy and/or amino terminal ends in order to provide expected helix forming effects of the helix dipole effect, e.g., as described in Baldwin et al Biochem. 28:2130 (1989); Baldwin et al Proc. Nat'l Acad. Sci. U.S.A. 84:8898 (1987); and Baldwin et al Proc. Nat'l Acad. Sci. USA 86:5286 (1989), which references are entirely incorporated herein by reference.

As a non-limiting example of neurocan polypeptides of the present invention, the LECCAM-like domain of a neurocan as amino acids 951–1215 of SEQ ID NO:1 or a 30–264 amino acid sequence substantially corresponding to at least one of amino acids 951–1020 (EGF-like domain); 1020–1150 (Lectin-like); and 1150–1215 (Complement-binding domain) of SEQ ID NO:1. Additionally or alternatively, a consensus sequence of one or more neurocan functional domains may be used.

In the context of the present invention, neurocan polypeptides of greater than 50 amino acids are preferred such that a neurocan polypeptide may span the lipid bilayer.

Additionally, modified amino acids or chemical derivatives of amino acids of consensus or fragments of neurocans proteins, according to the present invention may be provided, which polypeptides contain additional chemical moieties or modified amino acids not normally a part of the protein. Covalent modifications of the peptide are thus included within the scope of the present invention. Such modifications may be introduced into a neurocan polypeptide by reacting targeted amino acid residues of the polypeptide with an organic derivatizing agent that is capable of reacting with selected side chains or terminal residues. The following examples of chemical derivatives are provided by way of illustration and not by way of limitation.

Aromatic amino acids may be replaced with D- or L-naphylalanine, D- or L-phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole (alkyl)alanines, and D- or L-alkylalanines where alkyl may be substituted or unsubstituted methyl, ethyl, propyl, hexyl, butyl, pentyl, iso-propyl, iso-butyl, sec-isotyl, iso-pentyl, non-acidic amino acids, of C1-C20.

Acidic amino acids can be substituted with non-carboxylate amino acids while maintaining a negative charge, and derivatives or analogs thereof, such as the non-limiting examples of (phosphono)-alanine, glycine, leucine, isoleucine, threonine, or serine; or sulfated (e.g., —$SO_3H$) threonine, serine, tyrosine.

Other substitutions may include unnatural hyroxylated amino acids may made by combining "alkyl" (as defined and exemplified herein) with any natural amino acid. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage in any of neurocan polypeptides can be replaced by a ketomethylene moiety, e.g. (—C(=O)—CH₂—) for (—(C=O)—NH—). Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

In addition, any amino acid representing a component of the said peptides can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D- amino acid but which can additionally be referred to as the R- or the S-, depending upon its composition and chemical configuration. Such derivatives have the property of greatly increased stability to degradation by enzymes, and therefore are advantageous in the formulation of compounds which may have longer in vivo half lives, when administered by oral, intravenous, intramuscular, intraperitoneal, topical, rectal, intraocular, or other routes.

Additional amino acid modifications of amino acids of neurocan polypeptides of to the present invention may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo- beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5–7.0 because this agent is relatively specific for the histidyl side chain, and para-bromophenacyl bromide may also be used; e.g., where the reaction is preferably performed in 0.1M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alpha-amino-containing residues include compounds such as imidoesters/ e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents; among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well-known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'-N-C-N-R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

Derivatization with bifunctional agents is useful for cross-linking the peptide to a water-insoluble support matrix or to other macromolecular carriers, according to known method steps. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 (which are herein incorporated entirely by reference), may be employed for protein immobilization.

Other modifications of neurocan polypeptides of the present invention may include hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecule Properties*, W. H. Freeman & Co., San Francisco, pp. 79–86 (1983)), acetylation of the N-terminal amine, methylation of main chain amide residues (or substitution with N-methyl amino acids) and, in some instances, amidation of the C-terminal carboxyl groups, according to known method steps.

Such derivatized moieties may improve the solubility, absorption, permeability across the blood brain barrier biological half life, and the like. Such moieties or modifications of neurocan polypeptides may alternatively eliminate or attenuate any possible undesirable side effect of the protein and the like. Moieties capable of mediating such effects are disclosed, for example, in *Remington's Pharmaceutical Sciences*, 16th ed., Mack Publishing Coo, Easton, Pa. (1980).

Such chemical derivatives of neurocan polypeptides also may provide attachment to solid supports, including but not limited to, agarose, cellulose, hollow fibers, or other polymeric carbohydrates such as agarose, cellulose, such as for purification, generation of antibodies or cloning; or to provide altered physical properties, such as resistance to enzymatic degradation or increased binding affinity or modulation for neurocans, which is desired for therapeutic compositions comprising neurocan polypeptides, antibodies thereto or fragments thereof. Such peptide derivatives are well-known in the art, as well as method steps for making such derivatives using carbodiimides active esters of N-hydroxy succinimide, or mixed anhydrides, as non-limiting examples.

Variation upon consensus peptide sequences of neurocan polypeptide of the present invention may also include: the addition of one, two, three, four, or five lysine, arginine or other basic residues added to the —COOH terminal end of the peptide; and/or one, two, three, four, or five glutamate or aspartate or other acidic residues added to the amino terminal end of the peptide, where "acidic" and "basic" are as defined herein. Such modifications are well known to increase the α-helical content of the peptide by the "helix dipole effect". They also can provide enhanced aqueous solubility of the peptide. See, e.g., Baldwin et al., supra.

Antibodies of the Present Invention Relating to Neurocan Polypeptides. This invention is also directed to an antibody which binds an epitope specific for a neurocan polypeptide of the present invention and the use of such an antibody to detect the presence of, or measure the quantity or concentration of, a neurocan in a cell, a cell or tissue extract, a biological fluid, an extract thereof, a solution, or sample, in vitro, in situ, or in vivo.

The term "antibody" is meant to include polyclonal antibodies, monoclonal antibodies (mAbs), chimeric antibodies, anti-idiotypic (anti-Id) antibodies to antibodies specific for a neurocan polypeptide of the present invention, as well as fragments thereof.

Polyclonal antibodies are heterogeneous populations of antibody molecules derived from the sera of animals immunized with an antigen.

A monoclonal antibody contains a substantially homogeneous population of antibodies specific to antigens, which population contains substantially similar epitope binding sites. MAbs may be obtained by methods known to those skilled in the art. See, for example Kohler and Milstein, *Nature* 256:495–497 (1975); U.S. Pat. No. 4,376,110; Ausubel et al., eds., *Current Protocols in Molecular Biology*, Wiley Interscience, N.Y., (1987, 1992); and Harlow and Lane *Antibodies: A Laboratory Manual* Cold Spring Harbor Laboratory (1988), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of mAbs in vivo or in situ makes this the presently preferred method of production.

Chimeric antibodies are molecules different portions of which are derived from different animal species, such as those having variable region derived from a murine mAb and a human immunoglobulin constant region, which are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al, *Proc. Natl. Acad. Sci. U.S.A.* 81:3273–3277 (1984); Morrison et al., *Proc. Natl. Acad. Sci. U.S.A.* 81:6851–6855 (1984); Boulianne et al., *Nature* 312:643–646 (1984); Cabilly et al., *European Patent Application* 125023 (published Nov. 14, 1984); Neuberger et al., *Nature* 314:268–270 (1985); Taniguchi et al., *European Patent Application* 171496 (published Feb. 19, 1985); Morrison et al., *European Patent Application* 173494 (published Mar. 5, 1986); Neuberger et al., *PCT Application* WO 86/01533, (published Mar. 13, 1986); Kudo et al., *European Patent Application* 184187 (published Jun. 11, 1986); Morrison et al., *European Patent Application* 173494 (published Mar. 5, 1986); Sahagan et al., *J. Immunol.* 137:1066–1074 (1986); Robinson et al., *International Patent Publication No.* PCT/US86/02269 (published May 7, 1987); Liu et al., *Proc. Natl. Acad. Sci. U.S.A.* 84:3439–3443 (1987); Sun et al., *Proc. Natl. Acad. Sci. U.S.A.* 84:214–218 (1987); Better et al., *Science* 240:1041–1043 (1988); and Harlow and Lane *Antibodies: A Laboratory Manual* Cold Spring Harbor Laboratory (1988)). These references are incorporated entirely herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody my also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against a neurocan polypeptide of the present invention may be used to induce anti-Id antibodies in suitable animals, such as BALB/c mice. Spleen cells from such immunized mice are used to produce anti-Id hybridomas secreting anti-Id mAbs. Further, the anti-IdmAbs can be coupled to a immunogenic carrier such as keyhole limpet hemocyanin (KLH) or cationized bovine serum albumin and used to immunize additional BALB/c mice. Sera from these mice will contain anti-anti-Id antibodies that have the binding properties of the original mAb specific for a neurocan polypeptide epitope.

The anti-Id mAbs thus have their own idiotypic epitopes, or "idiotopes" structurally similar to the epitope being evaluated, such as a neurocan lectin domain.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of a neurocan polypeptide according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

The antibodies, or fragments of antibodies, useful in the present invention may be used to quantitatively or qualitatively detect a neurocan polypeptide in a sample or to detect presence of cells which express a neurocan polypeptide of the present invention. This can be accomplished by immunofluorescence techniques employing a fluorescently labeled antibody (see below) coupled with light microscopic, flow cytometric, or fluorometric detection.

The antibodies (of fragments thereof) useful in the present invention may be employed histologically, as in immunofluorescence or immunoelectron microscopy, for in situ detection of a neurocan polypeptide of the present invention. In situ detection may be accomplished by removing a histological specimen from a patient, and providing the a labeled antibody of the present invention to such a specimen. The antibody (or fragment) is preferably provided by applying or by overlaying the labeled antibody (or fragment) to a biological sample. Through the use of such a procedure, it is possible to determine not only the presence of a neurocan polypeptide but also its distribution on the examined tissue. Using the present invention, those of ordinary skill will readily perceive that any of a wide variety of histological methods (such as staining procedures) can be modified in order to achieve such in situ detection.

Such assays for a neurocan polypeptide of the present invention typically comprise incubating a biological sample, such as a biological fluid, a tissue extract, freshly harvested cells such as lymphocytes or leukocytes, or cells which have been incubated in tissue culture, in the presence of a detectably labeled antibody capable of identifying a neurocan polypeptide, and detecting the antibody by any of a number of techniques well-known in the art, see, e.g., Harlow and Lane, supra; Ausubel et al, supra; and Sambrook et al, supra.

The biological sample may be treated with a solid phase support or carrier, such as nitrocellulose, or other solid support or carrier which is capable of immobilizing cells, cell particles or soluble proteins. The support or carrier may then be washed with suitable buffers, followed by treatment with a detectably labeled neurocan polypeptide-specific antibody. The solid phase support or carrier may then be washed with the buffer a second time to remove unbound antibody. The amount of bound label on said solid support or carrier may then be detected by known method steps, see, e.g., Harlow, supra; Ausubel, supra; or Sambrook, supra.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, or cylindrical, as in the inside surface of a test tube, or the external surface of a rod. Alternatively, the surface may be flat such as a sheet, polymer test strip, etc. Preferred supports or carriers include polystyrene beads. Those skilled in the art will know many other suitable carriers for binding antibody or antigen, or will be able to ascertain the same by use of routine experimentation.

The binding activity of a given lot of anti-neurocan polypeptide antibody may be determined according to well known method steps. Those skilled in the art will be able to determine operative and optimal assay conditions for each determination by employing routine experimentation, see, e.g., Harlow, supra.

Other such steps as washing, stirring, shaking, filtering and the like may be added to the assays as is customary or necessary for the particular situation.

One of the ways in which a neurocan polypeptide-specific antibody can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards. See, Harlow, supra, Ausubel, supra.

Detection may be accomplished using any of a variety of other immunoassays. For example, by radioactivity labeling the antibodies or antibody fragments, it is possible to detect R-PTPase through the use of a radioimmunoassay (RIA). A good description of RIA maybe found in *Laboratory Techniques and Biochemistry in Molecular Biology*, by Work et al., North Holland Publishing Company, NY (1978) with particular reference to the chapter entitled "*An Introduction to Radioimmune Assay and Related Techniques*" by Chard, incorporated entirely by reference herein. The radioactive isotope can be detected by such means as the use of a γ-counter, a scintillation counter or by autoradiography.

It is also possible to label an anti-neurocan polypeptide antibody with a fluorescent compound. When the fluorescently labeled antibody is exposed to light of the proper wave length, its presence can be then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine, commercially available, e.g., from Molecular Probes, Inc. (Eugene, Oreg.).

The antibody can also be detectably labeled using fluorescence emitting metals such as $^{152}$EU, or others of the lanthanide series. These metals can be attached to the antibody using such metal chelating groups as diethylenetriamine pentaacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in a immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen form the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays. See, e.g., for the above-mentioned immunological techniques, Harlow, supra; Ausubel et al, supra; and Sambrook et al, supra. Neurocan polypeptides of the present invention can be made by chemical synthesis or by recombinant methods, wherein chemical synthesis is preferred.

Synthetic Production of Neurocan Polypeptides of the Present Invention

Neurocan polypeptides of the present invention of shorter length, (e.g., up to 100 of several hundred amino acids) can be synthesized according to known method steps, including portions of known neurocan functional domains, consensus peptides thereof, conservative substitution derivative thereof or functional derivatives thereof.

Chemical polypeptide synthesis is a rapidly evolving area in the art, and methods of solid phase polypeptide synthesis are well-described in the following references, hereby entirely incorporated by reference: (Merrifield, B., *J. Amer. Chem. Soc.* 85:2149–2154 (1963); Merrifield, B., *Science* 232:341–347 (1986); Wade, J. D. et al., *Biopolymers* 25:S21–S37 (1986); Fields, G. B., *Int. J. Polypeptide Prot. Res.* 35:161 (1990); MilliGen Report Nos. 2 and 2a, Millipore Corporation, Bedford, Mass., 1987) Ausubel et al, supra, and Sambrook et al, supra.

Sequences available to use as a basis for polypeptide synthesis can be based on the combination of functional domains of SEQ ID NO:1 or a neurocan and published sequences of related functional domains as described herein, wherein the functional domains correspond to sections of hydrophobic amino acids of 5 to 500 amino acids, such as 25–50, 50–75, 75–90, 90–150, 90–100, 100–110, 110–120, 120–130, 140–150, 150–160, 160–170, 170–180, 170–200, 180–190, 190–200, 190–220, 200–210, 240–230, 230–240, 240–250, 250–300, 300–400, 400–500 amino acids in length.

Recombinant Expression of Neurocan Polypeptides of the Present Invention. Recombinant production of neurocan polypeptides can be accomplished according to known method steps. Standard reference works setting forth the general principles of recombinant DNA technology include Watson, J. D. et al., *Molecular Biology of the Gene,* Volumes I and II, The Benjamin/Cummings Publishing Company, Inc., publisher, Menlo Park, Calif. (1987); Darnell, J. E. et al., *Molecular Cell Biology,* Scientific American Books, Inc., publisher, New York, N.Y. (1986); Lewin, B. M., *Genes III,* John Wiley & Sons, publishers, New York, N.Y. (1989); Old, R. W., et al., *Principles of Gene Manipulation: An Introduction to Genetic Engineering,* 2d edition, University of California Press, publisher, Berkeley, Calif. (1981); Ausubel et al, eds., *Current Protocols in Molecular Biology,* Wiley Interscience, publisher, New York, N.Y. (1987, 1992); and Sambrook et al., *Molecular Cloning: A Laboratory Manual,* Second Edition, Cold Spring Harbor Laboratory, publisher, Cold Spring Harbor, N.Y. (1989), the entire contents of which references are herein incorporated by reference.

A nucleic acid sequence encoding a neurocan polypeptide of the present invention, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Ausubel et al, supra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as neurocan polypeptides in recoverable amounts. The precise nature of the regulatory regions needed for gene expression may vary from organism to organism, as is well known in the analogous art. See, e.g., Sambrook, supra and Ausubel supra.

The present invention accordingly encompasses the expression of a neurocan polypeptide, in either prokaryotic or eukaryotic cells, although eukaryotic expression is preferred.

Preferred hosts are bacterial or eukaryotic hosts including bacteria, yeast, insects, fungi, bird and mammalian cells either in vivo, or in situ, or host cells of mammalian, insect, bird or yeast origin. It is preferred that the mammalian cell or tissue is of human, primate, hamster, rabbit, rodent, cow, pig, sheep, horse, goat, dog or cat origin, but any other mammalian cell may be used.

Further, by use of, for example, the yeast ubiquitin hydrolase system, in vivo synthesis of ubiquitin-transmembrane polypeptide fusion proteins may be accomplished. The fusion proteins so produced may be processed in vivo or purified and processed in vitro, allowing synthesis of a neurocan transmembrane polypeptide of the present invention with a specified amino terminus sequence. Moreover, problems associated with retention of initiation codon-derived methionine residues in direct yeast (or bacterial) expression may be avoided. Sabin et al., *Bio/Technol.* 7(7): 705–709 (1989); Miller et al., *Bio/Technol.* 7(7): 698–704 (1989).

Any of a series of yeast gene expression systems incorporating promoter and termination elements from the actively expressed genes coding for glycolytic enzymes produced in large quantities when yeast are grown in mediums rich in glucose can be utilized to obtain neurocan polypeptides of the present invention. Known glycolytic genes can also provide very efficient transcriptional control signals. For example, the promoter and terminator signals of the phosphoglycerate kinase gene can be utilized.

Production of neurocan polypeptides or functional derivatives thereof in insects can be achieved, for example, by infecting the insect host with a baculovirus engineered to express transmembrane polypeptide by methods known to those of skill. See Ausubel et al, eds. *Current Protocols in Molecular Biology*, Wiley Interscience, §§16.8–16.11 (1987, 1992).

In a preferred embodiment, the introduced nucleotide sequence will be incorporated into a plasmid or viral vector capable of autonomous replication in the recipient host. Any of a wide variety of vectors may be employed for this purpose. See, e.g., Ausubel et al, supra, §§1.5, 1.10, 7.1, 7.3, 8.1, 9.6, 9.7, 13.4, 16.2, 16.6, and 16.8–16.11. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

The expressed protein may be isolated and purified in accordance with conventional conditions, such as extraction, precipitation, chromatography, affinity chromatography, electrophoresis, or the like. For example, the cells may be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immunoprecipitation. Alternatively, the transmembrane polypeptide or functional derivative thereof may be isolated by the use of anti-transmembrane polypeptide antibodies. Such antibodies may be obtained by well-known methods, some of which are mentioned below. These antibodies may be immobilized on cellulose, agarose, hollow fibers, or cellulose filters by covalent chemical derivatives by method step well known to those skilled in the art.

As discussed herein, neurocan polypeptides of the present invention may be further modified for purposes of drug design, such as for example to reduce immunogenicity, to prevent solubility and/or enhance delivery, or to prevent clearance or degradation.

Pharmaceutical Preparations of Neurocan Polypeptides of the Present Invention

Preparations of neurocan polypeptides for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods.

By the term "protection" from infection or disease as used herein is intended "prevention," "suppression" or "treatment." "Prevention" involves administration of a neurocan polypeptide, polypeptide derivative, or anti-idiotypic antibody prior to the induction of the disease.

"Suppression" involves administration of the composition prior to the clinical appearance of the disease.

"Treatment" involves administration of the protective composition after the appearance of the disease. It will be understood that in human and veterinary medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis."

At least one neurocan polypeptide, antibody or anti-idiotypic antibody of the present invention may be administered by any means that achieve their intended purpose, for example, to treat neurocan related, pathologies, such as cell inflammatory, allergy-, tissue damage or other related pathologies, using a neurocan polypeptide corresponding to at least one neurocan functional domain or consensus portion thereof, in the form of a pharmaceutical composition.

For example, administration of such a composition may be by various parenteral routes such as subcutaneous, intravenous, intradermal, intramuscular, intraperitoneal, intranasal, transdermal, or buccal routes. Alternatively, or concurrently, administration may be by the oral route. Parenteral administration can be by bolus injection or by gradual perfusion over time.

A preferred mode of using a neurocan pharmaceutical composition of the present invention is by oral administration or intravenous application.

A typical regimen for preventing, suppressing, or treating neurocan-related pathologies, such as comprises administration of an effective amount of a neurocan polypeptide, administered over a period of one or several days, up to and including between one week and about 24 months.

It is understood that the dosage of a neurocan polypeptide of the present invention administered in vivo or in vitro will be dependent upon the age, sex, health, and weight of the recipient, kind of concurrent treatment, if any, frequency of treatment, and the nature of the effect desired. The ranges of effective doses provided below are not intended to limit the invention and represent preferred dose ranges. However, the most preferred dosage will be tailored to the individual subject, as is understood and determinable by one of skill in the art, without undue experimentation. See, e.g., Berkow et al., eds., *The Merck Manual*, 15th edition, Merck and Co., Rahway, N.J., 1987; Goodman et al., eds., *Goodman and Gilman's The Pharmacological Basis of Therapeutics*, 8th edition, Pergamon Press, Inc., Elmsford, N.Y., (1990); *Avery's Drug Treatment: Principles and Practice of Clinical Pharmacology and Therapeutics*, 3rd edition, ADIS Press, LTD., Williams and Wilkins, Baltimore, Md. (1987), Ebadi, *Pharmacology*, Little, Brown and Co., Boston, (1985), which references and references cited therein, are entirely incorporated herein by reference.

The total dose required for each treatment may be administered by multiple doses or in a single dose. A neurocan polypeptide may be administered alone or in conjunction with other therapeutics directed to neurocan related pathologies, such as a leukocyte-endothelial cell recognition related pathology as a non-limiting example, or directed to other symptoms of cell adhesion, developmental or other diseases, as described herein.

Effective amounts of the a neurocan polypeptide or composition, which may also include a neurocan antibody or anti-idiotypic antibody, are from about 0.01 µg to about 100 mg/kg body weight, and preferably from about 10 µg to about 50 mg/kg body weight, such 0.05, 0.07, 0.09, 0.1, 0.5, 0.7, 0.9, 1, 2, 5, 10, 20, 25, 30, 40, 45, 50, 55, 60, 65, 70, 75, 80, 85, 90, 95 or 100 mg/kg.

Preparations for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods. See, e.g., Berker, supra, Goodman, supra, Avery, supra and Ebadi, supra, which are entirely incorporated herein by reference, inlcuded all references cited therein.

Pharmaceutical compositions comprising at least one neurocan polypeptide, such as 1–10 or 1, 2, 3, 4, 5, 6, 7, 8, 9 or 10 neurocan polypeptides, of the present invention may include all compositions wherein the neurocan polypeptide is contained in an amount effective to achieve its intended purpose. In addition to at least one neurocan polypeptide, a pharmaceutical composition may contain suitable pharmaceutically acceptable carriers, such as excipients, carriers and/or auxiliaries which facilitate processing of the active compounds into preparations which can be used pharmaceutically.

Pharmaceutical compositions comprising at least one neurocan may also include suitable solutions for administration intravenously, subcutaneously, dermally, orally, mucosally, rectally or may by injection or orally, and contain from about 0.01 to 99 percent, preferably from about 20 to 75 percent of active component (i.e. the antibody) together with the excipient. Pharmaceutical compositions for oral administration include tablets and capsules. Compositions which can be administered rectally include suppositories. See, e.g., Berker, supra, Goodman, supra, Avery, supra and Ebadi, supra, which are entirely incorporated herein by reference, inlcuded all references cited therein.

Having now generally described the invention, the same will be further understood by reference to certain specific examples which are included herein for purposes of illustration only and are not intended to be limiting unless otherwise specified.

EXAMPLE 1

CLONING, SEQUENCING AND EXPRESSION OF A NEUROCAN POLYPEPTIDE

EXPERIMENTAL PROCEDURES

Preparation of peptides and amino acid sequence analysis. Proteoglycans were isolated from 7-day or adult brain by immunoaffinity chromatography using the 1D1 monoclonal antibody as described previously (Rauch et al., 1991). 60 µg of chondroitinase-treated adult brain 1D1 proteoglycan protein were electrophoresed under nonreducing conditions on four lanes of a 5% 0.75 mm minigel and stained with Coomassie Blue using a low concentration (0.5%) of acetic acid. Bands containing the 150 kDa core glycoprotein were excised, lyophilized, and each placed in 50 µl of 50 mM ammonium bicarbonate buffer (pH 8.6) containing 1 mM EDTA, and 0.15 µg of endoproteinase LysC (Promega). After digestion for 4 h at 37° C. the bands were again lyophilized, reswollen in 30 µl of sample buffer containing mercaptoethanol, and placed in wells of a 10% 1 mm minigel for re-electrophoresis and transfer to a ProBlott membrane as described below.

For treatment with endoproteinase Asp-N, 84 µg of chondroitinase-treated adult brain 1D1 proteoglycan protein were digested for 30 min at 37° C. with 0.14 µg of enzyme in 280 µl of 100 mM ammonium bicarbonate buffer (pH 8.0), lyophilized, and electrophoresed on four lanes of a 10% gel before transfer to a ProBlott membrane.

Peptides were also prepared by treating 100 µg of chondroitinase-digested 1D1 proteoglycan from 7-day or adult brain with CNBr in 500 µl of 70% formic acid for 18 h at room temperature. After dilution with 4.5 ml of water and lyophilization followed by a second lyophilization of 4.5 ml of water, the residue was dissolved in sample buffer for electrophoresis on four lanes of a 16% minigel and transfer to a ProBlott membrane.

The N-terminal sequence of the adult 1D1 proteoglycan core glycoprotein was determined using the 150 kDa bands transferred to a ProBlott membrane after SDS-PAGE of chondroitinase-treated proteoglycan, whereas the 245 kDa core glycoprotein obtained by chondroitinase treatment of the proteoglycan from 7-day brain was sequenced directly. In all cases, chondroitinase treatment was performed using 0.5 mU of protease-free chondroitinase ABC (Seikagaku America Inc.) per µg of proteoglycan protein, as described previously (Rauch et al., 1991).

Electrophoresis was performed as described by Laemmli (1970) with the modifications that the gel was pre-electrophoresed for 30 min at 100 volts (30–40 mA) at 4° C. using stacking gel buffer containing 0.1 mM thioglycolic acid in the upper buffer chamber and sample wells (after which both buffers were changed), and 0.1 mM thioglycolic acid was added to the upper buffer for electrophoresis of the samples. Separated proteins were transferred to ProBlott membranes (Applied BioSystems, Foster City, Calif.) at 50 volts (about 11 V/cm, 120–150 mA) for 30 min at room temperature in 10 mM CAPS buffer (pH 11) containing 10% methanol. Before transfer, the gel was allowed to stand in transfer buffer for 5 min, and the membrane was wetted with methanol and allowed to stand for 15 min in transfer buffer before use. Membranes containing transferred proteins were washed several times with water followed by a few seconds in methanol, stained for 1 min in 50% methanol containing 1% acetic acid and 0.1% Coomassie Blue, destained in 50% methanol, washed with water, and air-dried. Transferred protein bands were excised from the membrane sheet and sequenced on an Applied Biosystems Model 475A instrument equipped with the Blott cartridge.

To obtain additional amino acid sequence data, a 65 kDa endo Lys-C peptide obtained uniquely from the core glycoprotein of the early postnatal form of the 1D1 proteoglycan was blotted to nitrocellulose, the excised bands were blocked with PVP-40 and digested with trypsin, and the resulting tryptic peptides were separated by HPLC and used for microsequencing (Aebersold et al., 1987).

Generation of a probe by the PCR and isolation of adult brain 1D1 proteoglycan clones. Based on two of the internal peptide sequences determined for the 150 kDa core glycoprotein of the adult brain 1D1 proteoglycan, sense and anti-sense oligonucleotide primers were synthesized with BamH1 and Hind III linkers (FIG. 1B) (SEQ ID NOS:9–10). Deoxyinosine was substituted in positions where the codon degeneracy is >2, and mixed pairs of bases were used at positions where there are only two triplet codons. We initially used 20 cycles of the PCR to amplify all inserts in a 6-week rat brain λ-ZAPII cDNA library (Stratagene), employing the Bluescript forward and reverse (BSK and BKS) primers to which we added 6 bases in each case. Aliquots of this product and of the original cDNA library were then tested using our 1D1 proteoglycan-specific primers described above for further amplification with Taq polymerase (Perkin-Elmer/Cetus), using 40 temperature-step cycles of 94° C. (0.5 min), 50° C. (1.5 min), and 72° C. (with extension time increasing from 2 to 6 min). Agarose-ethidiumbromide gel electrophoresis of the PCR reaction products demonstrated an about 800 bp band which was not produced from a control reaction containing only empty 1ZAPII vector.

The PCR product was treated sequentially with polynucleotide kinase and the Klenow fragment of DNA polymerase I, purified by agarose gel electrophoresis and Qiaex extraction (Qiagen Inc., Chatsworth, Calif.), and subcloned into the SmaI site of pGEM-7Z (Promega) for further analysis of recombinant plasmids amplified in E. coli XL1-Blue cells. The pGEM-7Z/PCR product plasmid was then cut with Hind III, and used with the Promega Riboprobe Gemini II core system to generate an RNA sense probe for screening the original rat brain λZAPII cDNA library. RNA transcripts were prepared according to the Promega Protocols and Applications Guide in the presence of [a32P]CTP (10 mCi/ml, 800 Ci/mmol), and used without removal of the template.

Plaques were transferred to nitrocellulose filters and DNA was immobilized by baking in vacuo. Filters were hybridized overnight at 50° C. in buffer containing 50% formamide, 6X SSC, 1% SDS, 0.1% Tween 20, and 100 µg/ml tRNA, and washed 3 times at room temperature with 1 X SSC, 0.1% SDS, and twice at 65° C. with 0.1X SSC, 0.1% SDS. Supernatants of positive plaques after the second screening were used as templates in a PCR amplification using an antisense primer based on nucleotides 2914–2940 of the composite sequence together with each of the two 23-mer vector primers which were previously used to amplify the library inserts. Amplification was performed using 50 cycles of 94° C. (0.5 min), 55° C. (1.5 min), and 72° C. (5 min).

Reverse transcription/PCR, and isolation of 245 kDa core protein clones. Using the GeneAmp RNA PCR Kit (Perkin Elmer Cetus), 0.75 µg of 4-day rat brain mRNA were reverse transcribed for 60 min at 42° C. in a volume of 20 µl, followed by 5 min at 99° C. and 5 min at 5° C. All of the PCR components except the Taq polymerase were then added and heated for 5 min at 95° C. After cooling to 55° C. and addition of Taq polymerase (in 10 µl of 1 X buffer, to give a total volume of 100 µl), the template was amplified by 45 PCR cycles (0.5 min at 94° C., 1.5 min at 55° C., and 5 min at 72° C.). The large molecular size portion of this PCR product was amplified with degenerate oligonucleotide primers based on amino acid sequences obtained from the N-terminus of a 70 kDa CNBr peptide derived from the 1D1 proteoglycan and conserved sequences from the hyaluronic acid-binding region present in other proteins and proteoglycans (FIG. 2B) (SEQ ID NOS:18–22), then reamplified under the same conditions and blunt-end ligated into the SmaI site of pGEM7 as described above. Four of 12 minipreps gave inserts of the expected size, and one of these was digested with BamHi to generate a template for the transcription of an RNA probe (as described above for the adult brain 1D1 proteoglycan).

For the preparation of lysates, phage were grown for 6 h at a density of 50,000 pfu/150 mm plate, and eluted with 10 ml of SM buffer by gentle shaking overnight at 4° C. In a first screening, 2 µl aliquots of three lysates were pooled and used as template for 50 cycles of PCR amplification using exactly matching 23-mer primers in a total volume of 50 µl (0.5 min at 94° C., 1.5 min at 55° C., and 2 min at 72° C.). The reaction mixture was heated for 5 min at 95° C. and then cooled to 60° C. for addition of the Taq polymerase. Pools which gave a PCR product of the expected size were then tested individually using 5 µl aliquots of each lysate as template. After the first round of screening, the same conditions were used to test the supernatants (SM buffer containing 2 drops of chloroform) of agarose plugs of possibly positive plaques.

DNA sequencing. Subclones for sequencing were generated either by deletions produced with restriction enzymes or by subcloning of restriction fragments into pGEM3 or pGEM7 (Promega), and sequencing was also performed using synthetic primers corresponding to the 5' portion of previously determined sequences. DNA sequencing was performed both manually by the dideoxynucleotide chain-termination method using deoxyadenosine 5'[α[35S]thio] triphosphate and Sequenase (United States Biochemical), and with Taq polymerase in conjunction with dye-labeled primers or terminators and the Applied Biosystems Model 373A DNA sequencing system. Both strands of the coding region of cloned cDNAs were sequenced, with sequence alignment and analysis accomplished with the software package from the Genetics Computer Group (Madison, Wis.). The reading frame was verified by our N-terminal amino acid sequence data for the 150 and 245 kDa core glycoproteins and for proteolytic fragments derived from them. Sequence comparisons with the SwissProt database were performed using the Pearson-Lipman algorithm (Pearson and Lipman, 1988) with a ktup value of 2.

Northern Blots. A 307 bp PstI-BamHI restriction fragment (nucleotides 2624–2930) was subcloned into pGEM3 by directional cloning. This fragment represents the portion of the protein sequence just preceding (but not including) the domains homologous with versican and aggrecan. The plasmid was cut with Hind III and transcribed into digoxigenin-labeled antisense RNA with T7 RNA polymerase (Promega) using the GENIUS 4 RNA labeling kit (Boehringer Mannheim). The resulting probe was used for hybridization with Northern blots of mRNA prepared from brain and other tissues using the FastTrack mRNA isolation kit (Invitrogen Corp., San Diego, Calif.). Hybridization, washing, and detection with alkaline phosphatase-labeled anti-digoxigenin antibodies were as described in the manufacturer's instructions.

Dot binding assay. To test the reactivity of a synthetic peptide with the 8A4 monoclonal antibody, the peptide (50 μg/ml) was conjugated to BSA (30–60 μg/ml) using glutaraldehyde, and adsorbed to nitrocellulose as described by Sithigorngul et al. (1991). After blocking with BSA, antibody binding was detected with alkaline phosphatase-conjugated rabbit anti-mouse immunoglobulins, in conjunction with nitroblue tetrazolium and 5-bromo-4-chloro-indolyl phosphate (Promega, Madison, Wis.).

RESULTS

Synthesis of a probe for the adult 1D1 proteoglycan by the polymerase chain reaction and isolation of cDNA clones. N-terminal microsequencing of peptides produced by limited proteolysis of chondroitinase-treated proteoglycan with endoproteinases Lys-C and Asp-N, and of a 45 kDa core glycoprotein obtained by chondroitinase treatment of one preparation of 1D1 proteoglycan, all yielded overlapping sequences beginning within a sequence of 13 amino acids (FIG. 1) (SEQ ID NOS:2–5). Entirely different N-terminal amino acid sequences were obtained from each of two CNBr degradation products (13 (SEQ ID NO:8) and 24 (SEQ ID NO:6) kDa) of the 150 kDa 1D1 core glycoprotein (FIG. 1). Products of identical size were also obtained by CNBr treatment of the 45 kDa core glycoprotein (data not shown). The N-terminal sequence of the 24 kDa peptide had a high degree of identity with the EGF-like repeats in various proteins including human aggrecan, and the 13 kDa peptide had a similarly high degree of identity with the junction of the lectin-like and complement regulatory protein-like domains present in versican and in all of the sequenced aggrecans. Therefore, for the synthesis of our antisense PCR primer, we chose tryptophan and cysteine in two positions where the identity of the amino acid was not clear from our sequencing data (FIG. 1), based on the location in the aggrecan and versican sequences of these usually highly conserved amino acids. Although the restriction sites added to both primers were not used in the blunt-end ligation of the PCR product, they later proved to be quite helpful for the analysis of plasmid minipreps of the colonies obtained after transfection.

An oligo(dT)-primed six-week rat brain 1ZAPII cDNA library was used as template, and preamplification of all inserts with primers synthesized on the basis of the Bluescript BSK and BKS primers substantially improved the yield of specific PCR product. The PCR product was ligated into pGEM-7Zf and transfected into *E. coli* XL1-Blue cells. Dideoxy sequencing of this PCR product demonstrated that both the 3' and 5' ends contained nucleotides encoding the respective 1D1 amino acid sequences adjacent to those utilized in our primer design.

The rat brain λ-ZAPII cDNA library was screened with a 640 base RNA transcript of the cloned PCR product. By screening about 900,000 plaques 15 positive plaques were identified, 10 of which were used for a second screening and yielded 9 positives. Supernatants of the best separated plaques of these clones were tested with the PCR using each of the Bluescript primers and an antisense primer based on a nucleotide sequence near the 5' end of our original PCR product. Only three of the clones gave specific PCR products (of 0.9 and 1.4 kb), indicating a substantial amount of sequence 5' of our PCR product. Two of these clones were converted into Bluescript clones by in vivo excision and sequenced as indicated in FIG. 3.

The sequence of clone BS41 was found to diverge from that of the previously obtained sequence of the PCR product at the same point where an exon-intron junction has been found in the lectin-like domain of aggrecan (Tanaka et al., 1988). Our sequencing efforts were therefore concentrated on clone BS72, within which the 3' end of the coding region of BS41 was also found. Although the complete nucleotide sequence of BS41 has not been obtained, restriction analysis of this clone clearly indicates the presence of a about 1 kb intron between bases 3308 and 3309 of the composite cDNA sequence. Within the longest open reading frame, the N-terminal amino acid sequence of the adult brain 1D1 proteoglycan was found (FIG. 1) (SEQ ID NO:2), beginning at nucleotide 1991 of our composite sequence (FIG. 4) (SEQ ID NO:1) and predicting a protein of 619 amino acids.

Synthesis of a probe for the early postnatal 1D1 proteoglycan and isolation of cDNA clones. We have previously demonstrated that the 150 kDa core glycoprotein of the adult brain 1D1 proteoglycan is a part of the 245 kDa core glycoprotein of early postnatal brain, because all of the peptides generated from it could also be found in the larger species (Rauch et al., 1991). Therefore, an antisense primer corresponding to the most 5' nucleotide sequence coding for the 150 kDa core protein was used to initiate a reverse transcription and (together with a sense primer based on CNBr peptide 1; FIG. 2) (SEQ ID NO:18) PCR amplification of rat brain mRNA.

A faint smear extending from about 1.2 to 3.5 kbp was cut out of the agarose gel and Qiaex purified. Aliquots of 10% of this material were used as template with several primer combinations, from which the CNBr peptide 1 sense primer and an antisense primer based on the conserved tandem repeat sequence CDAGWLADQ (SEQ. ID No:44) yielded a 550 bp product which coded for an amino acid sequence having about 50% identity to the hyaluronic acid-binding region of other aggregating proteoglycans. Because only very weak or no PCR signals could be obtained using these degenerate primers and several insert-amplified brain cDNA libraries as template, cDNA sequence-specific primers were synthesized based on the 3' and 5' sequences of the PCR product. These primers yielded a 450 bp PCR product using an oligo(dT) and random primed rat brain stem λ-ZAPII cDNA library as template (Stratagene, 100 g rat).

The library was divided into 27 aliquots of 50,000 pfu and lysates from each of these aliquots were tested by PCR using the sequence-specific primers described above. The seven lysates yielding a positive PCR signal were each grown on two plates (50,000 pfu/plate) and screened with an antisense RNA transcript of the original PCR product. Supernatants of possibly positive plaques were again checked by PCR and yielded four positive clones from different primary lysates. All of these were then converted into Bluescript plasmids by in vivo excision after a second screening, and three of these were used for sequencing (FIG. 5).

Figure 6:
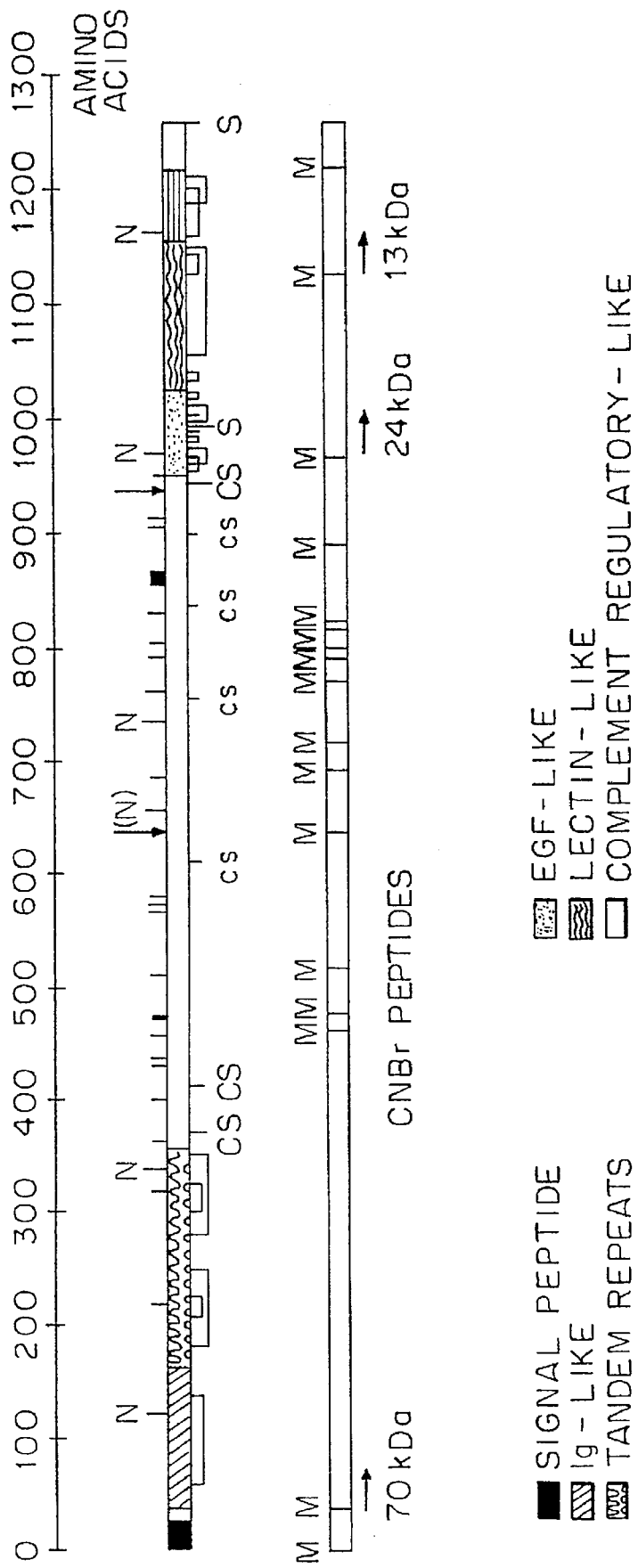
FIG. 6. Diagram of the neurocan core protein showing the probable location of disulfide bonds in the hyaluronic acid-binding domain (Neame et al., 1986) and in EGF-like (Engel, 1989), lectin-like (Spiess, 1990), and complement regulatory protein-like domains; the two cysteine residues which are not part of the established pattern (S); potential N- and threonine O-glycosylation sites (the latter indicated by short vertical bars); and chondroitin sulfate (CS) attachment sites. The most probable chondroitin sulfate attachment sites are indicated by larger letters, and the potential N-glycosylation site at Asn655 is shown in parentheses because it may not be utilized, insofar as asparagine was detected in this position in our amino acid sequencing of the 150 kDa core glycoprotein (cf.

Primary structure of neurocan. The 3' sequence of the early postnatal 1D1 proteoglycan cDNA clones overlapped with the 5' sequence of clones coding for the adult brain proteoglycan. An open reading frame of 3771 bp encodes a 1257 residue protein with a molecular mass of 136 kDa, containing 10 different peptide sequences present in the adult and/or early postnatal proteoglycans (FIG. 4) (SEQ ID NO:1). The composite sequence is 5.2 kb long, including 1.3 kb of 3' untranslated sequence and 76 bp of 5' untranslated sequence. The deduced amino acid sequence revealed a 22 amino acid signal peptide followed by an immunoglobulin domain and tandem repeats characteristic of the hyaluronic acid-binding region of aggrecan and versican (FIG. 6). The 125 amino acids of the neurocan Ig-like domain (residues 36–160 (of SEQ ID NO:1) are 41–42% identical to corresponding sequences of 126–131 amino acids in rat aggrecan and human versican. The following tandem repeat domains (residues 161–355; FIG. 7; SEQ ID NOS. 23–26) have a considerably higher degree of identity (57–58%) with aggrecan and versican domains of the same size (Doege et al., 1987; Zimmermann and Ruoslahti, 1989), and also contain the 17 amino acids which are identical in each of the repeats of neurocan, versican, rat and human aggrecan, and the four sequenced link proteins (Perkins et al., 1991). The tandem repeats are closely followed by an RGDS sequence (amino acids 364–367 of SEQ ID NO:1). The C-terminal portion (amino acids 951–1215 of SEQ ID NO:1) has 60% identity to a region in the C-terminus of versican, which includes two epidermal growth factor-like domains, a lectin-like domain, and a complement regulatory protein-like sequence, and a comparison of the 191 amino acids of only the lectin-like and complement regulatory protein-like region of neurocan with the equivalent regions in rat, human, bovine, and chicken aggrecan also revealed identities of 59%. The central 595 amino acid (residues 356–950 of SEQ ID NO:1) portion of neurocan has no homology with other reported protein sequences. One difference of possible biological importance is that neurocan contains two additional cysteine residues (FIG. 6, and indicated with asterisks in FIG. 4) which do not fit the usual pattern of the homology domains. It may also be of significance that the entire non-homologous central portion of neurocan (amino acid residues 356–950 of SEQ ID NO:1) has a high concentration (about 35%) of serine, threonine, and proline, whereas basic amino acids account for 59% of the 41 C-terminal residues, which also include a high proportion (17%) of acidic amino acids (Table IV).

TABLE IV

AMINO ACID COMPOSITION OF NEUROCAN
(residues/100 residues)

| | Adult Brain Proteoglycan | | | |
|---|---|---|---|---|
| | | Non-homologous Domain | | |
| N-Terminal | | | C-Terminal | C-Terminus |
| Homology | Part I | Part II | Homology Domain | |
| (23–355) | (356–638) | (639–950) | (951–1215) | (1216–1257) |
| His | 2 | 3 | 2 | 5 | 26 |
| Lys | 2 | 2 | 2 | 4 | 12 |
| Arg | 10 | 4 | 1 | 7 | 21 |
| Asp | 6 | 5 | 5 | 7 | 7 |
| Glu | 4 | 8 | 8 | 7 | 10 |
| Asn | 1 | 1 | 1 | 8 | 0 |
| Gln | 6 | 5 | 3 | 3 | 0 |
| Ser | 5 | 14 | 15 | 4 | 2 |
| Thr | 6 | 8 | 9 | 5 | 0 |
| Gly | 9 | 9 | 8 | 10 | 2 |
| Ala | 11 | 9 | 8 | 4 | 2 |
| Val | 7 | 5 | 9 | 6 | 0 |
| Leu | 10 | 8 | 9 | 4 | 0 |
| Ile | 2 | 3 | 3 | 3 | 0 |
| Met | <1 | 1 | 3 | 1 | 2 |
| Phe | 4 | 1 | 1 | 3 | 2 |
| Tyr | 4 | 0 | 0 | 4 | 0 |
| Trp | 2 | 1 | 2 | 3 | 2 |
| Pro | 6 | 13 | 12 | 5 | 7 |
| Cys | 3 | 0 | 0 | 9 | 2 |

Homology domains refer to sequences homologous to versican and aggrecan. Numbers in parentheses above the columns represent amino acids in the complete (early postnatal) neurocan sequence (cf. FIG. 4).

The native neurocan proteoglycan contains six potential N-glycosylation sites and 25 potential threonine O-glycosylation sites (Gooley et al., 1991). There is a total of seven potential chondroitin sulfate attachment sites (FIG. 8; SEQ ID NOS: 27–33)), which is more than sufficient to accommodate the calculated three chondroitin sulfate chains present in the 1D1 proteoglycan (Rauch et al., 1991). At least one of these chains is located at serine-372 and/or serine-410 of SEQ ID NO:1), since we previously found that the 70 kDa CNBr peptide derived uniquely from the early postnatal form of the 1D1 proteoglycan is recognized by monoclonal antibodies to the unsaturated disaccharide "stubs" remaining on the core protein after chondroitinase treatment of the proteoglycan (Rauch et al., 1991).

From adult brain, only the C-terminal portion of neurocan (beginning with amino acid 639) can be isolated by immunoaffinity chromatography using the 1D1 monoclonal antibody. Although there are four serine-glycine sequences in the C-terminal half of the proteoglycan which could serve as potential chondroitin sulfate linkage sites (FIG. 8), serine-944 of SEQ ID NO:1 is the only one of these sites which is present in a 45 kDa core glycoprotein obtained by chondroitinase treatment of one preparation of adult 1D1 proteoglycan (which was apparently subject to partial proteolysis during the isolation procedure; cf. FIG. 1A). The single 32 kDa chondroitin 4-sulfate chain present in the adult form of the 1D1 proteoglycan (Rauch et al., 1991) is attached at serine-944 of SEQ ID NO:1. All of the 12 potential threonine O-glycosylation sites in the adult form of the 1D1 proteoglycan are located in its N-terminal, non-homologous half.

In addition to sequence homologies with other proteoglycans, amino acids 907 to 952 (of SEQ ID NO:1) of neurocan have 33% identity and 56% similarity (FIG. 9; SEQ ID NOS: 34–35) with a sequence in the putative calcium-sensitive actin-binding domain of human gelsolin (Kwiatkowski et al., 1986). These values increase slightly to 38% identity and 63% similarity if only the 24 C-terminal amino acids of this sequence are compared.

A comparison of the N-terminal half of the amino acid sequence of adult 1D1 with itself utilizing a dot plot matrix (with window and stringency values of 60 and 24, respectively) indicated a highly repetitive structure which in certain cases allowed more than one possible alignment, the best of which is shown in FIG. 10 (SEQ ID NOS:36–43).

Northern blotting. Northern blots of mRNA from 4-day and adult rat brain were probed with an RNA transcript corresponding to a portion of the neurocan sequence immediately preceding the C-terminal domains homologous with versican and aggrecan. In both cases only a single major band at about 7.5 kb was recognized. Northern blots of mRNA from adult rat liver, lung, kidney, and muscle revealed no detectable neurocan transcripts in these tissues (FIG. 11).

Structure of the 8A4 epitope. Both the 150 and 245 kDa 1D1 proteoglycan core proteins react on immunoblots with the 8A4 monoclonal antibody to rat chondrosarcoma link protein (Rauch et al., 1991), as does a fusion protein expressed by bacteria transfected with a full-length adult brain 1D1 proteoglycan construct. Neame et al. (1985) have described two peptides derived by trypsin or chymotrypsin digestion from rat chondrosarcoma link protein, both of which bind to the 8A4 monoclonal antibody and have in common the sequence Leu-Ala/Ser-Asp-Gly-Ser-Val-Arg/Gln-Tyr-Pro-Ile-Ser/Thr-Lys/Arg-Pro (SEQ ID NO:45), whereas the first seven of these amino acids comprised the C-terminal portion of a tryptic peptide which was not recognized by 8A4. These findings indicate that the 8A4 epitope lies within this 13 amino acid sequence, and possibly in the six C-terminal residues. Although the two homologous sequences in the neurocan tandem repeats (indicated by asterisks in FIG. 7) are present only in the early postnatal form of the proteoglycan, the related sequence Pro-Ile-Ser-Gly-Pro (SEQ ID NO:46) is present near the N-terminus of the adult brain 1D1 proteoglycan (amino acids 725–729; FIG. 4; of SEQ ID NO:1. Because only this last sequence is present in both the 150 and 245 kDa core proteins, our data suggest that the 8A4 epitope is more closely defined by the sequence Pro-Ile-Ser/Thr-Xaa-Pro (SEQ ID NO:48), and this identification was confirmed by demonstrating that the synthetic peptide His-Pro-Ile-Ser-Gly-Pro-Trp (SEQ ID NO:47) was recognized by the 8A4 monoclonal antibody when tested in a dot binding assay on nitrocellulose.

The overlapping cDNA clones is 5.2 kb long, including 1.3 kb of 3' untranslated sequence and 76 bp of 5' untranslated sequence. An open reading frame of 1257 amino acids encodes a protein with a molecular mass of 136 kDa containing 10 peptide sequences present in the adult and/or early postnatal brain proteoglycans. The deduced amino acid sequence revealed a 22 amino acid signal peptide followed by an immunoglobulin domain, tandem repeats characteristic of the hyaluronic acid-binding region of aggregating proteoglycans, and an RGDS sequence. The C-terminal portion (amino acids 951–1215 of SEQ ID NO:1 has about 60% identity to regions in the C-termini of the fibroblast and cartilage proteoglycans, versican and aggrecan, including two epidermal growth factor-like domains, a lectin-like domain, and a complement regulatory protein-like sequence. The central 595 amino acid portion (residues 356–950 of SEQ ID NO:1) of neurocan has no homology with other reported protein sequences. The proteoglycan contains six potential N-glycosylation sites and 25 potential threonine O-glycosylation sites. In the adult form of the proteoglycan (which represents the C-terminal half of neurocan) a single 32 kDa chondroitin 4-sulfate chain is linked at serine-944 (SEQ ID NO:1), whereas three additional potential chondroitin sulfate attachment sites (only two of which are utilized) are present in the larger proteoglycan species. A probe corresponding to a region of neurocan having no homology with versican or aggrecan hybridized with a single band at about 7.5 kb on Northern blots of mRNA from both 4-day and adult rat brain (but not with muscle, kidney, liver, or lung mRNA), indicating that the 1D1 proteoglycan of adult brain, containing a 68 kDa core protein, is generated by a developmentally regulated in vivo proteolytic processing of the 136 kDa species which is predominant in early postnatal brain. Neurocan aggregates with hyaluronic acid, and both core proteins are recognized by the 8A4 monoclonal antibody to rat chondrosarcoma link protein. This antibody also reacts with a 45 kDa link protein which copurifies with the proteoglycans isolated from either early postnatal or adult brain. Our data indicate that the 8A4 epitope is a Pro-Ile-Ser/Thr-Xaa-Pro (SEQ ID NO:48) sequence present in both link protein and the 1D1 proteoglycan core proteins, and we demonstrated that this antibody recognizes the synthetic peptide His-Pro-Ile-Ser-Gly-Pro-Trp (SEQ ID NO:47) in a dot-binding assay.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the generic concept of the present invention. Therefore, such adaptations and modifications are intended to be comprehended within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein.

REFERENCES

Aebersold, R. H., Leavitt, J., Saavedra, R. A., Hood, L. E., and Kent, S. B. (1987) *Proc. Natl. Acad. Sci. U.S.A.* 84, 6970–6974.

Aquino, D. A., R. U. Margolis, and R. K. Margolis. (1984a) *J. Cell. Biol.* 99, 1117–1129.

Aquino, D. A., R. U. Margolis, and R. K. Margolis. (1984b) *J. Cell Biol.* 99, 1130–1139.

Argarana, C. E., Barra, H. S., and Caputto, R. (1981) *J. Biol. Chem.* 256, 827–830.

Benedum, U. M., Baeuerle, P. A., Konecki, D. S., Frank, R., Powell, J., Mallet, J., and Huttner, W. B. (1986) *EMBO J.* 5, 1495–1502.

Bourdon, M. A., Krusius, T., Campbell, S., Schwartz, N. B., and Ruoslahti, E. (1987) *Proc. Natl. Acad. Sci. U.S.A.* 84, 3194–3198.

Breuer, B., Quentin, E., Cully, Z., Götte, M., and Kresse, H. (1991) *J. Biol. Chem.* 266, 13224–13232.

Brittis, P. A., Canning, D. B., and Silver, J. (1992) *Science* 255, 733–736.

Brandley, B. K., Swiedler, S. J., and Robbins, P. W. (1990) *Cell* 63, 861–863.

Crossin, K. L., Hoffman, S., Tan, S. -S., and Edelman, G. M. (1989) *Dev. Biol.* 136, 381–392.

Doege, K., Sasaki, M., Horigan, E., Hassell, J. R., and Yamada, Y. (1987) *J. Biol. Chem.* 262, 17757–17767.

Doege, K. J., Sasaki, M., Kimura, T., and Yamada, Y. (1991) *J. Biol. Chem,* 266, 894–902.

Engel, J. (1989) *FEBS Lett.* 251, 1–7.

Finne, J., Krusius, T., Margolis, R. K., and Margolis, R. U. (1979) *J. Biol. Chem.* 254, 10295–10300.

Fryer, H. J. L., Kelly, G. M., Molinaro, L., and Hockfield, S. (1992) *J. Biol. Chem.* 267, 9874–9883.

Gooley, A. A., Classon, B. J., Marschalek, R., and Williams, K. L. (1991) *Biochem. Biophys. Res. Comm.* 178, 1194–1201.

Gribskov, M, and Burgess, R. R. (1986) *Nucl. Acids Res.* 14, 6745–6763.

Halberg, D. F., Proulx, G., Doege, K., Yamada, Y., and Drickamer, K. (1988) *J. Biol. Chem.* 263, 9486–9490.

Hoffman, S., Crossin, K. L., and Edelman, G. M. (1988) *J. Cell Biol.* 106, 519–532.

Iacangelo, A., Affolter, H. -U., Eiden, L. E., Herbert, E., and Grimes, M. (1986) *Nature* 323, 82–86.

Kang, J., Lemaire, H. -G., Unterbeck, A., Salbaum, J. M., Masters, C. L., Grzeschik, K. -H., Multhaup, G., Beyreuther, K., and Müller-Hill, B. (1987) *Nature* 325, 733–736.

Kaufmann, E., Geisler, N., and Weber, K. (1984) *FEBS LETT.* 170, 81–84.

Krueger, R. C., Fields, T. A., Hildreth, J., and Schwartz, N. B. (1990) *J. Biol. Chem.* 265, 12075–12087.

Krusius, T., Finne, J., Margolis, R. K., and Margolis, R. U. (1986) *J. Biol. Chem.* 261, 8237–8242.

Krusius, T., Reinhold, V. N., Margolis, R. K., and Margolis, R. U. (1987) *Biochem. J.* 245, 229–234.

Kwiatkowski, D. J., Stossel, T. P., Orkin, S. H., Mole, J. E., Colten, H. R., and Yin, H. L. (1986) *Nature* 323, 455–458.

Laemmli, U. K. (1970) *Nature* (Lond.) 227, 680–685.

Leach, B. S., Collawn, Jr., J. F., and Fish, W. W. (1980) *Biochemistry.* 19, 5734–5741.

LeBaron, R. G., Zimmermann, D. R., and Ruoslahthi, E. (1992) *J. Biol. Chem.* 267, 10003–10010.

Lee, C. C., Wu, X., Gibbs, R. A., Cook, R. G., Muzny, D. M. and Caskey, C. T. (1988) *Science* 239, 1288–1291.

Margolis, R. K., and Margolis, R. U. (1989) in *Neurobiology of Glycoconjugates* (Margolis, R. U. and Margolis, R. K., eds.) pp. 85–126, Plenum Publishing Corp., New York.

Margolis, R. K., Goossen, B., Tekotte, H., Hilgenberg, L., and Margolis, R. U. (1991) *J. Cell Sci.* 99, 237–246.

McCormick, D., van der Rest, M., Goodship, J., Lozano, G., Ninomiya, Y., and Olsen, B. R. (1987) *Proc. Natl. Acad. Sci. U.S.A.* 84, 4044–4048.

McKeon, R. J., Schreiber, R. C., Rudge, J. S., and Silver, J. (1991) *J. Neurosci.* 11, 3398–3411.

Moremen, K. W. (1989) *Proc. Natl. Acad. Sci. U.S.A.* 86, 5276–5280.

Neame, P. J., Périn, J. -P., Bonnet, F., Christher, J. E., Jollès, P., and Baker, J. R. (1985) *J. Biol. Chem.* 260, 12402–12404.

Neame, P. J., Christner, J. E., and Baker, J. R. (1986) *J. Biol. Chem.* 261, 3519–3535.

Nishiyama, A., Dahlin, K. J., Prince, J. T., Johnstone, S. R., and Stallcup, W. B. (1991) *J. Cell Biol.* 114, 359–371.

Oakley, R. A., and Tosney, K. W. (1991) *Dev. Biol.* 147, 187–206.

Pearson, W., and Lipman, D. (1988) *Proc. Natl. Acad. Sci. U.S.A.* 85, 2444–2448.

Perides, G., W. S. Lane, D. Andrews, D. Dahl, and A. Bignami. (1989) *J. Biol. Chem.* 264, 5981–5987.

Perkins, S. J., Nealis, A. S., Dunham, D. G., Hardingham, T. E., and Muir, L. H. (1991) *Biochemistry* 30, 10708–10716.

Perris, R., and Johansson, S. (1990) *Dev. Biol.* 137, 1–12

Perris, R., Krotoski, D., Lallier, T., Domingo, C., Sorrell, J. M., and Bronner-Fraser, M. (1991) *Development* 111, 583–599.

Polley, M. J., Phillips, M. L., Wayner, E., Nudelman, E., Singhal, A. K., Hakomori, S. -I., and Paulson, J. C. (1991) *Proc. Nat. Acad. Sci. U.S.A.* 88, 6224–6228.

Preissner, K. T. (1991) *Annu. Rev. Cell Biol.* 7, 275–310.

Rauch, U., Gao, P., Janetzko, A., Flaccus, A., Hilgenberg, L., Tekotte, H., Margolis, R. K., and Margolis, R. U. (1991) *J. Biol. Chem.* 266, 14785–14801.

Ripellino, J. A., M. Bailo, R. U. Margolis, and R. K. Margolis. (1988) *J. Cell Biol.* 106, 845–855.

Ripellino, J. A., R. U. Margolis, and R. K. Margolis. (1989) *J. Cell Biol,* 108, 1899–1907.

Sakurai, T., Ohmi, K., Kurokawa, H., and Nonomura, Y. (1990) *Neurosci.* 38, 743–756.

Saunders, S., Jalkanen, M., O'Farrell, S., and Bernfield, M. (1989) *J. Cell Biol.* 108, 1547–1556.

Schwartz, R. M., and Dayhoff, M. O. (1979) in *Atlas of Protein Sequence and Structure,* Dayhoff, M. O., ed., Vol. 5, National Biomedical Research Foundation, Washington, D.C., pp. 353–358.

Segrest, J. P., and Jackson, R. L. (1972) *Meth. Enzymol.* 28, 54–63.

Sheppard, A. M., Hamilton, S. K., and Pearlman, A. L. (1991) *J. Neurosci.* 11, 3928–3942.

Sithigorngul, P., Stretton, A. O. W., and Cowden, C. (1991) *J. Immunol. Meth.* 141, 23–32.

Snow, D. M., Steindler, D. A., and Silver, J. (1990a) *Dev. Biol.* 138, 359–376.

Snow, D. M., Lemmon, V., Carrino, D. A., Caplan, A. I., and Silver, J. (1990b) *Exp. Neurol.* 109, 111–130.

Snow, D. M., Watanabe, M., Letourneau, P. C., and Silver, J. (1991) *Development* 113, 1473–1485.

Spiess, M. (1990) *Biochemistry* 29, 10009–10018.

Stossel, T. P., Chaponnier, C., Ezzell, R. M., Hartwig, H. J., Janmey, P. A., Kwiatkowski, D. J., Lind, S. E., Smith, D. B., Southwick, F. S., Yin, H. L., and Zaner, K. S. (1985) *Annu. Rev. Cell Biol.* 1, 353–402.

Tanaka, T., Har-El, R., and Tanzer, M. L. (1988) *J. Biol. Chem.* 263, 15831–15835.

Yamada, K. M. (1991) *J. Biol. Chem.* 266, 12809–12812.

Zaremba, S., A. Guimaraes, R. G. Kalb, and S. Hockfield. (1989) *Neuron* 2, 1207–1219.

Zimmermann, D. R., and Ruoslahti, E. (1989) *EMBO J.* 8, 2975–2981.

---

What is claimed is:

1. An isolated neurocan polypeptide, comprising the amino acid sequence of SEQ ID NO:49, or comprising residues 161-355 of SEQ ID NO:49.

2. An isolated polypeptide having the amino acid sequence of a neurocan protein isolated from a mammal, said amino acid sequence having at least 80% identity to the rat neurocan sequence set forth in SEQ ID NO:49.

3. An isolated polypeptide in accordance with claim 2, wherein said mammal is murine, bovine, ovine, porcine, equine, dog, cat or human.

4. An isolated polypeptide in accordance with claim 2, wherein said mammal is a human.

* * * * *

SEQUENCE LISTING ( 1 ) GENERAL INFORMATION:

( i i i ) NUMBER OF SEQUENCES: 49

( 2 ) INFORMATION FOR SEQ ID NO:1:

( i ) SEQUENCE CHARACTERISTICS:
        ( A ) LENGTH: 5191 base pairs
        ( B ) TYPE: nucleic acid
        ( C ) STRANDEDNESS: single -continued ( D ) TOPOLOGY: linear ( i i ) MOLECULE TYPE: DNA ( i x ) FEATURE:
 ( A ) NAME/KEY: CDS
 ( B ) LOCATION: 77..3847

( x i ) SEQUENCE DESCRIPTION: SEQ ID NO:1:

```
AACACCGGAG CCAGGCGTCG CGTCCTTTGT GCCCGGAACC GTGGGGATGT GTCCGCGCTA            60

AGGAGCCAGC TCCAGT ATG GGG GCC GAA TCT GTC TGG GCC TCA GGC CTC              109
               Met Gly Ala Glu Ser Val Trp Ala Ser Gly Leu
                 1               5                    10

CTG GTG CTG TGG CTG CTT CTC CTA GTG TCT GGG GAT CAG GAC ACA CAG            157
Leu Val Leu Trp Leu Leu Leu Leu Val Ser Gly Asp Gln Asp Thr Gln
             15                  20                  25

GAC ACC ACC ACC ACG GAA AAG GGG CTT CAC ATG CTG AAG TCG GGG TCA            205
Asp Thr Thr Thr Thr Glu Lys Gly Leu His Met Leu Lys Ser Gly Ser
             30                  35                  40

GGA CCC ATC CAG GCT GCT TTG GCA GAG TTA GTG GCC CTG CCC TGC TTC            253
Gly Pro Ile Gln Ala Ala Leu Ala Glu Leu Val Ala Leu Pro Cys Phe
         45                  50                  55

TTT ACC CTT CAA CCA CGG CAA AGC CCC CTG GGA GAC ATT CCT CGG ATC            301
Phe Thr Leu Gln Pro Arg Gln Ser Pro Leu Gly Asp Ile Pro Arg Ile
 60              65                  70                  75

AAG TGG ACG AAA GTT CAG ACT GCA TCA GGC CAG CGA CAG GAT TTG CCA            349
Lys Trp Thr Lys Val Gln Thr Ala Ser Gly Gln Arg Gln Asp Leu Pro
                 80                  85                  90

ATC TTG GTG GCC AAA GAC AAT GTG GTG CGT GTG GCC AAG GGC TGG CAG            397
Ile Leu Val Ala Lys Asp Asn Val Val Arg Val Ala Lys Gly Trp Gln
             95                 100                 105

GGA CGG GTG TCA TTG CCT GCC TAT CCC CGG CAC AGA GCC AAT GCT ACA            445
Gly Arg Val Ser Leu Pro Ala Tyr Pro Arg His Arg Ala Asn Ala Thr
         110                 115                 120

CTT CTG TTG GGG CCA CTG CGA GCC AGT GAC TCT GGG CTG TAT CGC TGC            493
Leu Leu Leu Gly Pro Leu Arg Ala Ser Asp Ser Gly Leu Tyr Arg Cys
 125                 130                 135

CAA GTG GTG AAG GGT ATC GAG GAT GAG CAG GAC CTG GTA ACC CTG GAA            541
Gln Val Val Lys Gly Ile Glu Asp Glu Gln Asp Leu Val Thr Leu Glu
140                 145                 150                 155

GTG ACG GGC GTC GTG TTC CAT TAT CGG GCG GCC CGG GAC CGC TAT GCG            589
Val Thr Gly Val Val Phe His Tyr Arg Ala Ala Arg Asp Arg Tyr Ala
                 160                 165                 170

TTG ACC TTC GCT GAG GCC CAG GAG GCT TGT CAC CTG AGC TCC GCT ACC            637
Leu Thr Phe Ala Glu Ala Gln Glu Ala Cys His Leu Ser Ser Ala Thr
             175                 180                 185

ATT GCG GCT CCA AGG CAC CTG CAG GCT GCG TTC GAA GAT GGC TTT GAC            685
Ile Ala Ala Pro Arg His Leu Gln Ala Ala Phe Glu Asp Gly Phe Asp
         190                 195                 200

AAC TGC GAT GCG GGC TGG CTC TCA GAC CGC ACG GTC CGG TAC CCG ATC            733
Asn Cys Asp Ala Gly Trp Leu Ser Asp Arg Thr Val Arg Tyr Pro Ile
 205                 210                 215

ACT CAG TCG CGT CCC GGT TGC TAT GGT GAT CGC AGC AGC CTG CCA GGT            781
Thr Gln Ser Arg Pro Gly Cys Tyr Gly Asp Arg Ser Ser Leu Pro Gly
220                 225                 230                 235

GTC CGG AGC TAC GGG AGA CGC GAC CCG CAG GAA CTC TAC GAT GTC TAC            829
Val Arg Ser Tyr Gly Arg Arg Asp Pro Gln Glu Leu Tyr Asp Val Tyr
                 240                 245                 250

TGC TTT GCC CGC GAG CTA GGG GGT GAA GTC TTT TAC GTG GGC CCC GCC            877
Cys Phe Ala Arg Glu Leu Gly Gly Glu Val Phe Tyr Val Gly Pro Ala
             255                 260                 265
```

| | | | | | | | | | | | | | | | | |
|---|---|---|---|---|---|---|---|---|---|---|---|---|---|---|---|---|
| CGC | CGA | CTG | ACC | CTG | GCG | GGG | GCG | CGG | GCA | CTG | TGT | CAG | CGT | CAG | GGT | 925 |
| Arg | Arg | Leu<br>270 | Thr | Leu | Ala | Gly | Ala<br>275 | Arg | Ala | Leu | Cys | Gln<br>280 | Arg | Gln | Gly | |
| GCA | GCG | CTG | GCC | TCC | GTG | GGA | CAG | TTG | CAC | CTG | GCC | TGG | CAC | GAG | GGC | 973 |
| Ala<br>285 | Ala | Leu | Ala | Ser | Val<br>290 | Gly | Gln | Leu | His | Leu<br>295 | Ala | Trp | His | Glu | Gly | |
| CTG | GAC | CAG | TGC | GAC | CCG | GGC | TGG | CTG | GCA | GAC | GGC | AGC | GTG | CGC | TAC | 1021 |
| Leu<br>300 | Asp | Gln | Cys | Asp<br>305 | Pro | Gly | Trp | Leu | Ala<br>310 | Asp | Gly | Ser | Val | Arg<br>315 | Tyr | |
| CCG | ATC | CAG | ACT | CCA | CGG | CGG | CGT | TGC | GGG | GGC | TCC | GCT | CCA | GGT | GTG | 1069 |
| Pro | Ile | Gln | Thr<br>320 | Pro | Arg | Arg | Arg | Cys | Gly<br>325 | Gly | Ser | Ala | Pro | Gly<br>330 | Val | |
| CGC | ACA | GTG | TAC | CGC | TTC | GCC | AAC | CGC | ACT | GGC | TTT | CCT | GCG | CCA | GGA | 1117 |
| Arg | Thr | Val | Tyr<br>335 | Arg | Phe | Ala | Asn | Arg<br>340 | Thr | Gly | Phe | Pro | Ala<br>345 | Pro | Gly | |
| GCC | CGC | TTC | GAC | GCC | TAC | TGC | TTC | CGA | GCT | CAT | CAC | CAT | ACA | CCA | CAA | 1165 |
| Ala | Arg | Phe<br>350 | Asp | Ala | Tyr | Cys | Phe<br>355 | Arg | Ala | His | His | His<br>360 | Thr | Pro | Gln | |
| CGT | GGG | GAC | TCC | GAG | ATC | CCC | TCA | TCT | GGA | GAT | GAG | GGG | GAG | ATT | GTG | 1213 |
| Arg | Gly<br>365 | Asp | Ser | Glu | Ile | Pro<br>370 | Ser | Ser | Gly | Asp | Glu<br>375 | Gly | Glu | Ile | Val | |
| TCA | GCA | GAG | GGG | CCG | CCA | GCC | CCA | GAA | CTA | AAG | CCC | AGA | TTG | GGG | GAG | 1261 |
| Ser<br>380 | Ala | Glu | Gly | Pro | Pro<br>385 | Ala | Pro | Glu | Leu | Lys<br>390 | Pro | Arg | Leu | Gly | Glu<br>395 | |
| CAG | GAG | GTG | ATA | ACA | CCT | GAC | TTC | CAG | GAA | CCT | CTC | GTA | TCC | AGT | GGA | 1309 |
| Gln | Glu | Val | Ile | Thr<br>400 | Pro | Asp | Phe | Gln | Glu<br>405 | Pro | Leu | Val | Ser | Ser<br>410 | Gly | |
| GAA | GAT | GAA | CCC | CTA | GAT | TTG | ACA | AGG | ACA | CAA | GCA | TCT | CAG | GAG | ACG | 1357 |
| Glu | Asp | Glu | Pro<br>415 | Leu | Asp | Leu | Thr | Arg<br>420 | Thr | Gln | Ala | Ser | Gln<br>425 | Glu | Thr | |
| CTC | GCC | TCT | ACC | CCA | GGG | GGT | CCC | ACA | CTG | GCT | TCA | TGG | CTG | CTT | ACA | 1405 |
| Leu | Ala | Ser<br>430 | Thr | Pro | Gly | Gly | Pro<br>435 | Thr | Leu | Ala | Ser | Trp<br>440 | Leu | Leu | Thr | |
| GGT | GTC | ACA | AGC | TCC | ACG | GGT | GTC | CCC | AGC | CCC | AGC | AGC | CTG | GGA | GTA | 1453 |
| Gly | Val | Thr<br>445 | Ser | Ser | Thr | Gly<br>450 | Val | Pro | Ser | Pro | Ser<br>455 | Ser | Leu | Gly | Val | |
| GAC | ATG | GAA | GAG | ACA | ACA | CCC | TCA | GGC | ACA | CAG | GTA | GCC | CCC | ACC | CCC | 1501 |
| Asp<br>460 | Met | Glu | Glu | Thr | Thr<br>465 | Pro | Ser | Gly | Thr | Gln<br>470 | Val | Ala | Pro | Thr | Pro<br>475 | |
| ACA | ATG | AGG | AGG | GGC | CGC | TTT | AAA | GGG | TTG | AAT | GGT | CGA | CAC | TTC | CAG | 1549 |
| Thr | Met | Arg | Arg | Gly<br>480 | Arg | Phe | Lys | Gly | Leu<br>485 | Asn | Gly | Arg | His | Phe<br>490 | Gln | |
| CAA | CAG | GGC | CCA | GAA | GAC | CAG | CTT | CTG | GAG | GCA | GCA | GAG | GCC | AGT | GCC | 1597 |
| Gln | Gln | Gly | Pro<br>495 | Glu | Asp | Gln | Leu | Leu<br>500 | Glu | Ala | Ala | Glu | Ala<br>505 | Ser | Ala | |
| CAG | CCT | CCC | ACC | CTG | GAA | GTT | ACT | GCT | GAC | CAC | ATG | GGG | CCT | TCT | GCA | 1645 |
| Gln | Pro | Pro<br>510 | Thr | Leu | Glu | Val | Thr<br>515 | Ala | Asp | His | Met | Gly<br>520 | Pro | Ser | Ala | |
| GCC | ACA | GAG | GCC | TTG | GAG | AGT | GAC | CAG | AGC | CAC | AGT | CCT | TGG | GCC | ATT | 1693 |
| Ala | Thr<br>525 | Glu | Ala | Leu | Glu<br>530 | Ser | Asp | Gln | Ser | His<br>535 | Ser | Pro | Trp | Ala | Ile | |
| CTG | ACC | AAT | GAA | GTG | GAT | GTG | CCA | GGG | GCA | GGC | TCT | CTT | GGC | AGC | AGG | 1741 |
| Leu<br>540 | Thr | Asn | Glu | Val | Asp<br>545 | Val | Pro | Gly | Ala | Gly<br>550 | Ser | Leu | Gly | Ser | Arg<br>555 | |
| AGT | CTC | CCA | GAG | TCC | CGG | AAG | TGG | TCC | CCG | TCG | CTG | ATT | TCA | CCC | AGT | 1789 |
| Ser | Leu | Pro | Glu<br>560 | Ser | Arg | Lys | Trp | Ser<br>565 | Pro | Ser | Leu | Ile | Ser<br>570 | Pro | Ser | |
| ACT | GTC | CCG | AGC | ACT | GAC | AGT | ACT | CCT | GGC | CTG | AAG | CCA | GGG | GCA | GAT | 1837 |
| Thr | Val | Pro | Ser<br>575 | Thr | Asp | Ser | Thr | Pro<br>580 | Gly | Leu | Lys | Pro | Gly<br>585 | Ala | Asp | |

| | | | | | | | | | | | | | | | | |
|---|---|---|---|---|---|---|---|---|---|---|---|---|---|---|---|---|
| GAG | GCC | CCT | GGT | GTG | AAG | TCA | GCC | ATC | CAC | CAC | CCA | CCC | TGG | TTG | CCC | 1885 |
| Glu | Ala | Pro | Gly | Val | Lys | Ser | Ala | Ile | His | His | Pro | Pro | Trp | Leu | Pro | |
| | | | 590 | | | | 595 | | | | 600 | | | | | |
| TCA | GAA | CCC | GCT | GTC | CCA | TCC | TCC | ATT | CCC | TCA | GAG | GCC | CTA | AGT | GCT | 1933 |
| Ser | Glu | Pro | Ala | Val | Pro | Ser | Ser | Ile | Pro | Ser | Glu | Ala | Leu | Ser | Ala | |
| | 605 | | | | | 610 | | | | | 615 | | | | | |
| GTC | TCC | CTA | CAG | GCA | TCC | CCT | GGT | GAT | GGC | TCT | CCA | GAC | TTC | CCC | ATT | 1981 |
| Val | Ser | Leu | Gln | Ala | Ser | Pro | Gly | Asp | Gly | Ser | Pro | Asp | Phe | Pro | Ile | |
| 620 | | | | | 625 | | | | | 630 | | | | | 635 | |
| GTA | GCC | ATG | CTT | CGA | GCC | CCC | AAA | CTG | TGG | CTT | CTG | CCA | CAC | TCT | ACA | 2029 |
| Val | Ala | Met | Leu | Arg | Ala | Pro | Lys | Leu | Trp | Leu | Leu | Pro | His | Ser | Thr | |
| | | | | 640 | | | | | 645 | | | | | 650 | | |
| CTC | GTC | CCG | AAT | GTG | TCC | CCA | ATC | CCA | CTC | TCC | CCA | GCT | TCT | CCA | CTC | 2077 |
| Leu | Val | Pro | Asn | Val | Ser | Pro | Ile | Pro | Leu | Ser | Pro | Ala | Ser | Pro | Leu | |
| | | | 655 | | | | 660 | | | | | 665 | | | | |
| CCC | TCC | TCG | GTC | CCA | GAA | GAA | CAG | GCT | GTC | AGA | CCT | GTC | AGC | TTT | GGA | 2125 |
| Pro | Ser | Ser | Val | Pro | Glu | Glu | Gln | Ala | Val | Arg | Pro | Val | Ser | Phe | Gly | |
| | | 670 | | | | | 675 | | | | | 680 | | | | |
| GCA | GAA | GAC | CCC | GAG | ACC | CCA | TTT | CAG | ACC | ACC | ATG | GCT | GCC | CCA | GGT | 2173 |
| Ala | Glu | Asp | Pro | Glu | Thr | Pro | Phe | Gln | Thr | Thr | Met | Ala | Ala | Pro | Gly | |
| | 685 | | | | | 690 | | | | | 695 | | | | | |
| GAA | GCC | AGC | CAC | GGA | TCC | CCT | GAG | GCA | GAC | TCC | ATA | GAA | ATC | GAG | GGG | 2221 |
| Glu | Ala | Ser | His | Gly | Ser | Pro | Glu | Ala | Asp | Ser | Ile | Glu | Ile | Glu | Gly | |
| 700 | | | | | 705 | | | | | 710 | | | | | 715 | |
| ATC | AGC | TCC | ATG | CAG | GCT | ACA | AAG | CAC | CCC | ATC | TCT | GGC | CCA | TGG | GCT | 2269 |
| Ile | Ser | Ser | Met | Gln | Ala | Thr | Lys | His | Pro | Ile | Ser | Gly | Pro | Trp | Ala | |
| | | | | 720 | | | | | 725 | | | | | 730 | | |
| TCT | TTG | GAC | TCC | AGT | AAT | GTG | ACA | GTG | AAT | CCT | GTC | CCT | TCT | GAT | GCT | 2317 |
| Ser | Leu | Asp | Ser | Ser | Asn | Val | Thr | Val | Asn | Pro | Val | Pro | Ser | Asp | Ala | |
| | | | 735 | | | | 740 | | | | | 745 | | | | |
| GGC | ATC | CTA | GGG | ACT | GAG | TCT | GGG | GTC | TTG | GAC | TTA | CCA | GGG | AGT | CCC | 2365 |
| Gly | Ile | Leu | Gly | Thr | Glu | Ser | Gly | Val | Leu | Asp | Leu | Pro | Gly | Ser | Pro | |
| | | 750 | | | | | 755 | | | | | 760 | | | | |
| ACA | TCA | GAC | GGA | CAG | GCC | ACT | GTG | GAC | ATG | GTG | CTG | GCC | ACC | TGG | CTA | 2413 |
| Thr | Ser | Asp | Gly | Gln | Ala | Thr | Val | Asp | Met | Val | Leu | Ala | Thr | Trp | Leu | |
| | 765 | | | | | 770 | | | | | 775 | | | | | |
| CCA | CTG | CCT | GGC | CAC | GGA | CTG | GAC | ACT | GGC | TCC | CAG | TCC | ACA | CCC | ATG | 2461 |
| Pro | Leu | Pro | Gly | His | Gly | Leu | Asp | Thr | Gly | Ser | Gln | Ser | Thr | Pro | Met | |
| 780 | | | | | 785 | | | | | 790 | | | | | 795 | |
| GAA | GCC | CAT | GGA | GTA | ACC | ATG | AGT | GTG | GAA | CCT | ACA | GTG | GCT | TTG | GAA | 2509 |
| Glu | Ala | His | Gly | Val | Thr | Met | Ser | Val | Glu | Pro | Thr | Val | Ala | Leu | Glu | |
| | | | | 800 | | | | | 805 | | | | | 810 | | |
| GGA | GGT | GCC | ACC | AAA | GAC | CCA | ATG | GAG | GCC | ACC | ATG | GAT | GTG | GTC | CCC | 2557 |
| Gly | Gly | Ala | Thr | Lys | Asp | Pro | Met | Glu | Ala | Thr | Met | Asp | Val | Val | Pro | |
| | | | 815 | | | | 820 | | | | | 825 | | | | |
| AGC | ACT | GTT | GAT | GCC | ACT | TCG | GGG | TCT | GAA | CCC | AAA | AGT | TCC | ATT | TCT | 2605 |
| Ser | Thr | Val | Asp | Ala | Thr | Ser | Gly | Ser | Glu | Pro | Lys | Ser | Ser | Ile | Ser | |
| | | 830 | | | | | 835 | | | | | 840 | | | | |
| AGC | ACC | CAT | GTG | GTT | GTG | ACT | GCA | GCT | GGG | GAC | CAG | GGC | ACA | CCC | ACA | 2653 |
| Ser | Thr | His | Val | Val | Val | Thr | Ala | Ala | Gly | Asp | Gln | Gly | Thr | Pro | Thr | |
| | 845 | | | | | 850 | | | | | 855 | | | | | |
| CTG | ACC | CCT | ACA | AGC | TCT | GAA | GGT | CAG | GTG | GTG | GCC | CAG | GAG | TCA | CTG | 2701 |
| Leu | Thr | Pro | Thr | Ser | Ser | Glu | Gly | Gln | Val | Val | Ala | Gln | Glu | Ser | Leu | |
| 860 | | | | | 865 | | | | | 870 | | | | | 875 | |
| GGA | ACC | CTC | ACC | AGT | CTG | CCT | TCT | CAT | CCC | TGG | TCA | TCT | CTG | GCC | TCC | 2749 |
| Gly | Thr | Leu | Thr | Ser | Leu | Pro | Ser | His | Pro | Trp | Ser | Ser | Leu | Ala | Ser | |
| | | | | 880 | | | | | 885 | | | | | 890 | | |
| AGC | ATG | GAC | GAA | GTG | GCC | TCG | GTT | TCC | TCA | GGA | GAA | CCC | ACA | AGG | TTG | 2797 |
| Ser | Met | Asp | Glu | Val | Ala | Ser | Val | Ser | Ser | Gly | Glu | Pro | Thr | Arg | Leu | |
| | | | 895 | | | | | 900 | | | | | 905 | | | |

| | | | | | | | | | | | | | | | | |
|---|---|---|---|---|---|---|---|---|---|---|---|---|---|---|---|---|
| TGG | GAC | ATC | CCC | AGC | ACT | CTG | ATA | CCT | GTG | TCC | TTG | GGC | TTG | GAT | GAA | 2845 |
| Trp | Asp | Ile 910 | Pro | Ser | Thr | Leu | Ile 915 | Pro | Val | Ser | Leu | Gly 920 | Leu | Asp | Glu | |
| TCA | GAC | CTG | AAG | GTT | GTG | GCT | GAG | AGC | CCA | GGC | TTG | GAG | GGC | TTC | TGG | 2893 |
| Ser | Asp 925 | Leu | Lys | Val | Val | Ala 930 | Glu | Ser | Pro | Gly | Leu 935 | Glu | Gly | Phe | Trp | |
| GAA | GAG | GTG | GCC | AGT | GGG | CAG | GAA | GAC | CCC | ACG | GAT | CCC | TGC | GAG | AAC | 2941 |
| Glu 940 | Glu | Val | Ala | Ser | Gly 945 | Gln | Glu | Asp | Pro | Thr 950 | Asp | Pro | Cys | Glu | Asn 955 | |
| AAC | CCT | TGT | CTG | CAC | GGG | GGC | ACC | TGC | CGC | ACA | AAT | GGC | ACC | ATG | TAC | 2989 |
| Asn | Pro | Cys | Leu | His 960 | Gly | Gly | Thr | Cys | Arg 965 | Thr | Asn | Gly | Thr | Met 970 | Tyr | |
| GGC | TGT | AGT | TGT | GAT | CAG | GGC | TAT | GCT | GGG | GAG | AAT | TGT | GAA | ATT | GAC | 3037 |
| Gly | Cys | Ser | Cys 975 | Asp | Gln | Gly | Tyr | Ala 980 | Gly | Glu | Asn | Cys | Glu 985 | Ile | Asp | |
| ATT | GAT | GAC | TGC | TTG | TGC | AGC | CCT | TGT | GAG | AAT | GGG | GGT | ACC | TGC | ATT | 3085 |
| Ile | Asp | Asp 990 | Cys | Leu | Cys | Ser | Pro 995 | Cys | Glu | Asn | Gly | Gly 1000 | Thr | Cys | Ile | |
| GAT | GAG | GTG | AAT | GGT | TTC | ATC | TGC | CTC | TGT | CTC | CCC | AGC | TAT | GGG | GGC | 3133 |
| Asp | Glu | Val | Asn 1005 | Gly | Phe | Ile | Cys | Leu 1010 | Cys | Leu | Pro | Ser | Tyr 1015 | Gly | Gly | |
| AAC | CTG | TGC | GAG | AAG | GAC | ACA | GAA | GGA | TGC | GAC | CGT | GGC | TGG | CAC | AAA | 3181 |
| Asn | Leu | Cys 1020 | Glu | Lys | Asp | Thr | Glu 1025 | Gly | Cys | Asp | Arg | Gly 1030 | Trp | His | Lys 1035 | |
| TTC | CAG | GGC | CAC | TGC | TAC | CGC | TAC | TTT | GCT | CAT | CGG | CGG | GCC | TGG | GAG | 3229 |
| Phe | Gln | Gly | His | Cys 1040 | Tyr | Arg | Tyr | Phe | Ala 1045 | His | Arg | Arg | Ala | Trp 1050 | Glu | |
| GAC | GCA | GAG | AGA | GAC | TGC | AGG | CGC | CGA | GCC | GGC | CAC | CTG | ACA | AGT | GTC | 3277 |
| Asp | Ala | Glu | Arg | Asp 1055 | Cys | Arg | Arg | Arg | Ala 1060 | Gly | His | Leu | Thr | Ser 1065 | Val | |
| CAC | TCC | CCA | GAA | GAG | CAC | AAG | TTT | ATT | AAC | AGT | TTT | GGA | CAC | GAG | AAT | 3325 |
| His | Ser | Pro | Glu 1070 | Glu | His | Lys | Phe | Ile 1075 | Asn | Ser | Phe | Gly | His 1080 | Glu | Asn | |
| TCA | TGG | ATT | GGC | CTG | AAT | GAC | AGG | ACA | GTA | GAG | AGG | GAC | TTC | CAG | TGG | 3373 |
| Ser | Trp | Ile 1085 | Gly | Leu | Asn | Asp | Arg 1090 | Thr | Val | Glu | Arg | Asp 1095 | Phe | Gln | Trp | |
| ACA | GAC | AAC | ACA | GGA | CTG | CAA | TAT | GAG | AAC | TGG | AGA | GAG | AAG | CAG | CCG | 3421 |
| Thr | Asp | Asn | Thr 1100 | Gly | Leu | Gln | Tyr | Glu 1105 | Asn | Trp | Arg | Glu | Lys 1110 | Gln | Pro 1115 | |
| GAT | AAT | TTC | TTC | GCA | GGT | GGG | GAG | GAT | TGT | GTG | GTG | ATG | GTG | GCG | CAT | 3469 |
| Asp | Asn | Phe | Phe | Ala 1120 | Gly | Gly | Glu | Asp | Cys 1125 | Val | Val | Met | Val | Ala 1130 | His | |
| GAG | AAT | GGA | CGC | TGG | AAT | GAT | GTC | CCC | TGT | AAC | TAC | AAC | CTC | CCC | TAC | 3517 |
| Glu | Asn | Gly | Arg | Trp 1135 | Asn | Asp | Val | Pro | Cys 1140 | Asn | Tyr | Asn | Leu | Pro 1145 | Tyr | |
| GTC | TGC | AAG | AAG | GGT | ACA | GTG | CTG | TGT | GGG | CCC | CCT | CCA | GCA | GTG | GAG | 3565 |
| Val | Cys | Lys | Lys | Gly 1150 | Thr | Val | Leu | Cys | Gly 1155 | Pro | Pro | Pro | Ala | Val 1160 | Glu | |
| AAT | GCC | TCT | CTT | GTT | GGT | GTG | CGC | AAG | GTC | AAG | TAC | AAT | GTC | CAT | GCC | 3613 |
| Asn | Ala | Ser | Leu | Val 1165 | Gly | Val | Arg | Lys | Val 1170 | Lys | Tyr | Asn | Val | His 1175 | Ala | |
| ACT | GTG | CGA | TAC | CAG | TGT | GAT | GAA | GGA | TTC | TCC | CAG | CAC | CAT | GTG | GCT | 3661 |
| Thr | Val 1180 | Arg | Tyr | Gln | Cys | Asp 1185 | Glu | Gly | Phe | Ser | Gln 1190 | His | His | Val | Ala 1195 | |
| ACC | ATC | CGA | TGC | CGA | AGC | AAT | GGG | AAG | TGG | GAC | CGG | CCT | CAG | ATT | GTG | 3709 |
| Thr | Ile | Arg | Cys | Arg 1200 | Ser | Asn | Gly | Lys | Trp 1205 | Asp | Arg | Pro | Gln | Ile 1210 | Val | |
| TGC | ACC | AAG | CCC | AGG | CGG | TCA | CAT | CGG | ATG | CGT | CGA | CAC | CAC | CAC | CAT | 3757 |
| Cys | Thr | Lys | Pro | Arg 1215 | Arg | Ser | His | Arg | Met 1220 | Arg | Arg | His | His | His 1225 | His | |

| | | | | | | | | | | | | | | |
|---|---|---|---|---|---|---|---|---|---|---|---|---|---|---|
| CCA | CAC | CGG | CAT | CAC | AAG | CCA | CGC | AAG | GAG | CAC | AGA | AAA | CAC | AAG | AGA |
| Pro | His | Arg | His | His | Lys | Pro | Arg | Lys | Glu | His | Arg | Lys | His | Lys | Arg |
| | | 1230 | | | | | 1235 | | | | | 1240 | | | |

3805

| | | | | | | | | | | | |
|---|---|---|---|---|---|---|---|---|---|---|---|
| CAC | CCA | GCG | GAA | GAC | TGG | GAG | AAA | GAT | GAA | GGG | GAT | TTC | TGC |
| His | Pro | Ala | Glu | Asp | Trp | Glu | Lys | Asp | Glu | Gly | Asp | Phe | Cys |
| | 1245 | | | | | 1250 | | | | | 1255 | | |

3847

```
TAACGATCCA GACTAATCAA GCACAAGCTC CCACACCTCC TCCAGAGCAT TCCCCTGGGG      3907
ACCCAGAACC CAGACAACCA CCAGAGAGAG GGTGGGGACA CCCTGGAGCC CCACACCCCT      3967
GCAGTCGGTC CTCTGTACAA AGCTCAGATC ACCCTCTCCT TCCTTACTGA GGTCCTCCTG      4027
GCAGGGGTGG CGGGACCTGA GAGGCCATTC TGGTCTGGCT GAGCCCTTAG GATTACTTCC      4087
CAGCTGTCAA AGGGAGTCTC GAAGTCTGTA TCCATGAGGG GCAAACAGTA TGTCTGTGGG      4147
CGCTGGGTAG TGACTTTCAC ACCAGAGATT CAGGCTTCGT AAACAGCGGA CTATACTGAA      4207
TCCATGGCAA ACCTTTGGTT AAAGTCACTG TATTTGAGTG GAGGACCAGC AGAGCAAACA      4267
GGATGCTCTG TGGTCCCCTG GGATCCCCTA AGGGCAGGCT TCCATCCCTC CGTCTTTCTT      4327
TTTTCCCTTT CTCCTTCCTC CCTCTCAATT CCAACACTGT CAGGACTCAA CCTAGGCTGG      4387
GCTTGAACTG ACTATTGTAG AAGGATGTCC TTGAAGTCTC AATCCTCCTG CCCCTGTGCC      4447
ACCATGCCTA CCTGGTTTAT TTGGTGCTGG ACATGGAACC CAGCGCTGGG CAAGTGCTCT      4507
CTCTACTAAC CAGCTCTGGT CTTTGGTCTT GGTGCAGACC ACTAAATCTA GTGTGGGAAC      4567
TCTTGTATAT TGAATTTTAG TGATGTCTCT TAGCCTGGCC TCCGTGGCTT CCTAGGGGAG      4627
GTTCCTCAGA GCAATGGGGG TGGGGAGGGT TACTCTATTG CTGACTCCCC ACGTCTAGTG      4687
CAGCGCTGAG ATCTGGTGGT TCTATTTTGG GTTGTTTTTG TTTTGAGACA GGGCCTCACT      4747
GTGCAGCTCT AGCTGGCCTG GAACTTGCTA TGTAGACCAG GCTAGCCTGG AACTCAGCGA      4807
TCTGTCTGCC TCTGCCTCTC TAGTTACTAT GCCCAGCCTT CTTTGTTTT ACTGACCTAG      4867
GATCTCTATA GCCCAGGCTG GGTTTCAGTC CACAGCGATC AGATCCTTTC TCAACCACCT      4927
AAGAGCTGAG GTGACAGGCA CACCATCACG TGTGGCACTT TTGTGGGTGT GTGATGGCAA      4987
ATCTCCCACA CCCATGTGTC CAGACGTGAG ACAGCAGAGT AGAGTGTACT GGATGCTGCT      5047
GTATCCCTCT CCTCCATCTC TCAGGGAGAC AGACAACCTT CTGCCCGGAC CAAGATGCTG      5107
CCATGTTTTC TAACCCAGAG CCTGTCTTTA CTAAAACCCT CTCAGCAGAC CTCAGTAAAT      5167
CTCCTGCCTC AGATCCCGGA ATTC                                             5191
```

( 2 ) INFORMATION FOR SEQ ID NO:2:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Leu Arg Ala Pro Lys Leu Xaa Leu Leu Pro Xaa Xaa Xaa Leu Val Pro
1               5                   10                  15
Asn Val
```

( 2 ) INFORMATION FOR SEQ ID NO:3:

( i ) SEQUENCE CHARACTERISTICS:
        ( A ) LENGTH: 24 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:3:

```
Phe Trp Glu Glu Val Ala Xaa Gly Gln Glu Asp Pro Thr Asp Pro
1               5                   10                  15

Glu Asn Asn Asn Xaa Xaa Xaa Glu
                20
```

(2) INFORMATION FOR SEQ ID NO:4:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Val Val Ala Glu Xaa Pro Gly Leu Glu Gly Phe Xaa Glu Glu Val Ala
1               5                   10                  15

Xaa Xaa
```

(2) INFORMATION FOR SEQ ID NO:5:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Asp Leu Lys Val Val Ala Glu Xaa Pro Gly Leu Glu Gly Phe Trp Glu
1               5                   10                  15

Glu Val Ala Xaa Gly Gln Glu Asp Pro Thr Asp Pro Xaa Glu Asn Asn
                20                  25                  30

Pro Xaa Leu Glu Gly Gly
            35
```

(2) INFORMATION FOR SEQ ID NO:6:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Tyr Xaa Xaa Xaa Xaa Asp Gln Gly Tyr Ala Gly Glu Asn Xaa Glu Ile
1               5                   10                  15

Asp Ile Asp Asp Asp Leu Leu Leu Pro Pro Glu Asn Gly Xaa
                20                  25                  30
```

(2) INFORMATION FOR SEQ ID NO:7:

(i) SEQUENCE CHARACTERISTICS:
        (A) LENGTH: 37 amino acids
        (B) TYPE: amino acid
        (C) STRANDEDNESS: single
        (D) TOPOLOGY: linear ( i i ) MOLECULE TYPE: peptide ( x i ) SEQUENCE DESCRIPTION: SEQ ID NO:7:

Val Ala His Glu Asn Gly Xaa Xaa Asn Asp Val Pro Xaa Asn Tyr Asn
1               5                   10                  15

Leu Pro Tyr Val Xaa Lys Lys Gly Thr Val Leu Xaa Gly Pro Pro Pro
            20                  25                  30

Ala Val Val His Ala
            35

( 2 ) INFORMATION FOR SEQ ID NO:8:

( i ) SEQUENCE CHARACTERISTICS:
( A ) LENGTH: 48 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:8:

Val Ala His Glu Asn Gly Arg Trp Asn Asp Val Pro Cys Asn Tyr Asn
1               5                   10                  15

Leu Pro Tyr Val Xaa Lys Lys Gly Thr Val Leu Xaa Gly Pro Pro Pro
            20                  25                  30

Ala Val Xaa Asn Ala Lys Leu Val Gly Val Xaa Lys Xaa Xaa Tyr Asn
            35                  40                  45

( 2 ) INFORMATION FOR SEQ ID NO:9:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA ( i x ) FEATURE:
( D ) OTHER INFORMATION:/note all base positions
designated with an "N" are inosines ( x i ) SEQUENCE DESCRIPTION: SEQ ID NO:9:

GGACTGCAGG ATCCNGGN Y T NGGNARGGNT T Y TGGGARGA RG    42

( 2 ) INFORMATION FOR SEQ ID NO:10:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: DNA ( i x ) FEATURE:
( D ) OTHER INFORMATION:/note all base positions
designated with an "N" are inosines ( x i ) SEQUENCE DESCRIPTION: SEQ ID NO:10:

TACGTCGACA AGCTTRTART TRCANGGNAC RTCRTTCC    38

( 2 ) INFORMATION FOR SEQ ID NO:11:

( i ) SEQUENCE CHARACTERISTICS:
( A ) LENGTH: 12 amino acids
( B ) TYPE: amino acid
( C ) STRANDEDNESS: single ( D ) TOPOLOGY: linear ( i i ) MOLECULE TYPE: peptide ( x i ) SEQUENCE DESCRIPTION: SEQ ID NO:11:

```
Asp Gln Asp Thr Gln Asp Thr Thr Thr Thr Glu Lys
1               5                   10
```

( 2 ) INFORMATION FOR SEQ ID NO:12:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Leu Lys Ser Gly Ser Gly Pro Ile Gln Ala Ala Leu Ala Glu Leu Val
1               5                   10                  15

Ala Leu Pro Xaa Phe Phe Thr Leu Gln Pro Arg Gln
            20                  25
```

( 2 ) INFORMATION FOR SEQ ID NO:13:

( i ) SEQUENCE CHARACTERISTICS:
        ( A ) LENGTH: 39 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Ser Gly Ser Gly Pro Ile Gln Ala Ala Leu Ala Glu Leu Val Ala Leu
1               5                   10                  15

Pro Xaa Phe Phe Thr Leu Gln Pro Arg Gln Ser Pro Leu Gly Asp Ile
        20                  25                  30

Pro Arg Ile Lys Trp Thr Lys
            35
```

( 2 ) INFORMATION FOR SEQ ID NO:14:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Val Ser Leu Pro Ala Tyr Pro Arg
1               5
```

( 2 ) INFORMATION FOR SEQ ID NO:15:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Gly Ile Glu Asp Glu Gln Asp Leu Val Thr Leu Glu Val Thr Gly Val
```

(2) INFORMATION FOR SEQ ID NO:16:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Glu Leu Gly Gly Glu Val Phe Tyr Val Gly Pro Ala Arg
 1               5                  10
```

Val Phe His Tyr Arg
     20

(2) INFORMATION FOR SEQ ID NO:16:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Glu Leu Gly Gly Glu Val Phe Tyr Val Gly Pro Ala Arg
 1               5                  10
```

(2) INFORMATION FOR SEQ ID NO:17:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Gln Gly Ala Ala Leu Ala Ser Val Gly Gln Leu His Leu Ala Trp His
 1               5                  10                  15
Glu Gly Leu Asp Gln Cys Asp Pro Gly Trp Leu Ala Asp
                20                  25
```

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

```
CTGCAGGATC CACAGTTTGG GGGCTCGAAG                              30
```

(2) INFORMATION FOR SEQ ID NO:19:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:/note all base positions
        designated with an "N" are inosines (xi) SEQUENCE DESCRIPTION: SEQ ID NO:19:

```
CCGCGGATCC NATNCARGCN GCN Y TNGCNG AR Y TNGTNGC               40
```

(2) INFORMATION FOR SEQ ID NO:20:

(i) SEQUENCE CHARACTERISTICS:
        (A) LENGTH: 34 base pairs
        (B) TYPE: nucleic acid ( C ) STRANDEDNESS: single
( D ) TOPOLOGY: linear ( i i ) MOLECULE TYPE: DNA ( i x ) FEATURE:
( D ) OTHER INFORMATION:/noteall base positions designated with an "N" are inosines ( x i ) SEQUENCE DESCRIPTION: SEQ ID NO:20:

CTTAAGCTTG RTCNGCNARC CANCCNGCRT CRCA                    34

( 2 ) INFORMATION FOR SEQ ID NO:21:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:21:

CTGCTTCTTT ACCCTTCAAC CAC                                23

( 2 ) INFORMATION FOR SEQ ID NO:22:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:22:

AGTTGTCAAA GCCATCTTCG AAC                                23

( 2 ) INFORMATION FOR SEQ ID NO:23:

( i ) SEQUENCE CHARACTERISTICS:
( A ) LENGTH: 49 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:23:

Phe His Tyr Arg Ala Ala Arg Asp Arg Tyr Ala Leu Thr Phe Ala Glu
1               5                   10                  15

Ala Gln Glu Ala Cys His Leu Ser Ser Ala Thr Ile Ala Ala Pro Arg
            20              25                  30

His Leu Gln Ala Ala Phe Glu Asp Gly Phe Asp Asn Cys Asp Ala Gly
        35              40                  45

Trp ( 2 ) INFORMATION FOR SEQ ID NO:24:

( i ) SEQUENCE CHARACTERISTICS:
( A ) LENGTH: 46 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:24:

```
       Phe   Tyr   Val   Gly   Pro   Ala   Arg   Arg   Leu   Thr   Leu   Ala   Gly   Ala   Arg   Ala
       1                       5                             10                            15

Leu   Cys   Gln   Arg   Gln   Gly   Ala   Ala   Leu   Ala   Ser   Val   Gly   Gln   Leu   His
                         20                            25                            30

Leu   Ala   Trp   His   Glu   Gly   Leu   Asp   Gln   Cys   Asp   Pro   Gly   Trp
                         35                            40                            45
```

( 2 ) INFORMATION FOR SEQ ID NO:25:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

```
       Leu   Ser   Asp   Arg   Thr   Val   Arg   Tyr   Pro   Ile   Thr   Gln   Ser   Arg   Pro   Gly
       1                       5                             10                            15

Cys   Tyr   Gly   Asp   Arg   Ser   Ser   Leu   Pro   Gly   Val   Arg   Ser   Tyr   Gly   Arg
                         20                            25                            30

Arg   Asp   Pro   Gln   Glu   Leu   Tyr   Asp   Val   Tyr   Cys   Phe
                         35                            40
```

( 2 ) INFORMATION FOR SEQ ID NO:26:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

```
       Leu   Ala   Asp   Gly   Ser   Val   Arg   Tyr   Pro   Ile   Gln   Thr   Pro   Arg   Arg   Arg
       1                       5                             10                            15

Cys   Gly   Gly   Ser   Ala   Pro   Gly   Val   Arg   Thr   Val   Tyr   Arg   Phe   Ala   Asn
                         20                            25                            30

Arg   Thr   Gly   Phe   Pro   Ala   Pro   Gly   Ala   Arg   Phe   Asp   Ala   Tyr   Cys   Phe
                         35                            40                            45
```

( 2 ) INFORMATION FOR SEQ ID NO:27:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

```
       Glu   Ile   Pro   Ser   Ser   Gly   Asp   Glu
       1                       5
```

( 2 ) INFORMATION FOR SEQ ID NO:28:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide (x i) SEQUENCE DESCRIPTION: SEQ ID NO:28:

Glu Pro Leu Val Ser Ser Gly Glu Asp Glu
1               5                   10

(2) INFORMATION FOR SEQ ID NO:29:

(i) SEQUENCE CHARACTERISTICS:
       (A) LENGTH: 5 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:29:

Asp Gly Ser Pro Asp
1               5

(2) INFORMATION FOR SEQ ID NO:30:

(i) SEQUENCE CHARACTERISTICS:
       (A) LENGTH: 6 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:30:

Glu Ser Gly Val Leu Asp
1               5

(2) INFORMATION FOR SEQ ID NO:31:

(i) SEQUENCE CHARACTERISTICS:
       (A) LENGTH: 7 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:31:

Asp Ala Thr Ser Gly Ser Glu
1               5

(2) INFORMATION FOR SEQ ID NO:32:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:32:

Asp Glu Val Ala Ser Val Ser Ser Gly Glu
1               5                   10

(2) INFORMATION FOR SEQ ID NO:33:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide ( x i ) SEQUENCE DESCRIPTION: SEQ ID NO:33:

Glu Glu Val Ala Ser Gly Gln Glu Asp
1               5

( 2 ) INFORMATION FOR SEQ ID NO:34:

( i ) SEQUENCE CHARACTERISTICS:
       ( A ) LENGTH: 52 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:34:

Leu Trp Val Gly Thr Gly Ala Ser Glu Ala Glu Lys Thr Gly Ala Gln
1               5                   10                  15

Glu Leu Leu Arg Val Leu Arg Ala Gln Pro Val Gln Val Ala Glu Gly
                20                  25                  30

Ser Glu Pro Asp Gly Phe Trp Glu Ala Leu Gly Gly Lys Ala Ala Tyr
            35                  40                  45

Arg Thr Ser Pro
        50

( 2 ) INFORMATION FOR SEQ ID NO:35:

( i ) SEQUENCE CHARACTERISTICS:
       ( A ) LENGTH: 46 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:35:

Leu Trp Asp Ile Pro Ser Thr Leu Ile Pro Val Ser Leu Gly Leu Asp
1               5                   10                  15

Glu Ser Asp Leu Lys Val Val Ala Glu Ser Pro Gly Leu Glu Gly Phe
                20                  25                  30

Trp Glu Glu Val Ala Ser Gly Gln Glu Asp Pro Thr Asp Pro
            35                  40                  45

( 2 ) INFORMATION FOR SEQ ID NO:36:

( i ) SEQUENCE CHARACTERISTICS:
       ( A ) LENGTH: 46 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:36:

Pro Val Ser Phe Gly Ala Glu Asp Pro Glu Thr Pro Phe Gln Thr Thr
1               5                   10                  15

Met Ala Ala Pro Gly Glu Ala Ser His Gly Ser Pro Glu Ala Asp Ser
                20                  25                  30

Ile Glu Ile Glu Gly Ile Ser Ser Met Gln Ala Thr Lys His
            35                  40                  45

( 2 ) INFORMATION FOR SEQ ID NO:37:

( i ) SEQUENCE CHARACTERISTICS:
       ( A ) LENGTH: 38 amino acids
       ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:37:

```
Pro Ile Ser Gly Pro Trp Ala Ser Leu Asp Ser Ser Asn Val Thr Val
1               5                   10                  15
Asn Pro Val Pro Ser Asp Ala Gly Ile Leu Gly Thr Glu Ser Gly Val
                20                  25                  30
Leu Asp Leu Pro Gly Ser
            35
```

(2) INFORMATION FOR SEQ ID NO:38:

(i) SEQUENCE CHARACTERISTICS:
(A) LENGTH: 43 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:38:

```
Pro Thr Ser Asp Gly Gln Ala Thr Val Asp Met Val Leu Ala Thr Trp
1               5                   10                  15
Leu Pro Leu Pro Gly His Gly Leu Asp Thr Gly Ser Gln Ser Thr Pro
                20                  25                  30
Met Glu Ala His Gly Val Thr Met Ser Val Glu
            35                  40
```

(2) INFORMATION FOR SEQ ID NO:39:

(i) SEQUENCE CHARACTERISTICS:
(A) LENGTH: 45 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:39:

```
Pro Thr Val Ala Leu Glu Gly Gly Ala Thr Lys Asp Pro Met Glu Ala
1               5                   10                  15
Thr Met Asp Val Val Pro Ser Thr Val Asp Ala Thr Ser Gly Ser Glu
                20                  25                  30
Pro Lys Ser Ser Ile Ser Ser Thr His Val Val Val Thr
            35                  40                  45
```

(2) INFORMATION FOR SEQ ID NO:40:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:40:

```
Ala Ala Gly Asp Gln Gly Thr Pro Thr Leu
1               5                   10
```

(2) INFORMATION FOR SEQ ID NO:41:

(i) SEQUENCE CHARACTERISTICS:

(A) LENGTH: 23 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:41:

Pro Thr Ser Ser Glu Gly Gln Val Val Ala Gln Glu Ser Leu Gly Thr
1               5                   10                  15
Leu Thr Ser Leu Pro Ser His
            20

(2) INFORMATION FOR SEQ ID NO:42:

(i) SEQUENCE CHARACTERISTICS:
    (A) LENGTH: 31 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:42:

Pro Trp Ser Ser Leu Ala Ser Ser Met Asp Glu Val Ala Ser Val Ser
1               5                   10                  15
Ser Gly Glu Pro Thr Arg Leu Trp Asp Ile Pro Ser Thr Leu Ile
            20                  25                  30

(2) INFORMATION FOR SEQ ID NO:43:

(i) SEQUENCE CHARACTERISTICS:
    (A) LENGTH: 33 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:43:

Pro Val Ser Leu Gly Leu Asp Glu Ser Asp Leu Lys Val Val Ala Glu
1               5                   10                  15
Ser Pro Gly Leu Glu Gly Phe Trp Glu Glu Val Ala Ser Gly Gln Glu
            20                  25                  30
Asp (2) INFORMATION FOR SEQ ID NO:44:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:44:

Cys Asp Ala Gly Trp Leu Ala Asp Gln
1               5

(2) INFORMATION FOR SEQ ID NO:45:

(i) SEQUENCE CHARACTERISTICS:
    (A) LENGTH: 13 amino acids
    (B) TYPE: amino acid
    (C) STRANDEDNESS: single
    (D) TOPOLOGY: linear 5,648,465

(ii) MOLECULE TYPE: peptide (ix) FEATURE:
    (A) NAME/KEY: Peptide
    (B) LOCATION: 2, 7, 11, 12
    (D) OTHER INFORMATION:/note"Xaa at pos. 2 Ala or Ser; Xaa at pos. 7 Arg or Gln; Xaa at pos. 11 = Ser or Thr; Xaa at pos. 12 Lys or Arg."

(xi) SEQUENCE DESCRIPTION: SEQ ID NO:45:

```
Leu  Xaa  Asp  Gly  Ser  Val  Xaa  Tyr  Pro  Ile  Xaa  Xaa  Pro
 1                    5                             10
```

(2) INFORMATION FOR SEQ ID NO:46:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

```
Pro  Ile  Ser  Gly  Pro
 1                    5
```

(2) INFORMATION FOR SEQ ID NO:47:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:47:

```
His  Pro  Ile  Ser  Gly  Pro  Trp
 1                    5
```

(2) INFORMATION FOR SEQ ID NO:48:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 3
        (D) OTHER INFORMATION:/note"Xaa at pos. 3 Ser or Thr."

(xi) SEQUENCE DESCRIPTION: SEQ ID NO:48:

```
Pro  Ile  Xaa  Xaa  Pro
 1                    5
```

(2) INFORMATION FOR SEQ ID NO:49:

(i) SEQUENCE CHARACTERISTICS:
        (A) LENGTH: 1257 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:49:

```
Met Gly Ala Glu Ser Val Trp Ala Ser Gly Leu Leu Val Leu Trp Leu
1               5                   10                  15
Leu Leu Leu Val Ser Gly Asp Gln Asp Thr Gln Asp Thr Thr Thr Thr
            20              25              30
Glu Lys Gly Leu His Met Leu Lys Ser Gly Ser Gly Pro Ile Gln Ala
        35              40              45
Ala Leu Ala Glu Leu Val Ala Leu Pro Cys Phe Phe Thr Leu Gln Pro
    50              55              60
Arg Gln Ser Pro Leu Gly Asp Ile Pro Arg Ile Lys Trp Thr Lys Val
65              70              75                              80
Gln Thr Ala Ser Gly Gln Arg Gln Asp Leu Pro Ile Leu Val Ala Lys
                85              90                      95
Asp Asn Val Val Arg Val Ala Lys Gly Trp Gln Gly Arg Val Ser Leu
            100             105                 110
Pro Ala Tyr Pro Arg His Arg Ala Asn Ala Thr Leu Leu Leu Gly Pro
        115             120                 125
Leu Arg Ala Ser Asp Ser Gly Leu Tyr Arg Cys Gln Val Val Lys Gly
    130                 135                 140
Ile Glu Asp Glu Gln Asp Leu Val Thr Leu Glu Val Thr Gly Val Val
145                 150                 155                 160
Phe His Tyr Arg Ala Ala Arg Asp Arg Tyr Ala Leu Thr Phe Ala Glu
                165                 170                 175
Ala Gln Glu Ala Cys His Leu Ser Ser Ala Thr Ile Ala Ala Pro Arg
            180                 185                 190
His Leu Gln Ala Ala Phe Glu Asp Gly Phe Asp Asn Cys Asp Ala Gly
        195                 200                 205
Trp Leu Ser Asp Arg Thr Val Arg Tyr Pro Ile Thr Gln Ser Arg Pro
    210                 215                 220
Gly Cys Tyr Gly Asp Arg Ser Ser Leu Pro Gly Val Arg Ser Tyr Gly
225                 230                 235                 240
Arg Arg Asp Pro Gln Glu Leu Tyr Asp Val Tyr Cys Phe Ala Arg Glu
                245                 250                 255
Leu Gly Gly Glu Val Phe Tyr Val Gly Pro Ala Arg Arg Leu Thr Leu
            260                 265                 270
Ala Gly Ala Arg Ala Leu Cys Gln Arg Gln Gly Ala Ala Leu Ala Ser
        275                 280                 285
Val Gly Gln Leu His Leu Ala Trp His Glu Gly Leu Asp Gln Cys Asp
    290                 295                 300
Pro Gly Trp Leu Ala Asp Gly Ser Val Arg Tyr Pro Ile Gln Thr Pro
305                 310                 315                 320
Arg Arg Arg Cys Gly Gly Ser Ala Pro Gly Val Arg Thr Val Tyr Arg
                325                 330                 335
Phe Ala Asn Arg Thr Gly Phe Pro Ala Pro Gly Ala Arg Phe Asp Ala
            340                 345                 350
Tyr Cys Phe Arg Ala His His His Thr Pro Gln Arg Gly Asp Ser Glu
        355                 360                 365
Ile Pro Ser Ser Gly Asp Glu Gly Glu Ile Val Ser Ala Glu Gly Pro
    370                 375                 380
Pro Ala Pro Glu Leu Lys Pro Arg Leu Gly Glu Gln Glu Val Ile Thr
385                 390                 395                 400
Pro Asp Phe Gln Glu Pro Leu Val Ser Ser Gly Glu Asp Glu Pro Leu
                405                 410                 415
Asp Leu Thr Arg Thr Gln Ala Ser Gln Glu Thr Leu Ala Ser Thr Pro
            420                 425                 430
```

| | | | | | | | | | | | | | | |
|---|---|---|---|---|---|---|---|---|---|---|---|---|---|---|
| Gly | Gly | Pro<br>435 | Thr | Leu | Ala | Ser | Trp<br>440 | Leu | Leu | Thr | Gly<br>445 | Val | Ser | Ser |
| Thr | Gly<br>450 | Val | Pro | Ser | Pro<br>455 | Ser | Leu | Gly | Val<br>460 | Asp | Met | Glu | Glu | Thr |
| Thr<br>465 | Pro | Ser | Gly | Thr<br>470 | Gln | Val | Ala | Pro<br>475 | Thr | Pro | Thr | Met | Arg | Arg<br>480 Gly |
| Arg | Phe | Lys | Gly | Leu<br>485 | Asn | Gly | Arg | His<br>490 | Phe | Gln | Gln | Gln | Gly | Pro<br>495 Glu |
| Asp | Gln | Leu | Leu<br>500 | Glu | Ala | Ala | Glu<br>505 | Ala | Ser | Ala | Gln | Pro<br>510 | Pro | Thr Leu |
| Glu | Val | Thr<br>515 | Ala | Asp | His | Met<br>520 | Gly | Pro | Ser | Ala | Ala<br>525 | Thr | Glu | Ala Leu |
| Glu | Ser<br>530 | Asp | Gln | Ser | His | Ser<br>535 | Pro | Trp | Ala | Ile | Leu<br>540 | Thr | Asn | Glu Val |
| Asp<br>545 | Val | Pro | Gly | Ala | Gly<br>550 | Ser | Leu | Gly | Ser | Arg<br>555 | Ser | Leu | Pro | Glu Ser<br>560 |
| Arg | Lys | Trp | Ser | Pro<br>565 | Ser | Leu | Ile | Ser | Pro<br>570 | Ser | Thr | Val | Pro | Ser Thr<br>575 |
| Asp | Ser | Thr | Pro<br>580 | Gly | Leu | Lys | Pro<br>585 | Gly | Ala | Asp | Glu<br>590 | Ala | Pro | Gly Val |
| Lys | Ser | Ala<br>595 | Ile | His | His | Pro<br>600 | Pro | Trp | Leu | Pro<br>605 | Ser | Glu | Pro | Ala Val |
| Pro | Ser<br>610 | Ser | Ile | Pro | Ser<br>615 | Glu | Ala | Leu | Ser<br>620 | Ala | Val | Ser | Leu | Gln Ala |
| Ser<br>625 | Pro | Gly | Asp | Gly<br>630 | Ser | Pro | Asp | Phe<br>635 | Pro | Ile | Val | Ala | Met | Leu Arg<br>640 |
| Ala | Pro | Lys | Leu<br>645 | Trp | Leu | Leu | Pro<br>650 | His | Ser | Thr | Leu<br>655 | Val | Pro | Asn Val |
| Ser | Pro | Ile<br>660 | Pro | Leu | Ser | Pro<br>665 | Ala | Ser | Pro | Leu<br>670 | Pro | Ser | Ser | Val Pro |
| Glu | Glu | Gln<br>675 | Ala | Val | Arg | Pro<br>680 | Val | Ser | Phe | Gly<br>685 | Ala | Glu | Asp | Pro Glu |
| Thr | Pro<br>690 | Phe | Gln | Thr | Thr<br>695 | Met | Ala | Ala | Pro<br>700 | Gly | Glu | Ala | Ser | His Gly |
| Ser<br>705 | Pro | Glu | Ala | Asp<br>710 | Ser | Ile | Glu | Ile<br>715 | Glu | Gly | Ile | Ser | Ser | Met Gln<br>720 |
| Ala | Thr | Lys | His<br>725 | Pro | Ile | Ser | Gly<br>730 | Pro | Trp | Ala | Ser<br>735 | Leu | Asp | Ser Ser |
| Asn | Val | Thr<br>740 | Val | Asn | Pro | Val<br>745 | Pro | Ser | Asp | Ala<br>750 | Gly | Ile | Leu | Gly Thr |
| Glu | Ser<br>755 | Gly | Val | Leu | Asp<br>760 | Leu | Pro | Gly | Ser | Pro<br>765 | Thr | Ser | Asp | Gly Gln |
| Ala | Thr<br>770 | Val | Asp | Met | Val<br>775 | Leu | Ala | Thr | Trp<br>780 | Leu | Pro | Leu | Pro | Gly His |
| Gly<br>785 | Leu | Asp | Thr | Gly<br>790 | Ser | Gln | Ser | Thr<br>795 | Pro | Met | Glu | Ala | His | Gly Val<br>800 |
| Thr | Met | Ser<br>805 | Val | Glu | Pro | Thr<br>810 | Val | Ala | Leu | Glu<br>815 | Gly | Gly | Ala | Thr Lys |
| Asp | Pro<br>820 | Met | Glu | Ala | Thr<br>825 | Met | Asp | Val | Val<br>830 | Pro | Ser | Thr | Val | Asp Ala |
| Thr | Ser<br>835 | Gly | Ser | Glu | Pro<br>840 | Lys | Ser | Ser | Ile<br>845 | Ser | Ser | Thr | His | Val Val |
| Val | Thr | Ala | Ala | Gly | Asp | Gln | Gly | Thr | Pro | Thr | Leu | Thr | Pro | Thr Ser |

-continued

|  |  |  | 850 |  |  |  | 855 |  |  |  | 860 |  |  |
|---|---|---|---|---|---|---|---|---|---|---|---|---|---|
| Ser | Glu | Gly | Gln | Val | Val | Ala | Gln | Glu | Ser | Leu | Gly | Thr | Leu | Thr | Ser |
| 865 |  |  |  | 870 |  |  |  | 875 |  |  |  | 880 |
| Leu | Pro | Ser | His | Pro | Trp | Ser | Ser | Leu | Ala | Ser | Ser | Met | Asp | Glu | Val |
|  |  |  | 885 |  |  |  | 890 |  |  |  | 895 |
| Ala | Ser | Val | Ser | Ser | Gly | Glu | Pro | Thr | Arg | Leu | Trp | Asp | Ile | Pro | Ser |
|  |  |  | 900 |  |  |  | 905 |  |  |  | 910 |
| Thr | Leu | Ile | Pro | Val | Ser | Leu | Gly | Leu | Asp | Glu | Ser | Asp | Leu | Lys | Val |
|  |  |  | 915 |  |  |  | 920 |  |  |  | 925 |
| Val | Ala | Glu | Ser | Pro | Gly | Leu | Glu | Gly | Phe | Trp | Glu | Glu | Val | Ala | Ser |
|  |  |  | 930 |  |  |  | 935 |  |  |  | 940 |
| Gly | Gln | Glu | Asp | Pro | Thr | Asp | Pro | Cys | Glu | Asn | Asn | Pro | Cys | Leu | His |
| 945 |  |  |  | 950 |  |  |  | 955 |  |  |  | 960 |
| Gly | Gly | Thr | Cys | Arg | Thr | Asn | Gly | Thr | Met | Tyr | Gly | Cys | Ser | Cys | Asp |
|  |  |  | 965 |  |  |  | 970 |  |  |  | 975 |
| Gln | Gly | Tyr | Ala | Gly | Glu | Asn | Cys | Glu | Ile | Asp | Ile | Asp | Asp | Cys | Leu |
|  |  |  | 980 |  |  |  | 985 |  |  |  | 990 |
| Cys | Ser | Pro | Cys | Glu | Asn | Gly | Gly | Thr | Cys | Ile | Asp | Glu | Val | Asn | Gly |
|  |  |  | 995 |  |  |  | 1000 |  |  |  | 1005 |
| Phe | Ile | Cys | Leu | Cys | Leu | Pro | Ser | Tyr | Gly | Gly | Asn | Leu | Cys | Glu | Lys |
|  |  |  | 1010 |  |  |  | 1015 |  |  |  | 1020 |
| Asp | Thr | Glu | Gly | Cys | Asp | Arg | Gly | Trp | His | Lys | Phe | Gln | Gly | His | Cys |
| 1025 |  |  |  | 1030 |  |  |  | 1035 |  |  |  | 1040 |
| Tyr | Arg | Tyr | Phe | Ala | His | Arg | Arg | Ala | Trp | Glu | Asp | Ala | Glu | Arg | Asp |
|  |  |  | 1045 |  |  |  | 1050 |  |  |  | 1055 |
| Cys | Arg | Arg | Arg | Ala | Gly | His | Leu | Thr | Ser | Val | His | Ser | Pro | Glu | Glu |
|  |  |  | 1060 |  |  |  | 1065 |  |  |  | 1070 |
| His | Lys | Phe | Ile | Asn | Ser | Phe | Gly | His | Glu | Asn | Ser | Trp | Ile | Gly | Leu |
|  |  |  | 1075 |  |  |  | 1080 |  |  |  | 1085 |
| Asn | Asp | Arg | Thr | Val | Glu | Arg | Asp | Phe | Gln | Trp | Thr | Asp | Asn | Thr | Gly |
|  |  |  | 1090 |  |  |  | 1095 |  |  |  | 1100 |
| Leu | Gln | Tyr | Glu | Asn | Trp | Arg | Glu | Lys | Gln | Pro | Asp | Asn | Phe | Phe | Ala |
| 1105 |  |  |  | 1110 |  |  |  | 1115 |  |  |  | 1120 |
| Gly | Gly | Glu | Asp | Cys | Val | Val | Met | Val | Ala | His | Glu | Asn | Gly | Arg | Trp |
|  |  |  | 1125 |  |  |  | 1130 |  |  |  | 1135 |
| Asn | Asp | Val | Pro | Cys | Asn | Tyr | Asn | Leu | Pro | Tyr | Val | Cys | Lys | Lys | Gly |
|  |  |  | 1140 |  |  |  | 1145 |  |  |  | 1150 |
| Thr | Val | Leu | Cys | Gly | Pro | Pro | Pro | Ala | Val | Glu | Asn | Ala | Ser | Leu | Val |
|  |  |  | 1155 |  |  |  | 1160 |  |  |  | 1165 |
| Gly | Val | Arg | Lys | Val | Lys | Tyr | Asn | Val | His | Ala | Thr | Val | Arg | Tyr | Gln |
|  |  |  | 1170 |  |  |  | 1175 |  |  |  | 1180 |
| Cys | Asp | Glu | Gly | Phe | Ser | Gln | His | His | Val | Ala | Thr | Ile | Arg | Cys | Arg |
| 1185 |  |  |  | 1190 |  |  |  | 1195 |  |  |  | 1200 |
| Ser | Asn | Gly | Lys | Trp | Asp | Arg | Pro | Gln | Ile | Val | Cys | Thr | Lys | Pro | Arg |
|  |  |  | 1205 |  |  |  | 1210 |  |  |  | 1215 |
| Arg | Ser | His | Arg | Met | Arg | Arg | His | His | His | Pro | His | Arg | His | His |
|  |  |  | 1220 |  |  |  | 1225 |  |  |  | 1230 |
| Lys | Pro | Arg | Lys | Glu | His | Arg | Lys | His | Lys | Arg | His | Pro | Ala | Glu | Asp |
|  |  |  | 1235 |  |  |  | 1240 |  |  |  | 1245 |
| Trp | Glu | Lys | Asp | Glu | Gly | Asp | Phe | Cys |
|  |  |  | 1250 |  |  |  | 1255 |